US011040958B2

(12) United States Patent
Tang et al.

(10) Patent No.: US 11,040,958 B2
(45) Date of Patent: Jun. 22, 2021

(54) TRIAZOLE ANTIMICROBIAL DERIVATIVE, PHARMACEUTICAL COMPOSITION AND USE THEREOF

(71) Applicants: WUHAN LL SCIENCE AND TECHNOLOGY DEVELOPMENT CO., LTD., Hubei (CN); WUHAN QR PHARMACEUTICALS CO., LTD., Hubei (CN)

(72) Inventors: Hongwei Tang, Hubei (CN); Jun Lou, Hubei (CN); Penggao Yu, Hubei (CN); Li Liu, Hubei (CN); Anxiao Zheng, Hubei (CN); Yongkai Chen, Hubei (CN); Chaodong Wang, Hubei (CN)

(73) Assignees: WUHAN LL SCIENCE AND TECHNOLOGY DEVELOPMENT CO., LTD., Hubei (CN); WUHAN QR PHARMACEUTICALS CO., LTD., Hubei (CN)

( * ) Notice: Subject to any disclaimer, the term of this patent is extended or adjusted under 35 U.S.C. 154(b) by 0 days.

(21) Appl. No.: 16/486,761

(22) PCT Filed: Feb. 8, 2018

(86) PCT No.: PCT/CN2018/075862
§ 371 (c)(1),
(2) Date: Aug. 16, 2019

(87) PCT Pub. No.: WO2018/149359
PCT Pub. Date: Aug. 23, 2018

(65) Prior Publication Data
US 2019/0382375 A1    Dec. 19, 2019

(30) Foreign Application Priority Data
Feb. 17, 2017    (CN) .......................... 201710087041.2

(51) Int. Cl.
| | | |
|---|---|---|
| *C07D 401/14* | (2006.01) | |
| *C07D 403/06* | (2006.01) | |
| *C07F 9/6558* | (2006.01) | |
| *C07H 13/04* | (2006.01) | |
| *A61P 31/10* | (2006.01) | |

(52) U.S. Cl.
CPC ............ *C07D 401/14* (2013.01); *A61P 31/10* (2018.01); *C07D 403/06* (2013.01); *C07F 9/65583* (2013.01); *C07H 13/04* (2013.01)

(58) Field of Classification Search
None
See application file for complete search history.

(56) References Cited

U.S. PATENT DOCUMENTS

| | | |
|---|---|---|
| 6,235,728 B1 | 5/2001 | Golik et al. |
| 6,300,353 B1 | 10/2001 | Hayase et al. |

FOREIGN PATENT DOCUMENTS

| | | |
|---|---|---|
| CN | 1251098 A | 4/2000 |
| CN | 1261287 A | 7/2000 |
| CN | 1387529 A | 12/2002 |
| CN | 101391985 A | 3/2009 |
| CN | 103626825 A | 3/2014 |
| CN | 104230894 A | 12/2014 |
| CN | 106467519 A | 3/2017 |
| WO | 2008106860 A1 | 9/2008 |

(Continued)

OTHER PUBLICATIONS

Zhang Yiyi et al.: "Synthesis of Novel Fluconazoliums and Their Evaluation for Antibacterial and Antifungal Activities", European Journal of Medicinal Chemistry, vol. 46, No. 9, Jul. 8, 2011 (Jul. 8, 2011), pp. 4391-4402, XP028278342, ISSN: 0223-5234.

(Continued)

*Primary Examiner* — Layla D Berry
(74) *Attorney, Agent, or Firm* — Novick, Kim & Lee, PLLC; Allen Xue

(57) ABSTRACT

The present disclosure provides a triazole antibacterial derivative and a pharmaceutical composition thereof and a use thereof and in particular relates to a compound represented by the following formula (I), and a racemate, a stereoisomer, a tautomer, an oxynitride or a pharmaceutically acceptable salt thereof:

(I)

The compound of the present disclosure has a desirable water solubility and can be formulated into an injection for use without adding a cosolvent having a potential safety risk (such as hydroxypropyl-β-cyclodextrin, sulfobutylether-β-cyclodextrin, and the like), facilitating drug administration for patients, and greatly improving clinical safety. The drug can be used even by patients with moderate or severe renal impairment, thereby expanding the application scope of the drug.

15 Claims, No Drawings

(56) References Cited

FOREIGN PATENT DOCUMENTS

WO      2013130660 A    9/2013
WO      2015112801 A1   7/2015

OTHER PUBLICATIONS

Rybak Jeffrey M. et al.: "Isavuconazole: Pharmacology, Pharmacodynamics, and Current Clinical Experience with a New Triazole Antifungal Agent", Pharmacotherapy, vol. 35, No. 11, Dec. 31, 2015 (Dec. 31, 2015), pp. 1037-1051, XP055535100, ISSN: 1875-9114.

TRIAZOLE ANTIMICROBIAL DERIVATIVE, PHARMACEUTICAL COMPOSITION AND USE THEREOF

CROSS-REFERENCE TO RELATED APPLICATIONS

This application claims the benefit of and priority to the prior Chinese patent application No. 201710087041.2, entitled "TRIAZOLE ANTIMICROBIAL DERIVATIVE, PHARMACEUTICAL COMPOSITION AND USE THEREOF" and filed before the Chinese National Intellectual Property Office on Feb. 17, 2017, which is hereby incorporated by reference in its entirety.

TECHNICAL FIELD

The present disclosure belongs to the field of antimicrobial drug, and in particular relates to triazole antimicrobial derivatives having antifungal activity, pharmaceutical compositions and uses thereof.

BACKGROUND OF THE INVENTION

Fungal infection is a common and frequently-occurring disease in clinic, which can be divided into two types: superficial fungal infection and deep fungal infection. Among them, the superficial infection, caused by the invasion of skin, hair, nails and other body parts by sputum, has a high incidence and low harmfulness, while the deep fungal infection, caused by fungi that invade internal organs and deep tissues such as *Candida, Aspergillus* and *Cryptococcus*, has relative high harmfulness.

In recent years, with the increasing number of immunosuppressed patients, the incidence of the deep fungal infection has increased significantly, leading to a widespread concern about the fungal infection, especially the deep fungal infection. However, current antifungal drugs applied in clinic have issues such as serious side effects and being prone to drug resistance, which make the effective antifungal drugs still very scarce. The existing antifungal drugs can be classified into organic acids, polyenes, azoles, allylamines and the like according to their structures. Among them, azole antifungal drugs are a kind of fast-developing, fully synthesized antifungal compounds, which have become the main drugs for the treatment of deep and superficial fungal infections for clinic application. Since the first azole compound was reported to have antifungal effects in the middle of the last century, the first-generation triazole drug fluconazole, itraconazole, and the second-generation triazole drug voriconazole gradually appeared in the field of antifungal therapy.

Voriconazole is the derivative of fluconazole, which was first approved in the United States in 2002 and subsequently marketed, which is clinically effective against *Aspergillus, Candida*, and Actinomycetes, and even drug-resistance Fungi, with antibacterial spectrum similar to itraconazole or even better than it. However, the absorption degree of the oral suspension of the drug is highly susceptible to food, gastrointestinal function and the like, resulting in large differences in pharmacokinetic parameters between individuals, large fluctuation range of drug concentration in blood, low bioavailability and other issues. Further, the voriconazole compound itself has disadvantages such as poor solubility and difficulty in development into an injection form, while some immunosuppressed patients receiving chemotherapy or organ transplantation have problems such as nausea and vomiting and gastrointestinal discomfort, leading to difficulties in oral administration and the need for injectable drug delivery.

At present, in order to solve the problem that voriconazole is difficult to develop into an injection preparation due to poor solubility, substituted β-cyclodextrins has been generally used to solubilize voriconazole for injection preparation. The voriconazole injection approved by the US Food and Drug Administration uses sulfobutylether-β-cyclodextrin to solve the solubility problem, which although overcomes the defect that voriconazole is insoluble in water, enabling the administration for patients inconvenient for oral administration, but increases potential drug safety risks due to the addition of a large amount of sulfobutylether-β-cyclodextrin (SBE-β-CD) for solubilization. Preclinical toxicology studies have shown that sulfobutylether-β-cyclodextrin causes vacuolar formation of urothelial cells and activation of macrophages in the liver and lung. Moreover, clinical studies have shown that sulfobutylether-β-cyclodextrin is mainly cleared by the kidneys in the body, which may lead to acute renal failure in patients, while patients with target indications of voriconazole injections are mostly immunosuppressed patients receiving bone marrow transplantation or chemotherapy with high risk of fungal infection. A considerable proportion of these patients have renal impairment, especially those with moderate or severe renal insufficiency, due to the low efficiency of glomerular filtration of whom, sulfobutylether-β-cyclodextrin accumulates in large amounts in their body, significantly increasing safety risks. In particular, the instruction of the voriconazole injection indicates that the drug is not suitable for patients with moderate or severe renal impairment. The use of the adjuvant sulfobutylether-β-cyclodextrin greatly limits the clinical application of the drug. Therefore, it is of great value to improve the deficiencies in the prior art and increase the drug safety and drug applicability for patients with renal impairment.

SUMMARY OF THE INVENTION

In order to improve the problems existing in the prior art, the present disclosure provides a compound represented by the following formula (I), a racemate, a stereoisomer, a tautomer, an oxynitride or a pharmaceutically acceptable salt thereof:

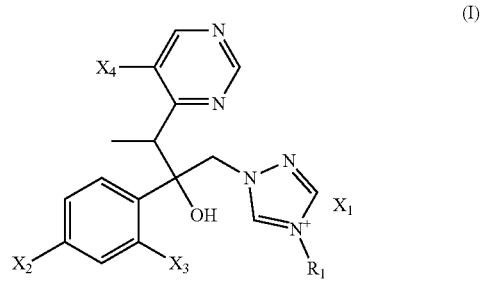

wherein, $R_1$ is selected from the group consisting of

[Chemical structures showing three variants with $R_2$, $R_3$, $R_4$, $R_5$, $R_6$, $R_7$, $R_8$, Ar, $Y_1$, and O substituents]

$X_1$ is independently selected from a pharmaceutically acceptable anion;

$X_2$, $X_3$, $X_4$ may be the same or different, and are independently selected from the group consisting of F, Cl, Br, I;

$R_2$, $R_4$ may be the same or different, independently selected from H, or $C_{1-40}$ alkyl which is unsubstituted or optionally substituted by one or more $R_a$;

$R_3$ is selected from $C_{1-40}$ alkyl which is unsubstituted or optionally substituted by one or more $R_b$;

$R_5$, $R_6$ may be the same or different, independently selected from H, or the following groups which are unsubstituted or optionally substituted by one or more $R_m$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, —C(O)$R_f$;

Ar is selected from the following groups which are unsubstituted or optionally substituted by one or more $R_c$: $C_{6-20}$ aryl, 5-20 membered heteroaryl, wherein the 5-20 membered heteroaryl comprises 1-5 heteroatoms independently selected from N, O and S; $R_7$ is selected from the following groups which are unsubstituted or optionally substituted by one or more $R_c$: $C_{1-40}$ alkyl, $C_{3-20}$ cycloalkyl, 3-20 membered heterocyclyl, $C_{6-20}$ aryl, 5-20 membered heteroaryl, —$Y_2$P(O)(OM$_1$)(OM$_2$), —C(O)$R_f$ or —(CH$_2$CH$_2$O)$_z$—$R_b$;

$R_8$ is selected from H, or the following groups which are unsubstituted or optionally substituted by one or more $R_b$: $C_{1-40}$ alkyl, $C_{3-20}$ cycloalkyl, 3-20 membered heterocyclyl, $C_{6-20}$ aryl, 5-20 membered heteroaryl, —NR$_d$R$_e$, —CONR$_d$R$_e$, —C(O)Y$_2$R$_f$, —Y$_2$C(O)R$_f$, —Y$_2$P(O)(OM$_1$)(OM$_2$), —Y$_2$S(O)$_2$OM$_3$;

$Y_1$, $Y_2$ may be the same or different, independently selected from the group consisting of a chemical bond, —O—, —S—, or the following groups which are unsubstituted or optionally substituted by one or more $R_a$: —NH—, $C_{1-40}$ alkyl, $C_{1-40}$ alkoxy, $C_{3-20}$ cycloalkyl, 3-20 membered heterocyclyl, $C_{6-20}$ aryl, 5-20 membered heteroaryl, —(CH$_2$CH$_2$O)$_j$—;

each $R_a$ may be the same or different, independently selected from H, $C_{1-40}$ alkyl, $C_{1-40}$ alkoxy, $C_{2-40}$ alkenyl, $C_{2-40}$ alkynyl, $C_{3-20}$ cycloalkyl, F, Cl, Br, I, OH, SH, CN, =O, —NR$_d$R$_e$, —C(O)Y$_2$R$_f$, —Y$_2$C(O)R$_f$, —CONR$_d$R$_e$—, —Y$_2$P(O)(OM$_1$)(OM$_2$) or —Y$_2$S(O)$_2$OM$_3$;

each $R_b$ may be the same or different, independently selected from H, F, Cl, Br, I, OH, SH, CN, or the following groups which are unsubstituted or optionally substituted by one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, $C_{3-20}$ cycloalkyloxy, 3-20 membered heterocyclyl, 3-20 membered heterocyclyloxy, $C_{6-20}$ aryl, $C_{6-20}$ aryloxy, 5-20 membered heteroaryl, 5-20 membered heteroaryloxy, —[(CH$_2$)$_n$O]$_m$—, —NR$_d$R$_e$, —CONR$_d$R$_e$, —C(O)Y$_2$R$_f$, —Y$_2$C(O)R$_f$, —Y$_2$P(O)(OM$_1$)(OM$_2$), —Y$_2$S(O)$_2$OM$_3$;

each $R_c$ may be the same or different, independently selected from F, Cl, Br, I, OH, SH, CN, or the following groups which are unsubstituted or optionally substituted by one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, $C_{3-20}$ cycloalkyloxy, 3-20 membered heterocyclyloxy, $C_{6-20}$ aryloxy, 5-20 membered heteroaryloxy, —NR$_d$R$_e$, —CONR$_d$R$_e$, —C(O)Y$_2$R$_f$, —Y$_2$C(O)R$_f$, —Y$_2$P(O)(OM$_1$)(OM$_2$), —Y$_2$S(O)$_2$OM$_3$;

each $R_d$, $R_e$ may be the same or different, independently selected from H, or the following groups which are unsubstituted or optionally substituted by one or more $R_m$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, —CONR$_f$R$_g$, —C(O)Y$_2$R$_f$, —Y$_2$C(O)R$_f$, —Y$_2$P(O)(OM$_1$)(OM$_2$), —Y$_2$S(O)$_2$OM$_3$;

each $R_f$, $R_g$ may be the same or different, independently selected from H, or the following groups which are unsubstituted or optionally substituted by one or more $R_m$: $C_{1-40}$ alkyl, $C_{2-40}$ alkenyl, $C_{2-40}$ alkynyl, $C_{3-20}$ cycloalkyl, COOH, 3-20 membered heterocyclyl, $C_{6-20}$ aryl, 5-20 membered heteroaryl;

Each $R_m$ may be the same or different, independently selected from H, F, Cl, Br, I, OH, SH, CN, or the following groups which are unsubstituted or optionally substituted by one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, —NR$_d$R$_e$, —CONR$_d$R$_e$, —C(O)Y$_2$R$_f$, —Y$_2$C(O)R$_f$, —Y$_2$P(O)(OM$_1$)(OM$_2$), —Y$_2$S(O)$_2$OM$_3$;

$M_1$, $M_2$, $M_3$ may be the same or different, independently selected from H or $C_{1-40}$ alkyl unsubstituted or optionally substituted by one or more $R_b$;

n, m, j and z may be the same or different, independently selected from an integer of 1 or more, for example, an integer of 1 to 20, for example, 1, 2, 3, 4, 5, 6, 7, 8, 9 or 10.

According to an embodiment of the present disclosure, $X_1$ may represent an anion formed by ionization of an inorganic acid or an organic acid;

for example, $X_1$ may represent a monovalent anion formed by ionization of inorganic or organic acids;

alternatively, when a plurality of cations are present in the structure of the compound of formula (I), $X_1$ may represent a plurality of monovalent anions formed by ionization of inorganic or organic acids, preferably 2 or 3 monovalent anions formed by ionization of inorganic or organic acids;

alternatively, when a plurality of cations in the structure of the compound of the formula (I) share a polyvalent anion, $X_1$ may also represent a part of the polyvalent anion, for example, ½, ⅓, ⅔ of the polyvalent anion;

alternatively, $X_1$ may also represent a mixture of the above monovalent anions, a mixture of polyvalent anions or a mixture of monovalent anions and polyvalent anions;

the inorganic acid such as hydrochloric acid, hydrofluoric acid, hydrobromic acid, hydroiodic acid, sulfuric acid, pyrosulfuric acid, phosphoric acid or nitric acid;

the organic acid is, for example, formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectic acid, persulfate, 3-phenylpropionic acid, picric acid, pivalic acid, 2-hydroxyethanesulfonic acid, itaconic acid, sulfamic acid, trifluoromethanesulfonic acid, lauryl sulfate, ethanesulfonic acid, benzenesulfonic acid, p-toluene sulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, algae acid, maleic acid, fumaric acid, D-gluconic acid, mandelic acid, ascorbic acid, glucoheptanoic acid, glycerol phosphate, aspartic acid, sulfosalicylic acid, hemisulfuric acid or thiocyanic acid;

for example, $X_1$ may represent one or more selected from the group consisting of Cl$^-$, Br$^-$, I$^-$, HSO$_4^-$, NO$_3^-$, 1/2SO$_4^{2-}$, SO$_4^{2-}$, 3/2SO$_4^{2-}$, H$_2$PO$_4^-$, HPO$_4^{2-}$, 1/2HPO$_4^{2-}$, 3/2HPO$_4^{2-}$, 1/3PO$_4^{3-}$, 2/3PO$_4^{3-}$, PO$_4^{3-}$;

$R_2$ may be selected from H, or $C_{1-40}$ alkyl, such as methyl, which is unsubstituted or optionally substituted by one or more $R_a$;

$R_3$ may be selected from $C_{1-40}$ alkyl unsubstituted or optionally substituted by one or more $R_b$; for example, $R_3$ may be $C_{1-40}$ alkyl substituted by 1, 2 or 3 groups which are independently selected from $C_{1-6}$ alkyl, —NH$_2$, —COOH, —OH, —CONH$_2$, —N(CH$_3$)$_2$, —NH(CH$_3$), —NHCONH$_2$, —NH(CH$_2$)$_k$CH$_3$ or hydroxyphenyl (such as o-hydroxyphenyl, m-hydroxyphenyl or p-hydroxyphenyl);

as an example, $R_3$ may be selected from —(CH$_2$)$_k$—NH$_2$, —CH(NH$_2$)—(CH$_2$)$_k$—NH$_2$, —CH(NH$_2$)—(CH$_2$)$_k$—COOH, —(CH$_2$)$_k$—CH(NH$_2$)—COOH, —(CH$_2$)$_k$—COOH, —CH(NH$_2$)—(CH$_2$)$_k$—NH—CONH$_2$, —CH(NH$_2$)—(CH$_2$)$_k$—CONH$_2$, —CH(NH$_2$)—(CH$_2$)$_k$—OH, —CH(NH$_2$)—(CH$_2$)$_k$—CH(OH)—CH$_3$, —CH(NH$_2$)—(CH$_2$)$_k$—(C$_6$H$_4$)—OH, —CH(NH$_2$)—(CH$_2$)$_k$—NH—(CH$_2$)$_p$—CH$_3$, —(CH$_2$)$_k$—NH—(CH$_2$)$_p$—CH$_3$, —(CH$_2$)$_k$—N(CH$_3$)$_2$.

Ar may be selected from the following group optionally substituted by one or more $R_e$: $C_{6-10}$ aryl, 5-10 membered heteroaryl;

for example, Ar may be selected from pyridyl, phenyl, and specifically may be

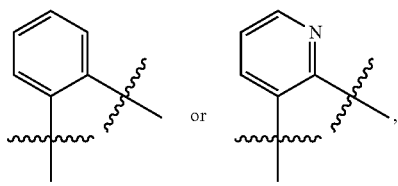 [SMILES: *c1ccccc1* ; *c1cccnc1*]

wherein the 2-position C atom of the pyridyl is bonded to the N atom, and the 3-position C atom of the pyridyl is bonded to the methylene group.

$R_7$ may be selected from the following group optionally substituted by one or more $R_e$: $C_{1-40}$ alkyl, $C_{3-20}$ cycloalkyl, 3-20 membered heterocyclyl, $C_{6-20}$ aryl, 5-20 membered, aryl, —OP(O)(OM$_1$)(OM$_2$), —SP(O)(OM$_1$)(OM$_2$), —P(O)(OM$_1$)(OM$_2$), —C(O)R$_f$ or —(CH$_2$CH$_2$O)$_z$—R$_b$;

for example, $R_7$ may be selected from the following groups: $C_{1-40}$ alkyl, 3-20 membered heterocyclyl, $C_{3-20}$ cycloalkyl, —(CH$_2$CH$_2$O)$_z$—R$_b$, wherein the groups are optionally substituted by 1, 2 or 3 groups independently selected from —OP(O)(OH)$_2$, —COOH, —NH$_2$, —SH, —OH, —NHCH$_3$, —OC(O)CH$_2$NHCH$_3$, —CH$_2$OH;

as an exemplary example, $R_7$ may be —(CH$_2$)$_k$—OP(O)(OH)$_2$, —(CH$_2$)$_k$—COOH, —(CH$_2$)$_k$—CH(NH$_2$)—COOH, —[(CH$_2$)$_z$—O]$_k$—OP(O)(OH)$_2$, —(CH$_2$)$_k$—SH, —(CH$_2$)$_k$—CH[NH(CH$_3$)]—COOH, —(CH$_2$)$_k$—OH, —(CH$_2$)$_k$—NH$_2$ or

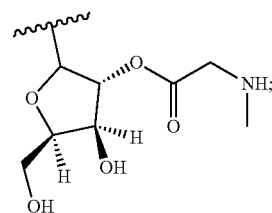 [SMILES: *C1O[C@H](CO)[C@H](O)[C@H]1OC(=O)CNC]

$R_8$ may be selected from H or the following groups optionally substituted by one or more $R_b$:

$C_{1-40}$ alkyl, $C_{3-20}$ cycloalkyl, 3-20 membered heterocyclyl, $C_{6-20}$ aryl, 5-20 membered heteroaryl, —NR$_d$R$_e$, —CONR$_d$R$_e$, —C(O)OR$_f$, —OC(O)R$_f$, —C(O)R$_f$, —OP(O)(OM$_1$)(OM$_2$), —SP(O)(OM$_1$)(OM$_2$), —P(O)(OM$_1$)(OM$_2$), —OS(O)$_2$OM$_3$;

for example, $R_8$ may be selected from the following groups: $C_{1-40}$ alkyl, 3-20 membered heterocyclyl or $C_{3-20}$ cycloalkyl, wherein the groups are optionally substituted by 1, 2 or 3 groups independently selected from —OP(O)(OH)$_2$, —COOH, —NH$_2$, —SH, —OH, —NHCH$_3$, —OC(O)CH$_2$NHCH$_3$, —CH$_2$OH;

as an exemplary example, $R_8$ may be —(CH$_2$)$_k$—OP(O)(OH)(OH) or —(CH$_2$)$_k$—COOH;

$Y_1$, $Y_2$ may be independently selected from the group consisting of a chemical bond, —O—, —S—, or the following groups which are unsubstituted or optionally substituted by one or more $R_a$: —CH$_2$—, —NH—;

k, p may be the same or different, independently selected from an integer of 0 to 16, for example, 0, 1, 2, 3, 4, 5, 6, 7, 8, 9 or 10;

$R_a$, $R_b$, $R_e$, $R_d$ and z independently have the definitions described above.

$R_a$, $R_b$, $R_e$, $R_d$ and z independently have the definitions described above.

According to an embodiment of the invention, the pharmaceutically acceptable salt of the compound of formula (I) comprises, but is not limited to:

an alkali metal salt, alkaline earth metal salt, ammonium salt of the compound of formula (I), or a salt formed by the compound of formula (I) with an organic base which provides a physiologically acceptable cation, for example, a salt formed by the compound of formula (I) with sodium ion, potassium ion, calcium ion, magnesium Ionic, N-methylglucamine, dimethyl glucosamine, ethyl glucosamine, lysine, dicyclohexylamine, 1,6-hexamethylenediamine, ethanolamine, glucosamine, meglumine, sarcosine, serinol, trishydroxymethylaminomethane, aminopropanediol, 1-amino-2,3,4-butanetriol. As an example, the pharmaceutically acceptable salt comprises a salt formed by —COOH group with sodium ion, potassium ion, calcium ion, magnesium ion, N-methylglucamine, dimethyl glucosamine, ethyl glucosamine, lysine, dicyclohexylamine, 1,6-hexamethylenediamine, ethanolamine, glucosamine, meglumine, sarcosine, serinol, trishydroxymethylaminomethane, aminopropanediol, 1-amino-2,3,4-butanetriol; when 1, 2 or 3 of $M_1$, $M_2$ and $M_3$ are H, the pharmaceutically acceptable salts of the invention comprises, for example, salts formed by —OP(O)(OM$_1$)(OM$_2$), —P(O)(OM$_1$)(OM$_2$), —OS(O)$_2$OM$_3$, —S(O)$_2$OM$_3$ with the following substances: sodium ion, potassium ion, calcium ion, magnesium ion, N-methyl glucosamine, dimethyl glucosamine, ethyl glucosamine, lysine, dicyclohexylamine, 1,6-hexamethylenediamine, ethanolamine, glucosamine, meglumine, sarcosine, serinol, trishydroxymethylaminomethane, aminopropanediol or 1-amino-2,3,4-butanetriol.

Alternatively, the compound of formula (I) is formed to an acid addition salt with an acid selected from: inorganic acids such as hydrochloric acid, hydrofluoric acid, hydrobromic acid, hydroiodic acid, sulfuric acid, pyrosulfuric acid, phosphoric acid or nitric acid; organic acids such as formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectic acid, persulfate, 3-phenylpropionic acid, picric acid, pivalic acid, 2-hydroxyethanesulfonic acid, itaconic acid, sulfamic acid, trifluoromethanesulfonic acid, lauryl sulfate, ethanesulfonic acid, benzenesulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid or thiocyanic acid.

It will be understood by those skilled in the art that the compound of formula (I) may contain one or more amino acid ester substituents and/or other basic groups which can form acid addition salts with the above acids. If appropriate, the pharmaceutically acid addition salts of the compound of formula (I) comprise not only a salt formed by one molecule of the compound of formula (I) with one molecule of the acid, but also a salt formed by a plurality of molecules of the compound of formula (I) with one molecule of the acid (e.g. half sulfate), a salt formed by one molecule of the compound of formula (I) with a plurality of molecules of the acid, and a salt formed by a plurality of molecules of the compound of formula (I) with a plurality of molecules of the acid. Further, the alkali metal salt, alkaline earth metal salt, ammonium salt of the compound of the formula (I) or the salt formed with an organic base which provides a physiologically acceptable cation comprises both a salt formed by one molecule of the compound of formula (I) with one cation, but also a salt formed by a plurality of molecules of the compound of formula (I) with one cation, and a salt formed by one molecule of the compound of formula (I) with a plurality of cations.

As an example, the pharmaceutically acid addition salt of the compound of formula (I) has the structure as shown by the following formula (IA):

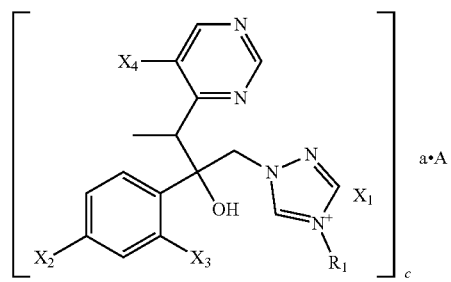

(IA)

wherein A represents an acid which forms an acid addition salt with the compound of formula (I), and for example, may be selected from an inorganic acid such as hydrochloric acid, hydrofluoric acid, hydrobromic acid, hydroiodic acid, sulfuric acid, pyrosulfuric acid, phosphoric acid or nitric acid; an organic acid such as formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectic acid, persulfate, 3-phenylpropane acid, picric acid, pivalic acid, 2-hydroxyethanesulfonic acid, itaconic acid, sulfamic acid, trifluoromethanesulfonic acid, lauryl sulfate, ethanesulfonic acid, benzenesulfonic acid, p-toluenesulfonic acid, sulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid or thiocyanic acid;

a represents the number of molecules of A, for example, may be selected from an integer of 1 or more, such as 1, 2, 3, 4 or 5;

c represents the number of molecules of the compound in the square bracket, that is, the compound of formula (I); for example, c may be selected from an integer of 1 or more, such as 1, 2, 3, 4 or 5;

provided that the product of the number of basic sites (such as N atoms) capable of being protonated in the compound of formula (I) and c=the product of the number of protons that A can ionize and a.

Preferably, wherein $X_1$ may be the same as or different from the anion formed by ionization of A; A is selected from the group consisting of hydrochloric acid, sulfuric acid, benzenesulfonic acid, p-toluenesulfonic acid, phosphoric acid, fumaric acid, citric acid, tartaric acid or lactic acid;

a is preferably 1, 2 or 3;

c is preferably 1, 2 or 3.

according to the present disclosure, when c>a in formula (IA), it means that a plurality of molecules of the compound of formula (I) forms a salt with one or more molecules of the acids represented by A; when c<a in formula (IA), it means that one or a plurality of the compound of formula (I) form a salt with a plurality of molecules of acids represented by A.

According to the present disclosure, preferably, the compound of formula (I) may have a structure represented by the following formula (I'):

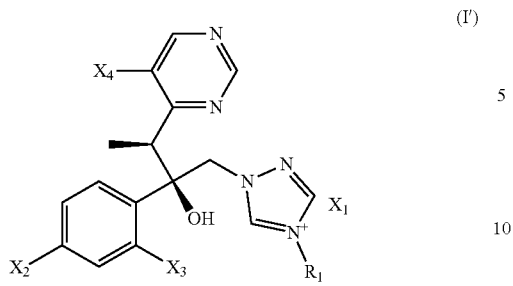
wherein each group has the definition described above.
As an example, the compound of formula (I) may be selected from the following exemplary compounds and a pharmaceutically acceptable salt thereof:
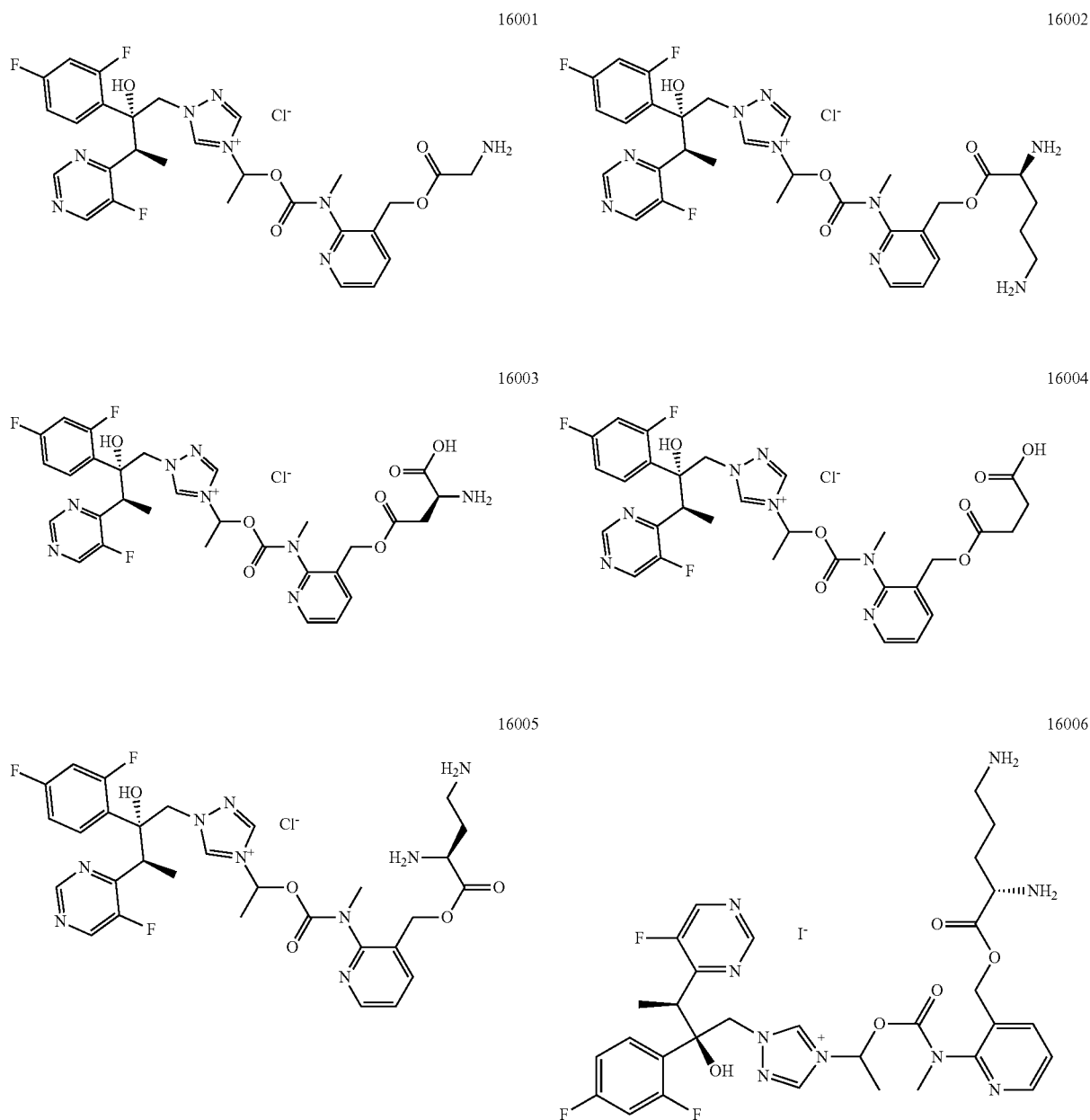

-continued
16007
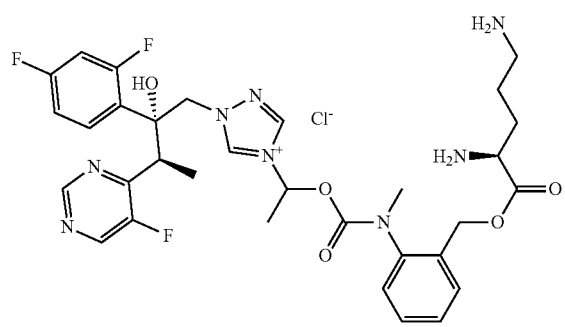
16008
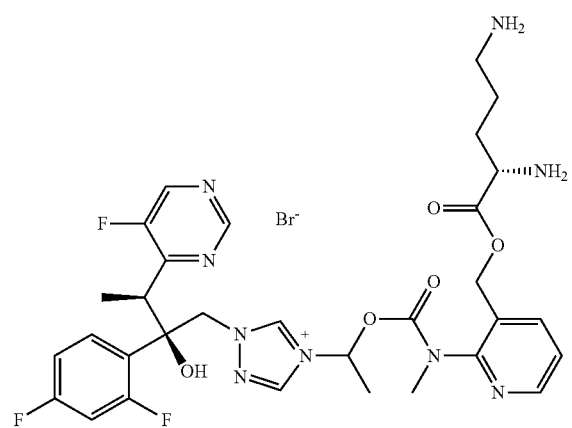
16009
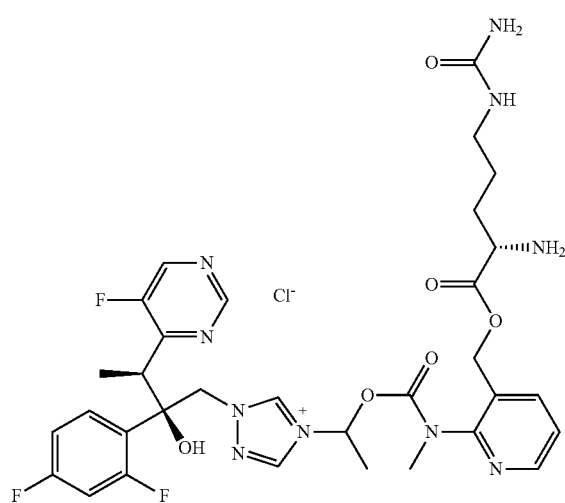
16010
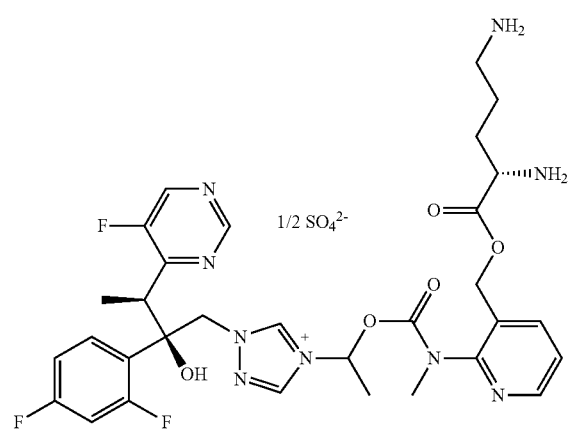
16011
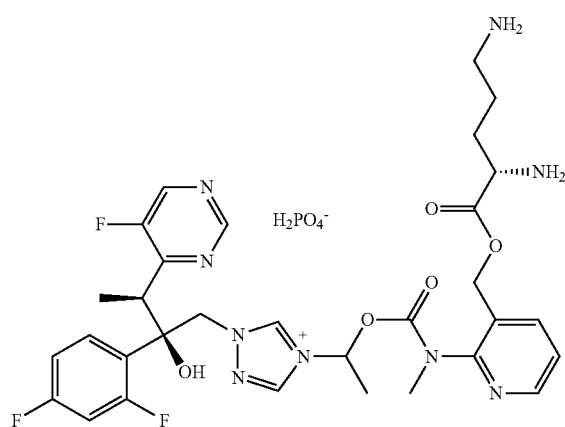
16012
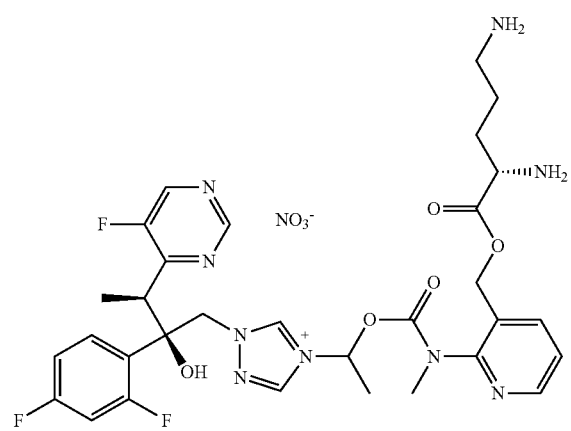

-continued
16013
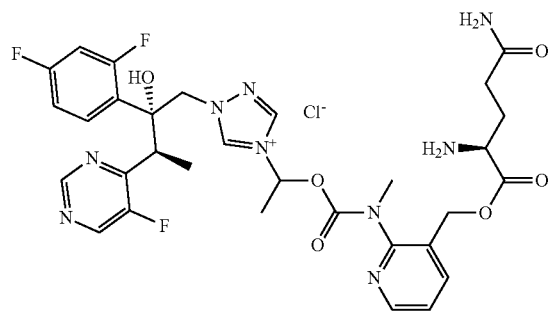
16014
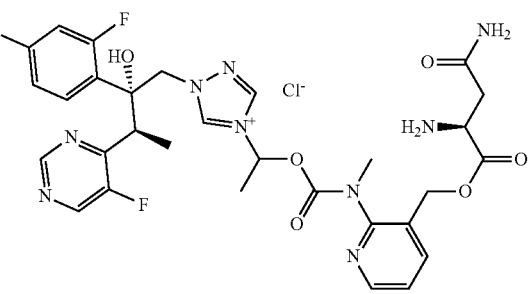
16015
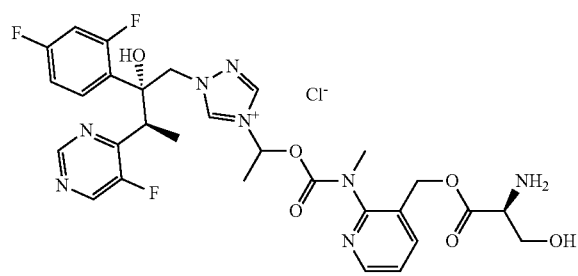
16016
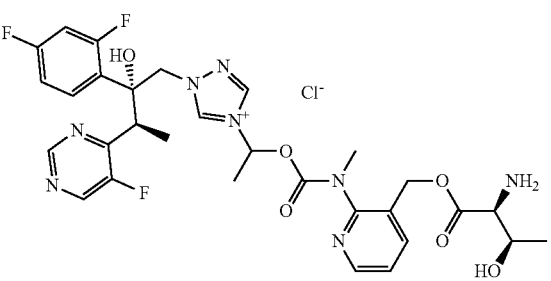
16017
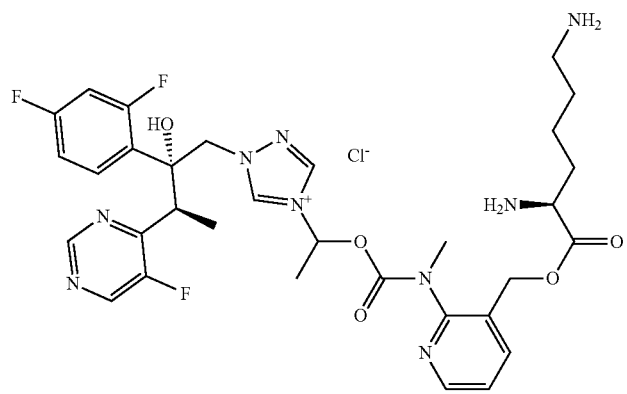
16018
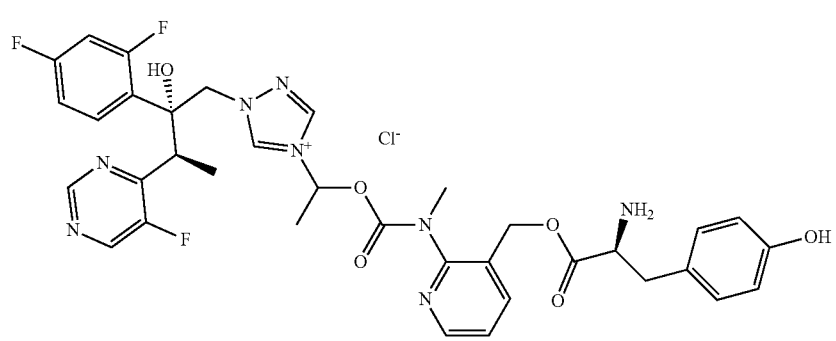

-continued
16019
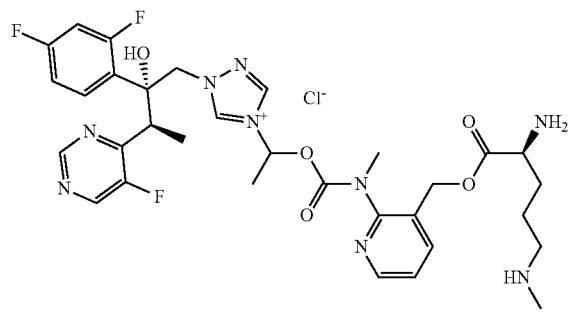
16020
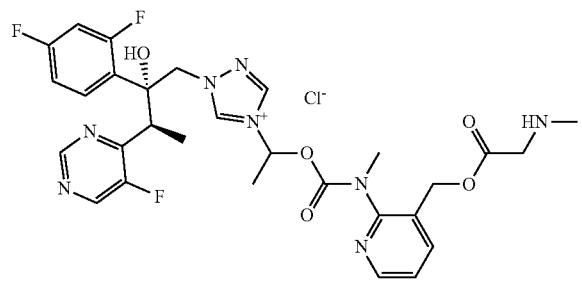
16021
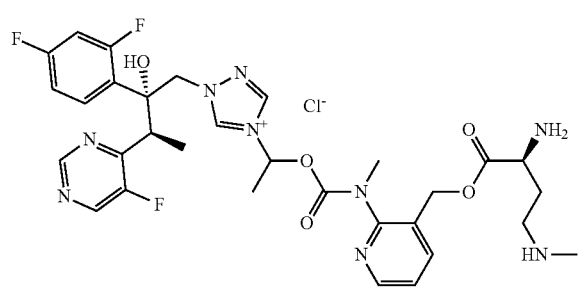
16022
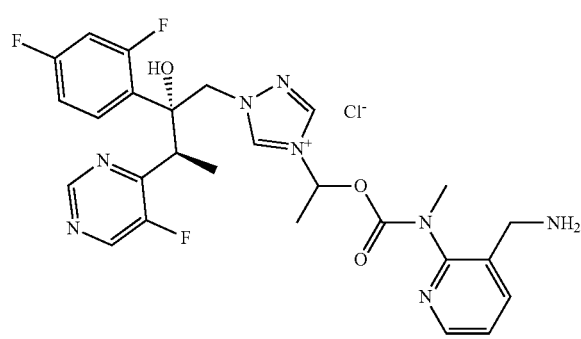
16023
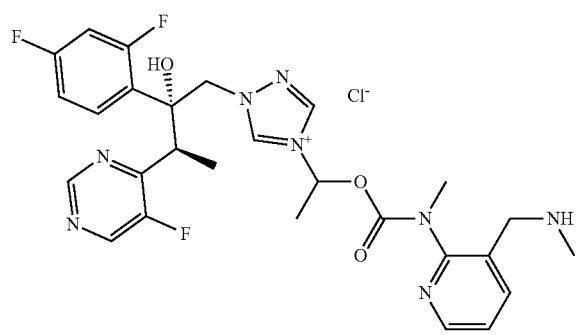
16024
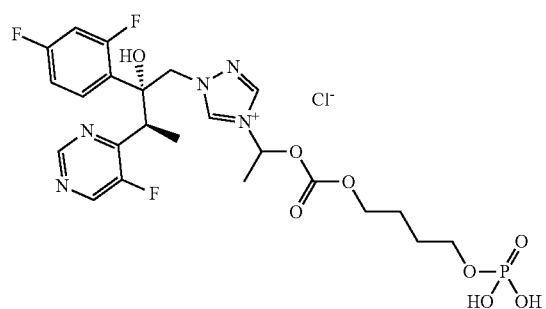
16025
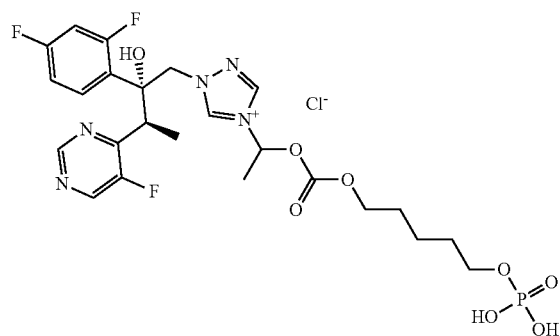
16026
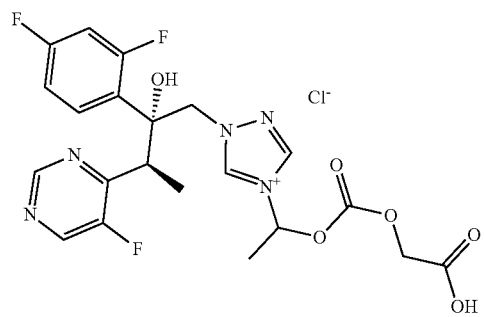

-continued
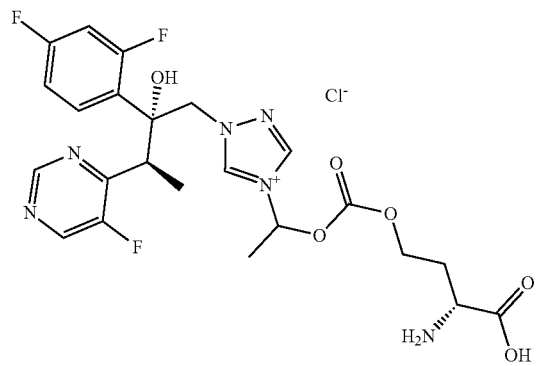
16027
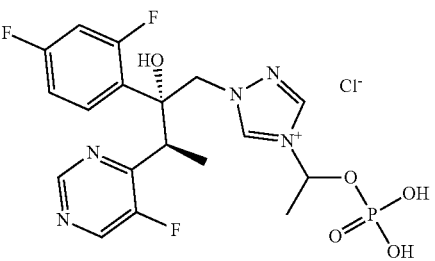
16028
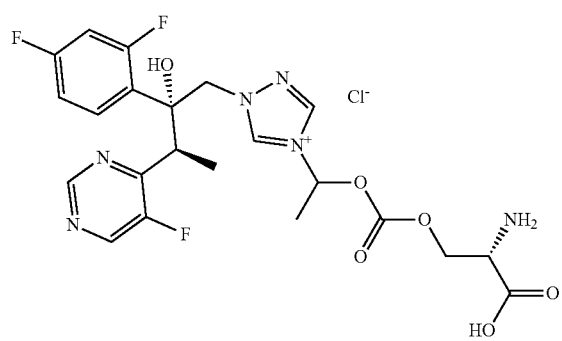
16029
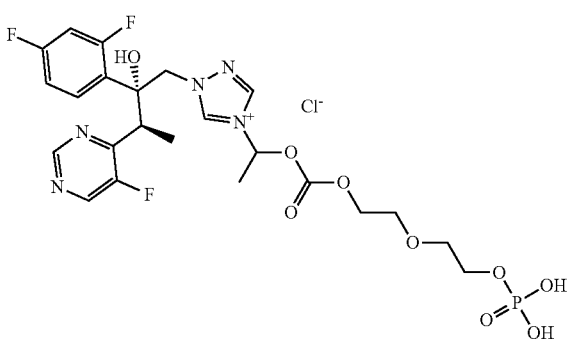
16030
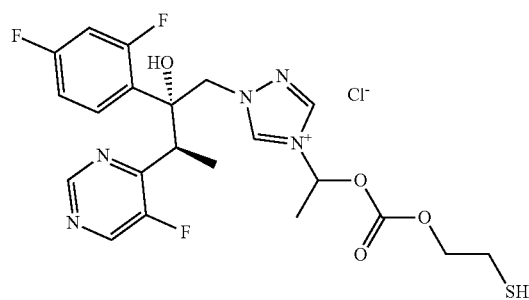
16031
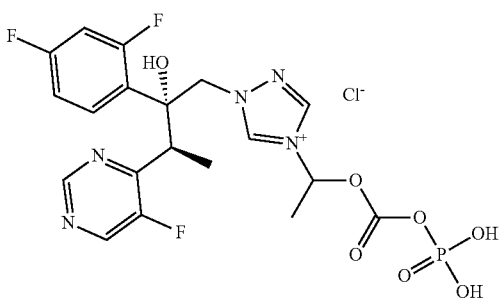
16032
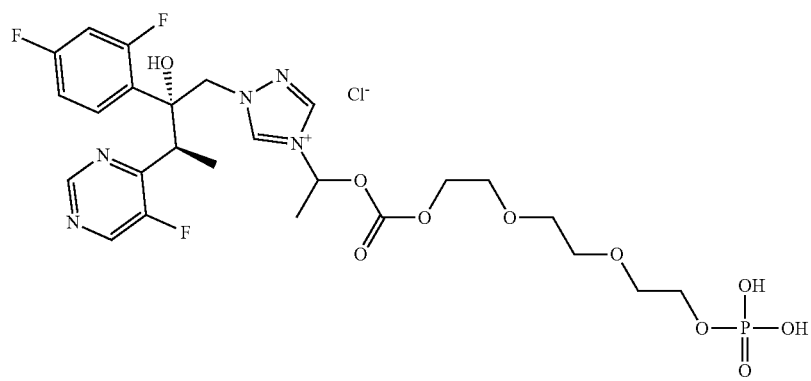
16033

-continued
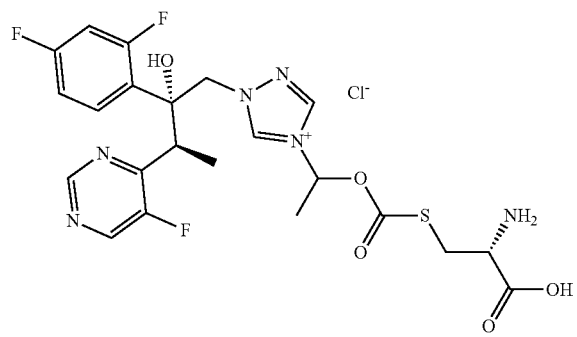
16034
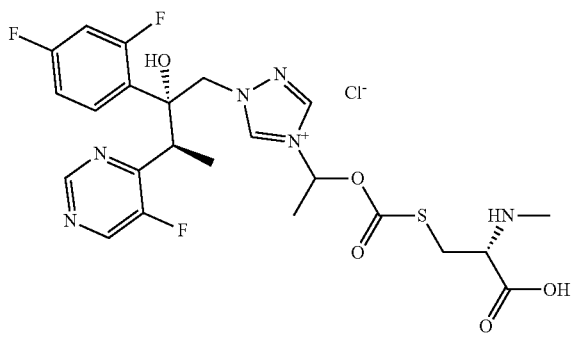
16035
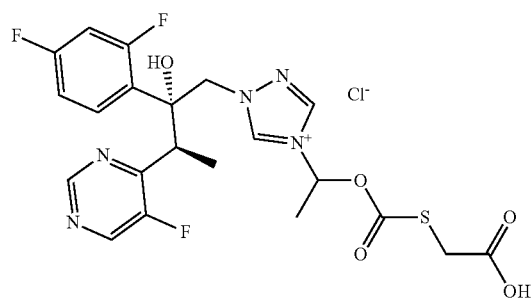
16036
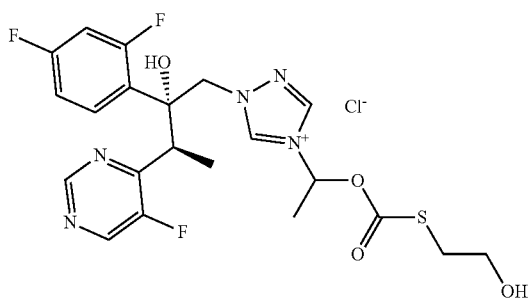
16037
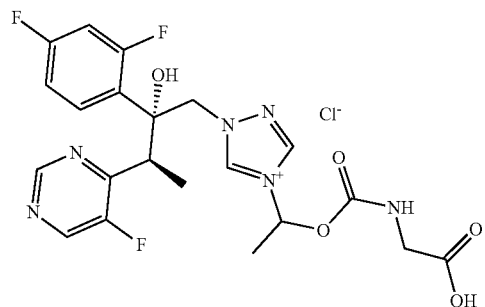
16038
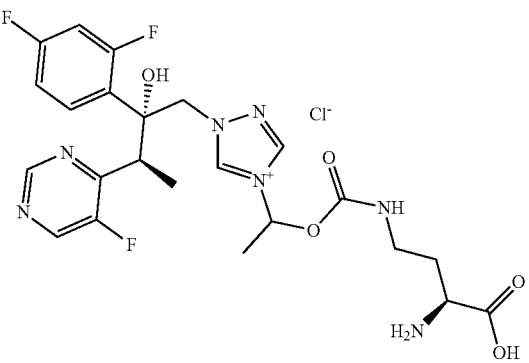
16039
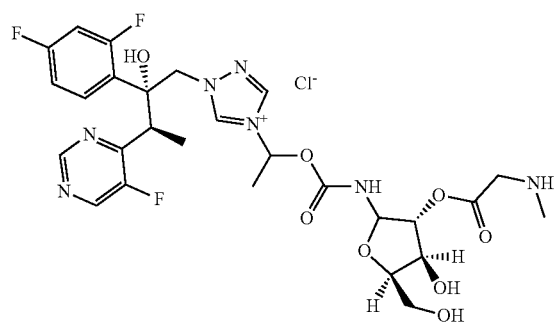
16040
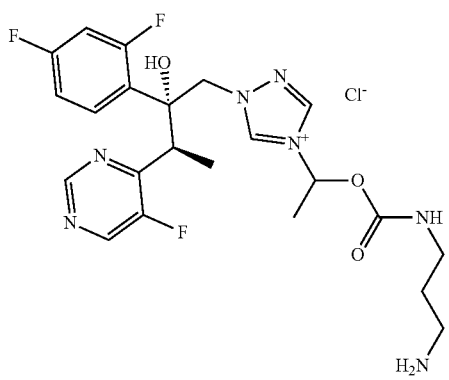
16041

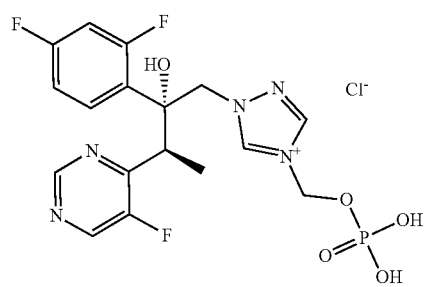
16042
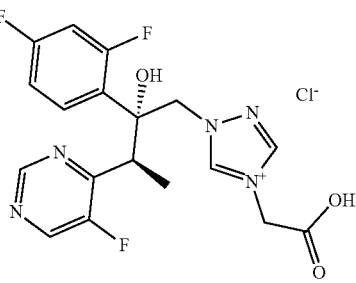
16043
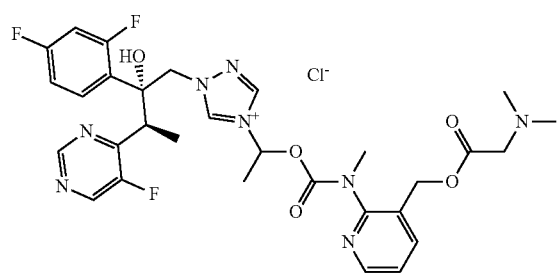
16045
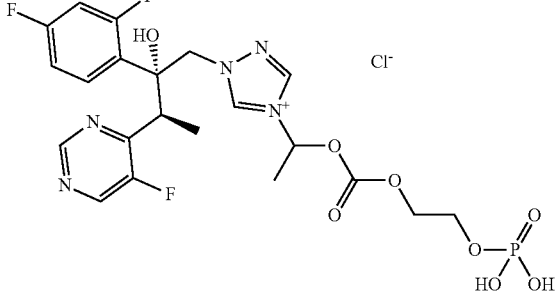
16046
The pharmaceutically acceptable salts of the compound of the present disclosure may be acidic or basic salts, and may be, for example, hydrochloride, sulfate, nitrate, phosphate salts, or salts formed with sodium ion, potassium ion, ammonium ion or the like. The salts can be as follows.
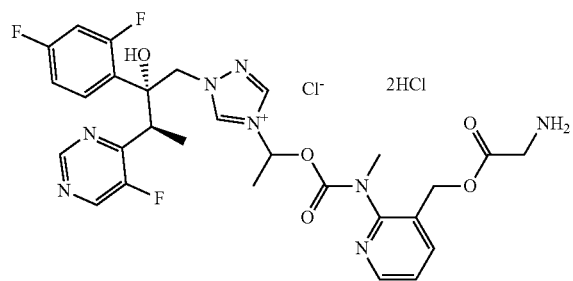
QR16001
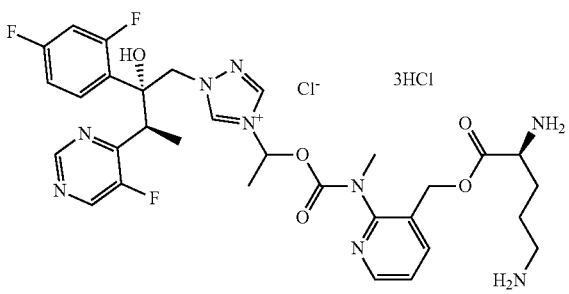
QR16002
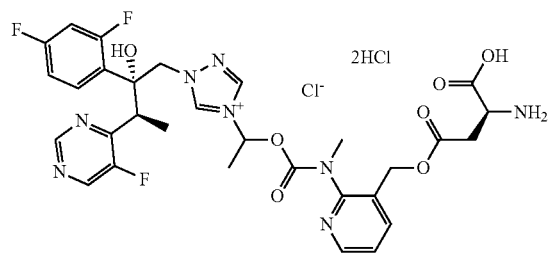
QR16003
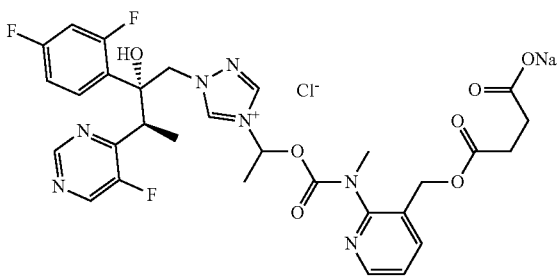
QR16004

-continued
QR16005
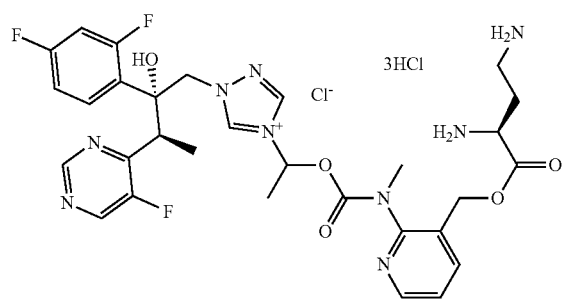
QR16006
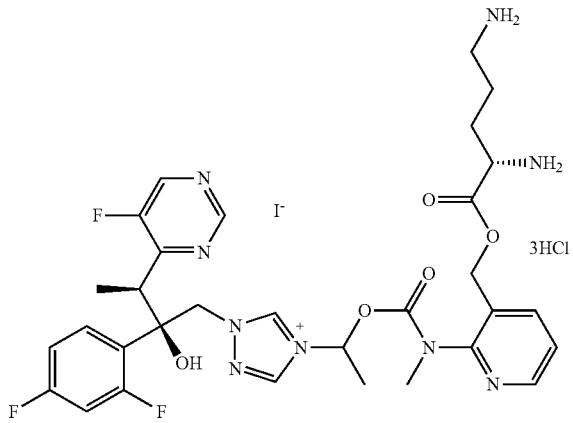
QR16007
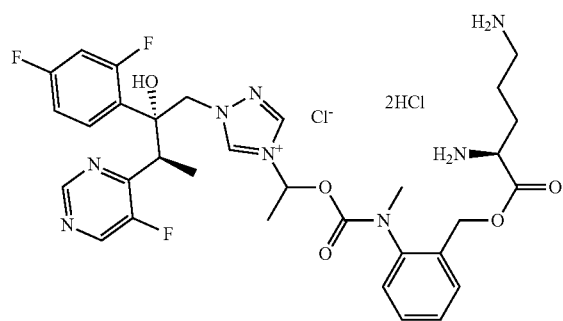
QR16008
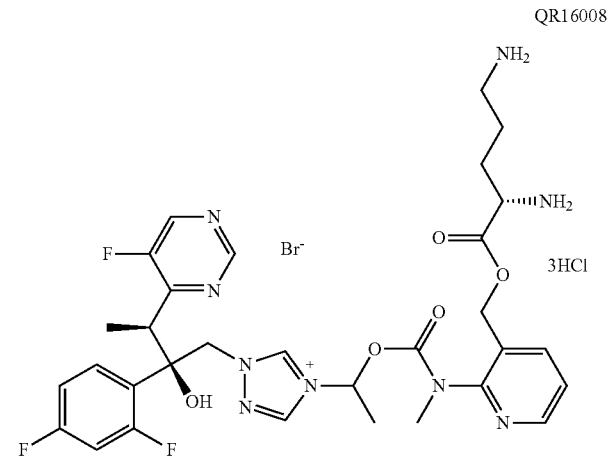
QR16009
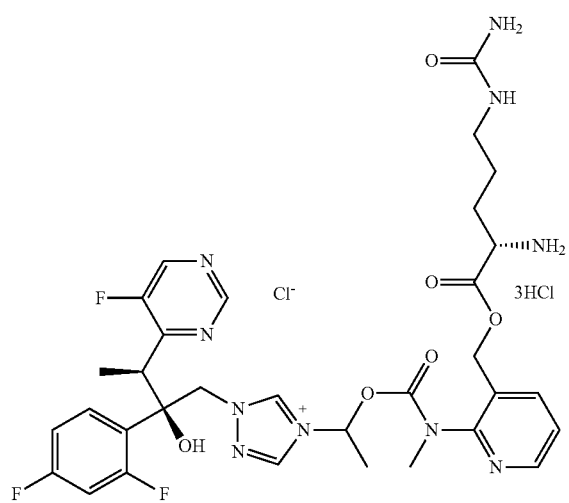
QR16011
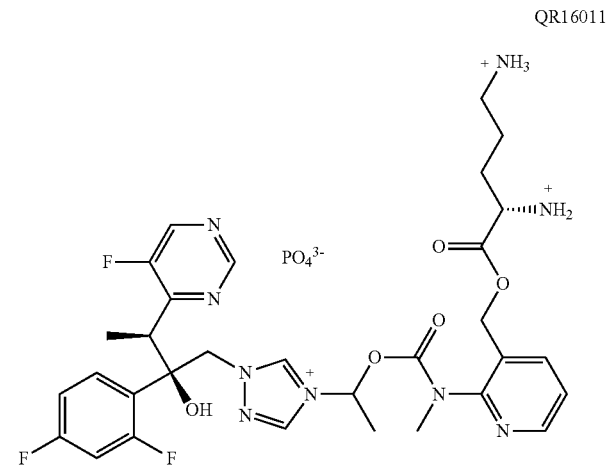

-continued
QR16012
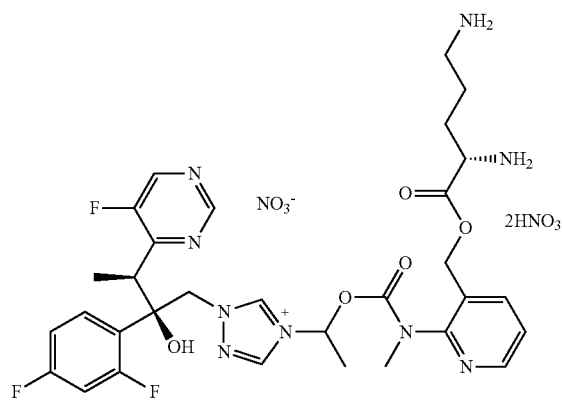
QR16013
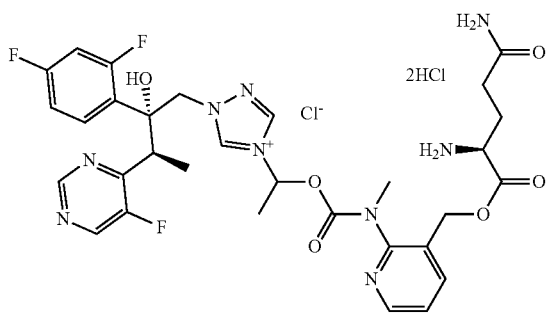
QR16014
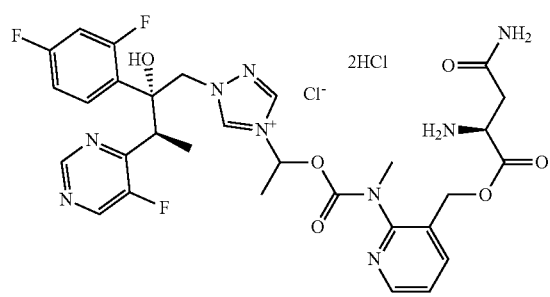
QR16015
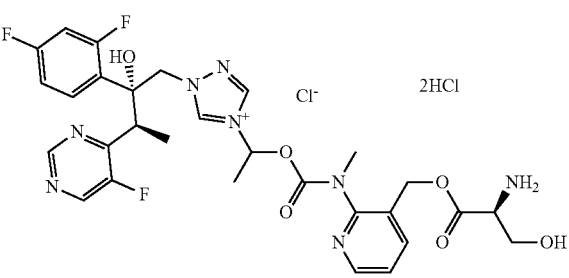
QR16016
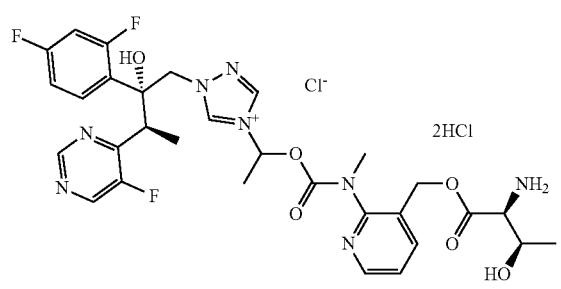
QR16017
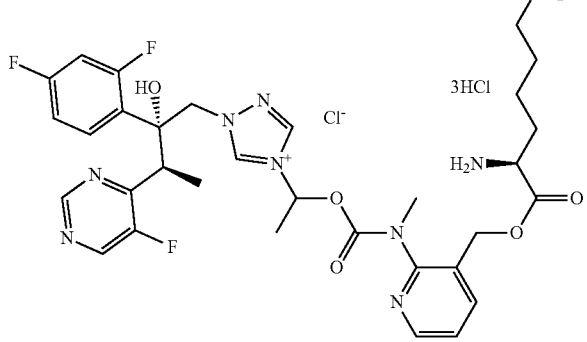
QR16018
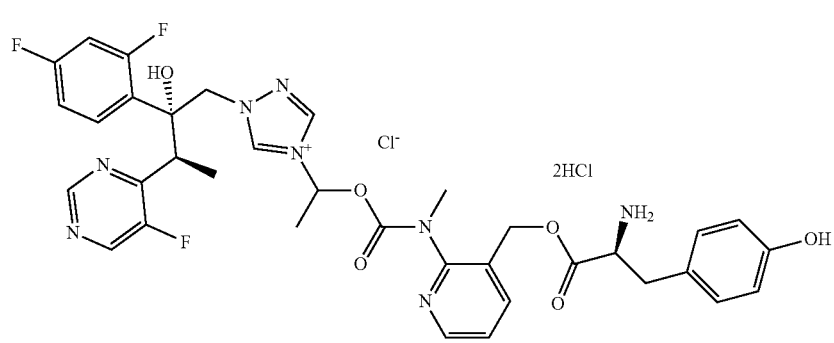

-continued
QR16019
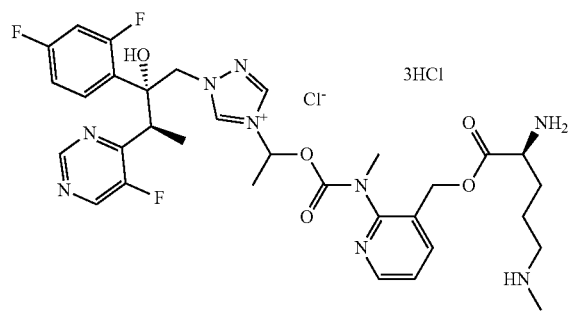
QR16020
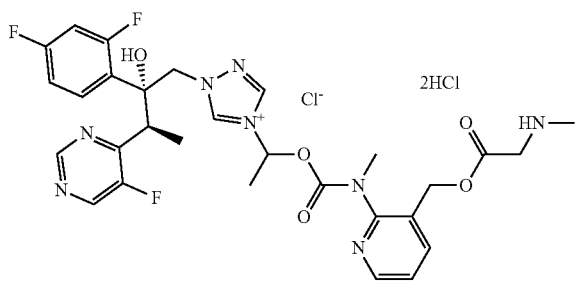
QR16021
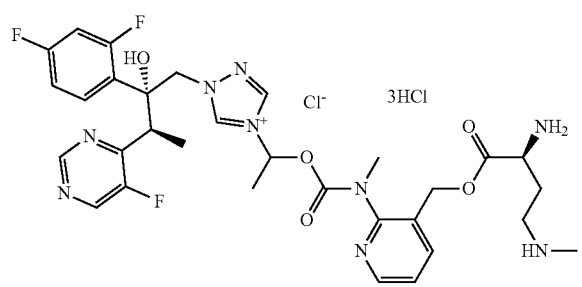
QR16022
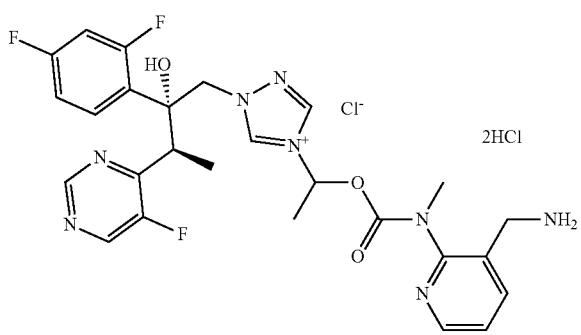
QR16023
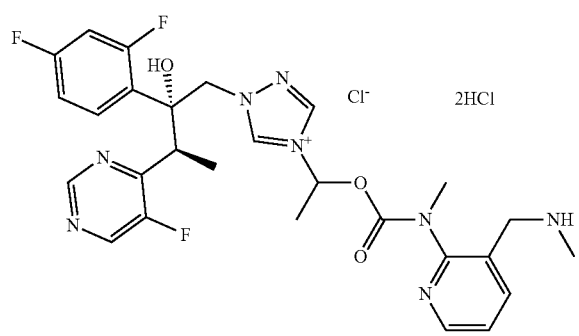
QR16024
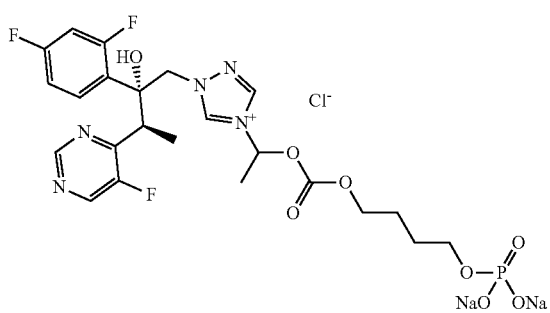
QR16025
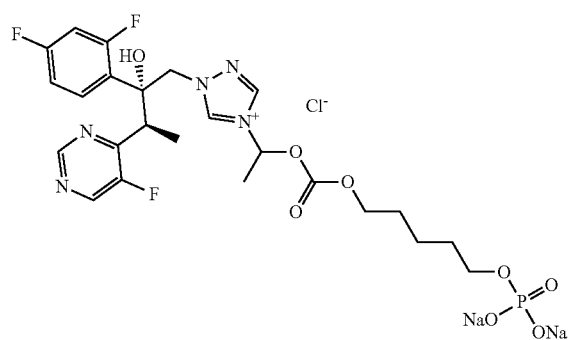
QR16026
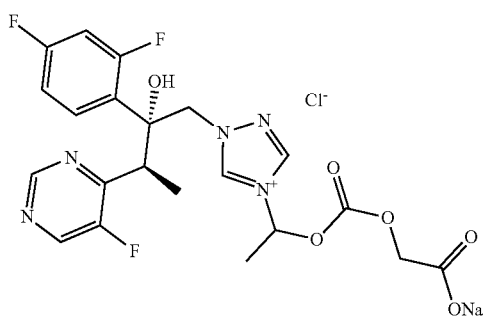

-continued
QR16027
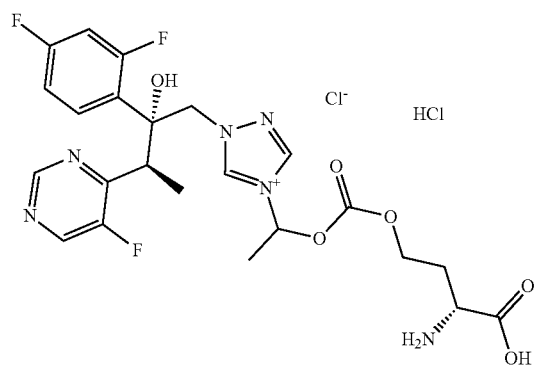
QR16028
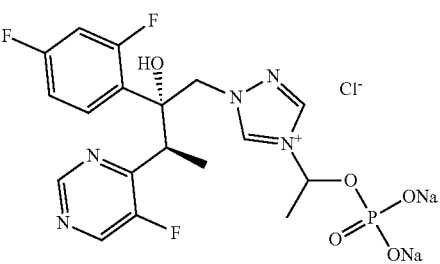
QR16029
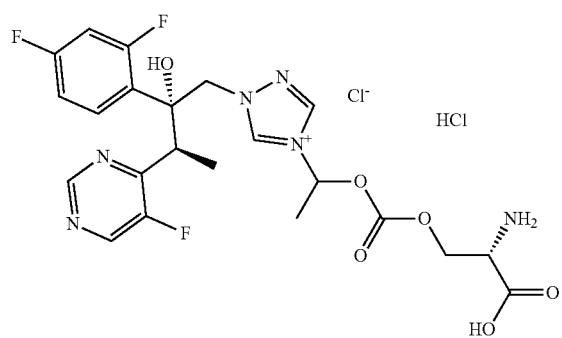
QR16030
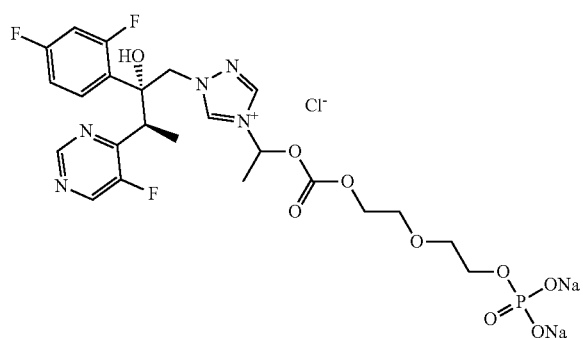
QR16032
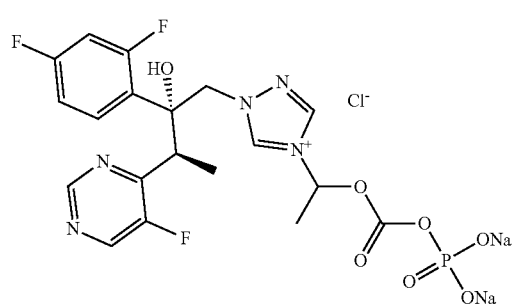
QR16033
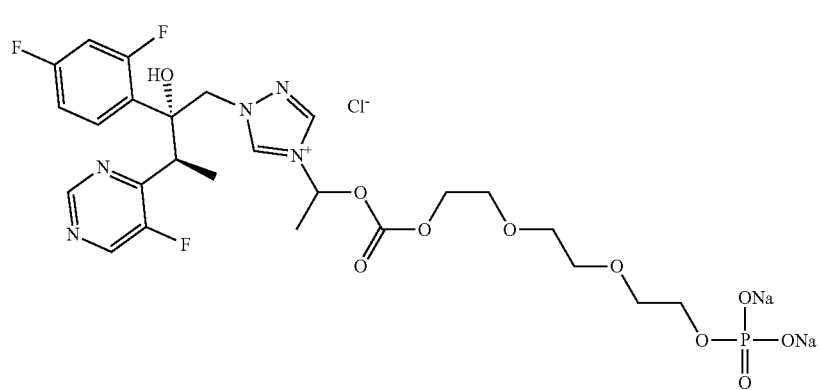

-continued
QR16034
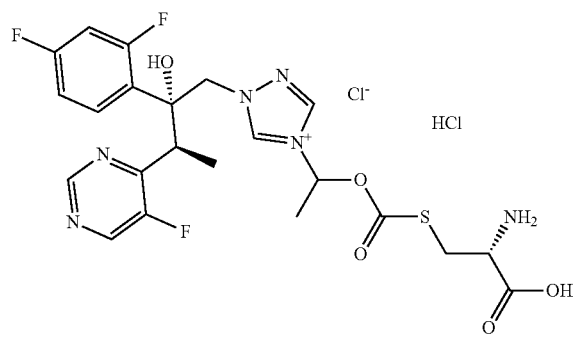
QR16035
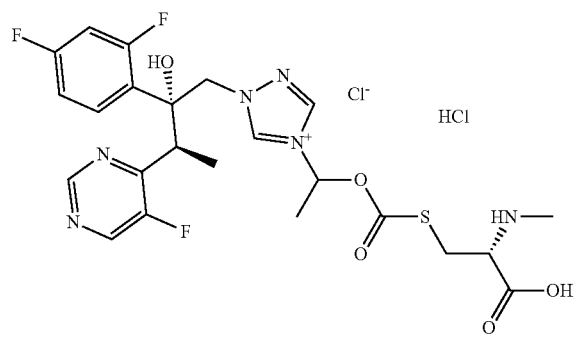
QR16036
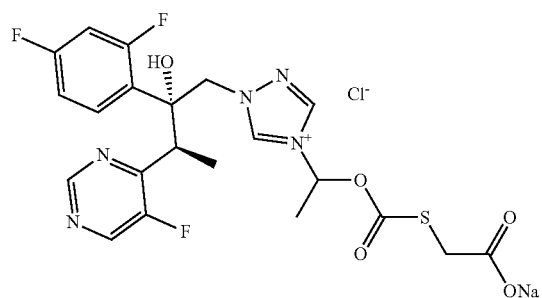
QR16038
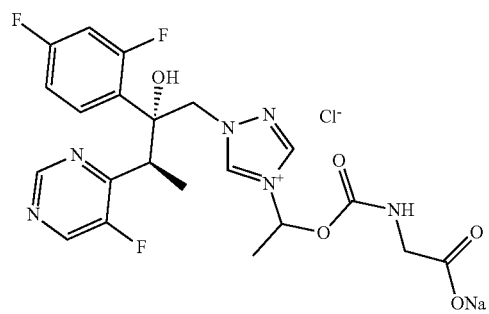
QR16039
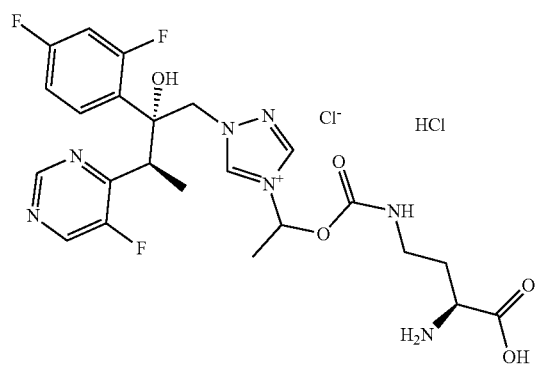
QR16040
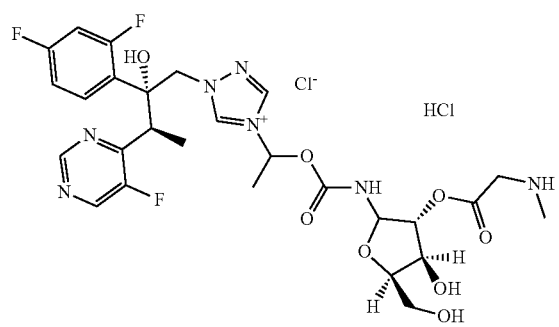
QR16041
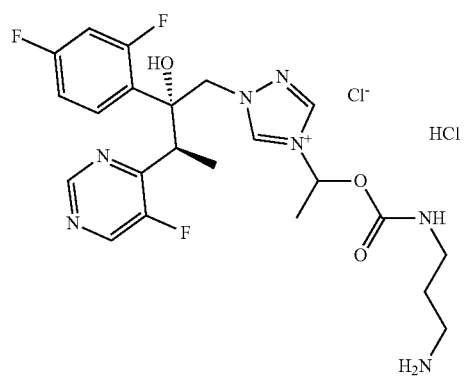
QR16042
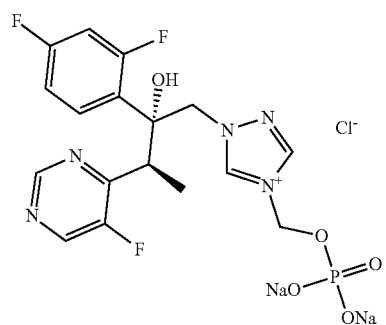

-continued
QR16043
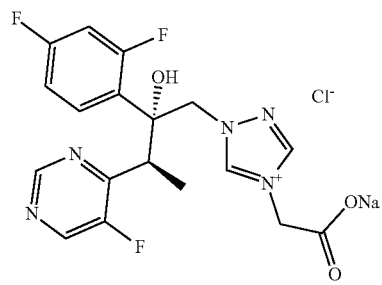
QR16045
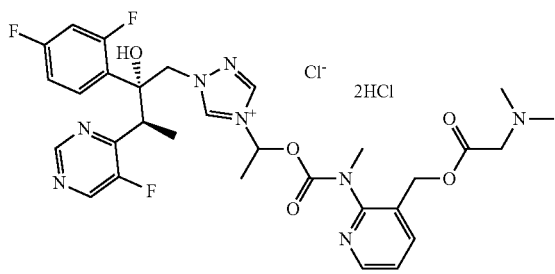
QR16046
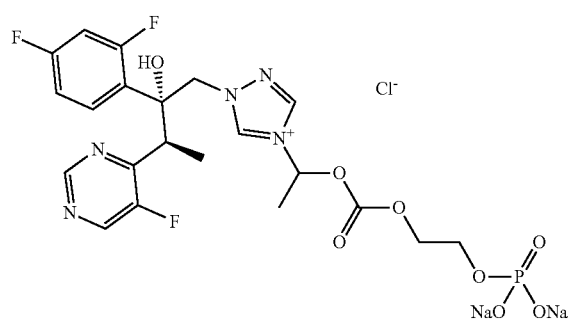
SF16001
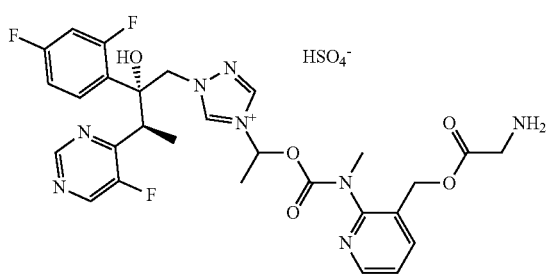
SF16002
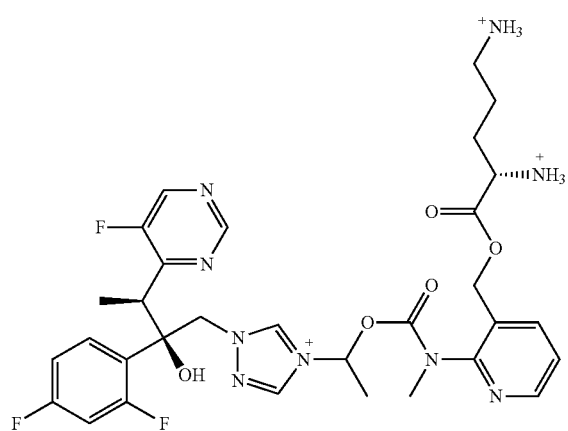
SF16020
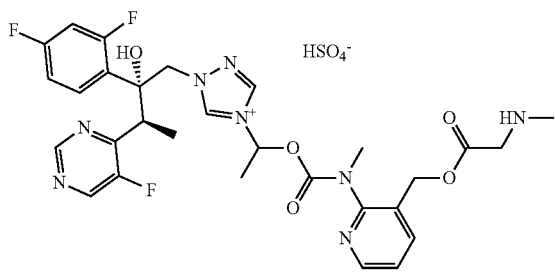
SF16013
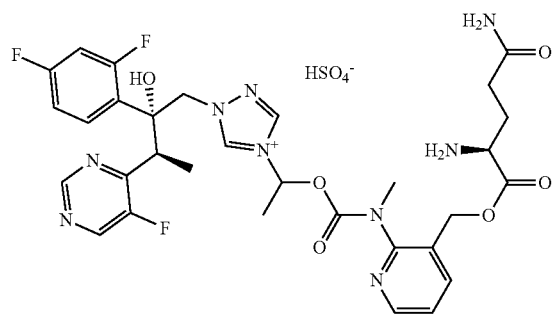
SF16014
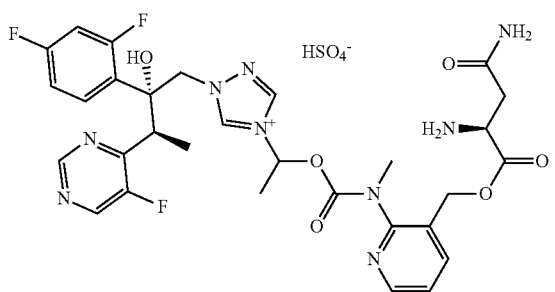

-continued

SF16015
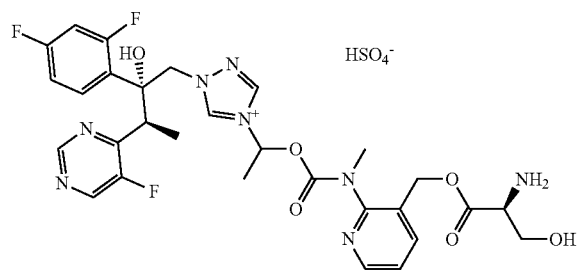

SF16016
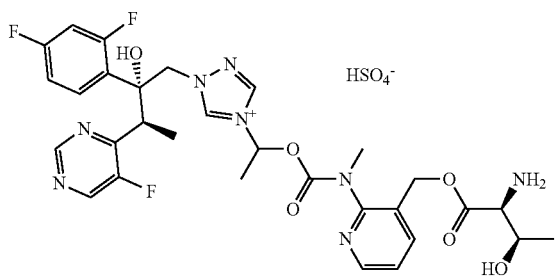

SF16017
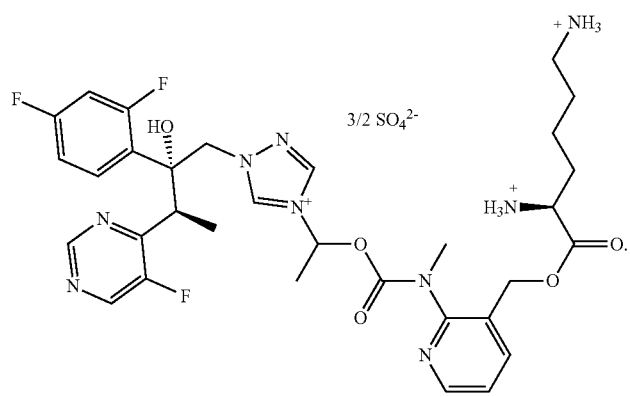

The present disclosure also provides a preparation method of the compound of formula (I), comprising preparing the compound of formula (I) by using the compound represented by the following formula (II) as a starting material:

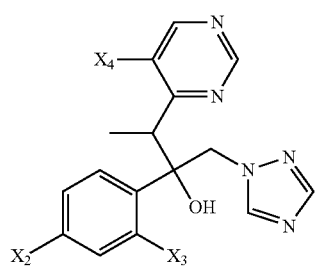

(II)

wherein, $X_2$, $X_3$ and $X_4$ have the definitions described above.

According to an embodiment of the present disclosure, for example, the compound represented by the following formula (II') can be used as a starting material to prepare the compound represented by the above formula (I'):

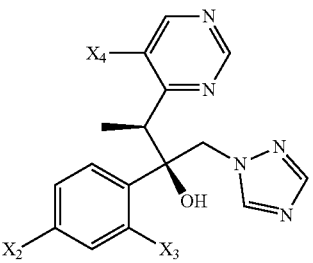

(II')

wherein, $X_2$, $X_3$ and $X_4$ have the definitions described above.

According to the preparation method of the present disclosure, a person skilled in the art can select an appropriate starting material to react with the compound of formula (II) to obtain the compound of formula (I). For example, an appropriate starting material can be reacted with the compound of formula (II') to provide the compound of formula (I').

According to an embodiment of the present disclosure, the preparation method may comprise, for example, reacting the compound of formula (II) with a compound of $R_z$-L, wherein $R_z$ is selected from $R_1$ or $R_1'$ which may be derivatized to $R_1$ having the definition described above, and L is a leaving group such as the group $X_1'$ which can be converted to $X_1$ in formula (I). For example, $R_z$-L may be selected from $R_1$-$X_1'$ or $R_1'$-$X_1'$.

As an example, $X_1'$ may be selected from the group consisting of Cl, Br or I.

For example, $X_1$ may be converted from L in $R_z$-L, or may be converted from an anion of another compound used in the reaction, such as an anion of a catalyst, or may be obtained by an optional salt-transforming step;

According to an embodiment of the invention, the preparation process can be carried out in the presence of a catalyst.

According to an embodiment of the present disclosure, the preparation method can be carried out in the absence of a solvent or in the presence of a solvent.

If necessary, one or more of the functional groups of the compound of formula (II) and/or compound of $R_z$-L may be protected with a protecting group (PG) and then the reaction is carried out. The functional group may be selected from, for example, one or more of amino, amine, hydroxyl, thiol, carboxyl, carbon-carbon double bond, and carbon-carbon triple bond. Each of the protecting groups (PG) may be selected, for example, from benzyloxycarbonyl (Cbz), tert-butoxycarbonyl (Boc), allyloxycarbonyl, trimethylsilyloxy-carbonyl (Teoc), methoxycarbonyl, ethoxycarbonyl, phthaloyl (pht), p-toluenesulfonyl (Ts), trifluoroacetyl (Tfa), pivaloyl, benzoyl, tritylmethyl (Trt), 2,4-dimethyl oxybenzyl (Dmb), p-methoxybenzyl (PMB), benzyl (Bn), tert-butyldimethylsilyl (TBS), trimethylsilyl (TMS), triisopropylsilane Base (TIPS—OR), tert-butyl (t-Bu).

If necessary, after completion of the reaction, the protecting group can be removed for subsequent reaction or to obtain the target compound.

According to the present disclosure, when $R_z$ is selected from $R_1'$, the $R_1'$ represents a group which can be further reacted to obtain $R_1$.

According to the present disclosure, preferably, the compound represented by the formula (II) or (II') as the substrate in the reaction does not undergo a configuration conversion.

It is to be understood that the formation of the pharmaceutically acceptable salt of the present disclosure can be carried out at the time of removing the protecting group, or the salt-forming and/or salt-transforming step can be carried out according to known methods.

The salt-transferring step can be carried out by a method of ion exchange.

According to an exemplary embodiment of the present disclosure, the preparation method comprises, but is not limited to, one or more of the following methods:

1) a hydroxymethyl-substituted arylamine or heteroarylamine is reacted with a desired acylating reagent under basic conditions to form the corresponding amide A-1, which is reacted with a carboxylic acid optionally containing a protecting group in the presence of a condensing agent to give compound A-2, and then the compound A-2 and the compound of formula (II') are reacted to obtain compound A-3, which is optionally deprotected to give compound A-4, and the compound A-4 may optionally be further subjected to a salt-forming and/or salt-transforming step:

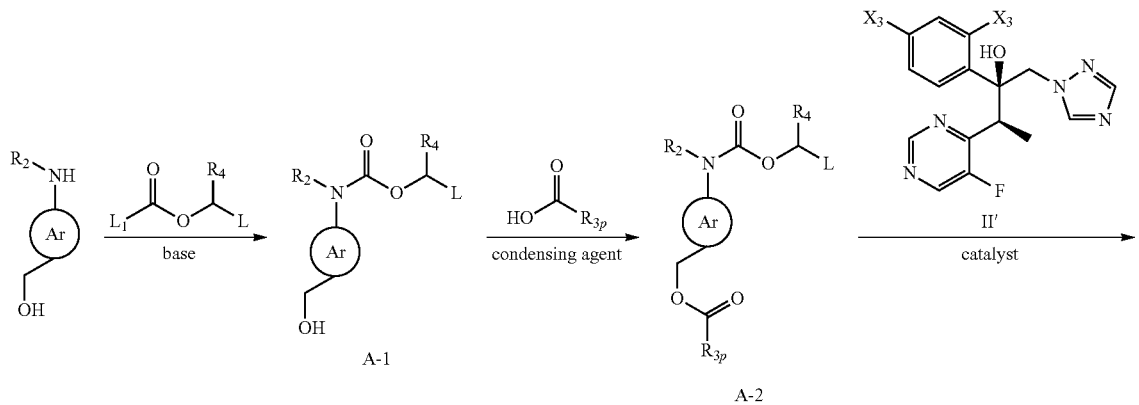

A-1

A-2

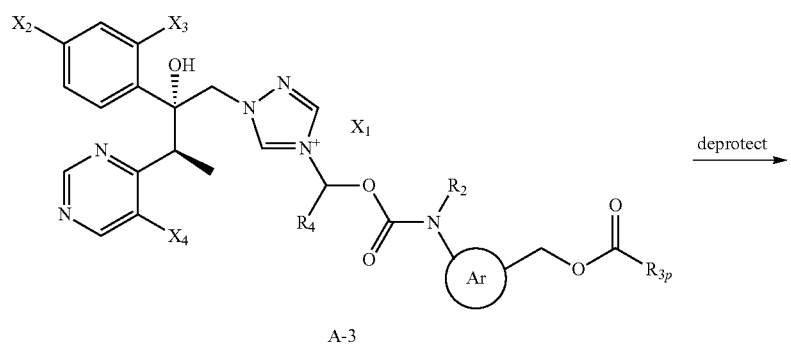

A-3

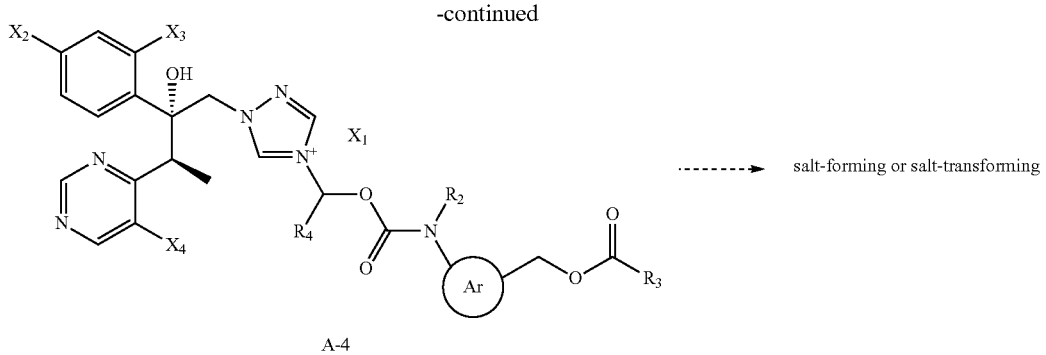

A-4 wherein, $L_1$ is a leaving group, such as a halogen, and may be selected from the group consisting of F, Cl, Br, and I;

$X_1$ is independently selected from a pharmaceutically acceptable anion; for example, $X_1$ may be converted from L of the compound A-2 or an anion of the catalyst, or may be obtained by an optional salt-transforming step;

$R_{3p}$ represents $R_3$ or —$R_3$—PG;

each of the other groups independently has the definition described above;

--------▶ represents a step optionally to be or not to be carried out;

2) a substituted alcohol, substituted amine or substituted thiol optionally containing a protecting group is reacted with an acylating reagent under basic conditions to form compound B-1, which is reacted with the compound of formula (II') to obtain compound B-2, and then the compound B-2 is optionally deprotected to give compound B-3, which may optionally be further subjected to a salt-forming and/or salt-transforming step:

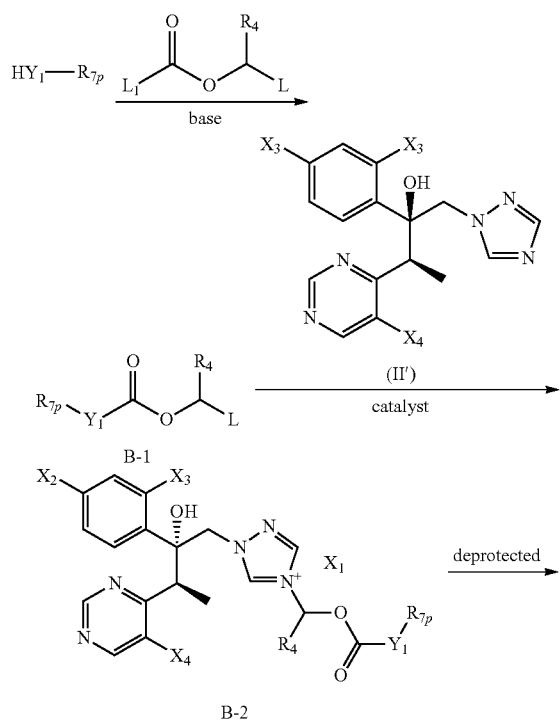

B-2

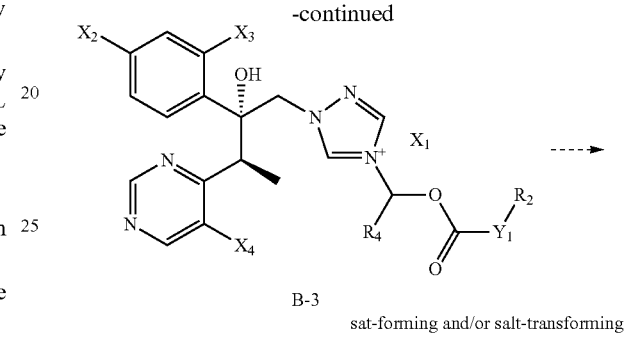

B-3 sat-forming and/or salt-transforming wherein $R_{7p}$ represents $R_7$ or —$R_7$—PG;

$X_1$ is independently selected from a pharmaceutically acceptable anion; for example, $X_1$ may be converted from L of the compound B-1 or an anion of the catalyst, or may be obtained by an optional salt-transforming step;

each of the other groups independently has the definition described above;

▶ represents a step optionally to be or not to be carried out;

3) a diol as a starting material is reacted with phosphorus oxychloride di-tert-butyl ester (CAS No. 56119-60-9) under basic conditions to form compound C-1, which is then acylated to obtain compound C-2, and the compound C-2 is reacted with the compound of formula (II') to give compound C-3; and the compound C-3 is deprotected to give compound C-4, which may optionally be further subjected to a salt-forming and/or salt-transforming step:

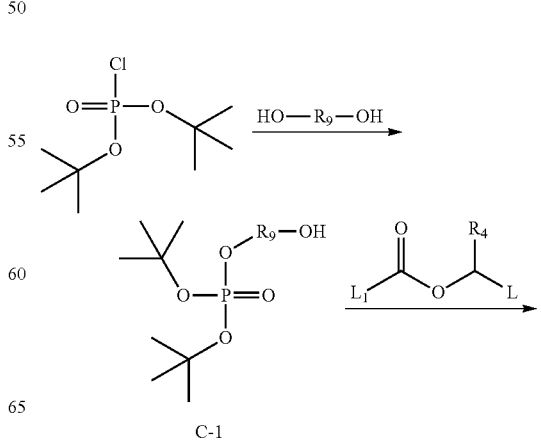

C-1

41

-continued

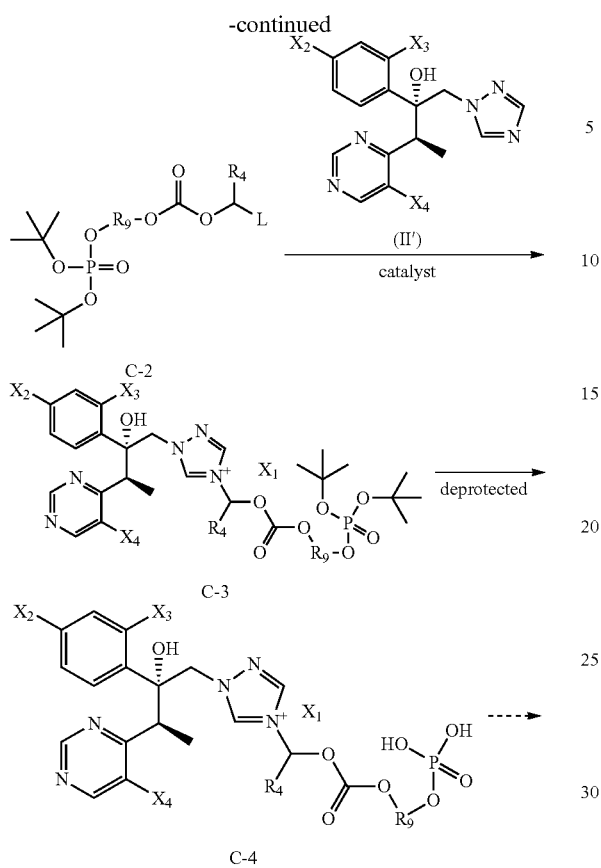

C-2

C-3

C-4 salt-forming and/or salt-transforming wherein $R_9$ is $(CH_2)_h$, and h is an integer of 1 to 12, for example, may be 1, 2, 3, 4, 5 or 6;

or $R_9$ is $[(CH_2)_2O]_x(CH_2)_y$, and x, y are independently selected from an integer of 1 to 12, for example, x, y are independently selected from 1, 2 or 3;

$X_1$ is independently selected from a pharmaceutically acceptable anion; for example, $X_1$ may be converted from L of the compound C-2 or an anion of the catalyst, or may be obtained by an optional salt-transforming step;

each of the other groups independently has the definition described above;

▸ represents a step optionally to be or not to be carried out;

4) the starting material D-1 is reacted with an iodoalkane to form compound D-2, and the compound D-2 is reacted with the compound represented by formula (II') to obtain compound D-3, which is deprotected under acidic conditions to give compound D-4, and the compound D-4 may optionally be further subjected to a salt-forming and/or salt-transforming step:

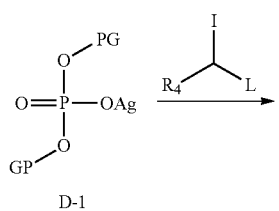

D-1

42

-continued

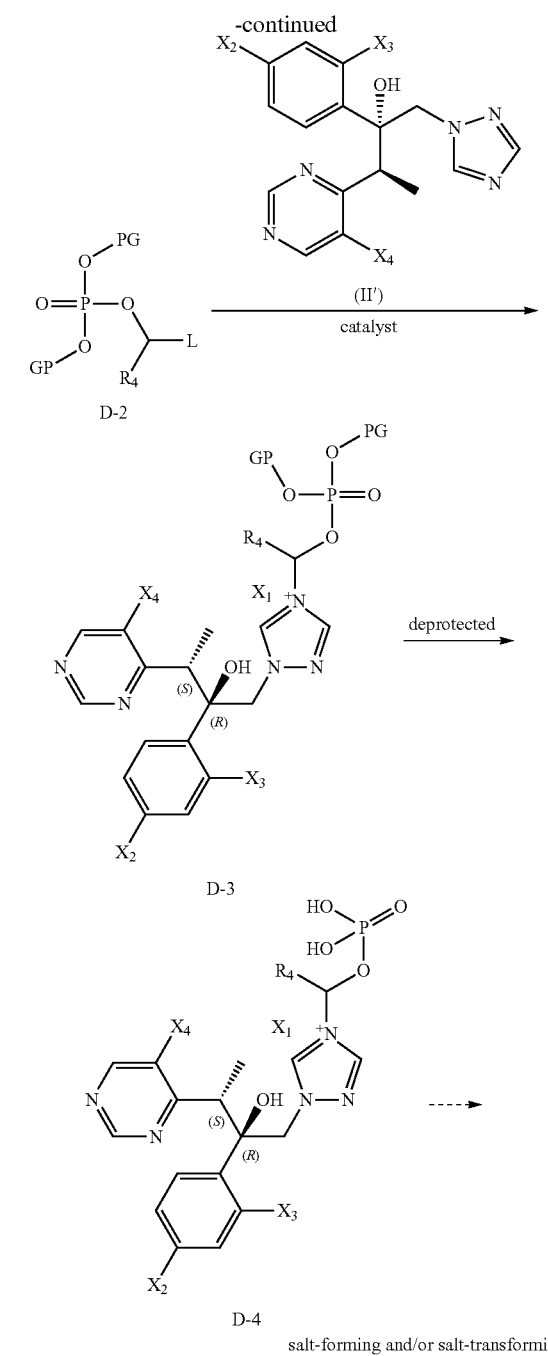

D-2

D-3

D-4 salt-forming and/or salt-transforming wherein $X_1$ is independently selected from a pharmaceutically acceptable anion; for example, $X_1$ may be converted from L of the compound D-2 or an anion of the catalyst, or may be obtained by an optional salt-transforming step;

each of the other groups independently has the definition described above;

------▸ represents a step optionally to be or not to be carried out;

5) the compound represented by the formula (II') is reacted with a chloroacetic acid ester reagent to obtain compound E-1, which is further subjected to a hydrolysis reaction to obtain compound E-2, and the compound E-2 may optionally be further subjected to a salt-forming and/or salt-transforming step:

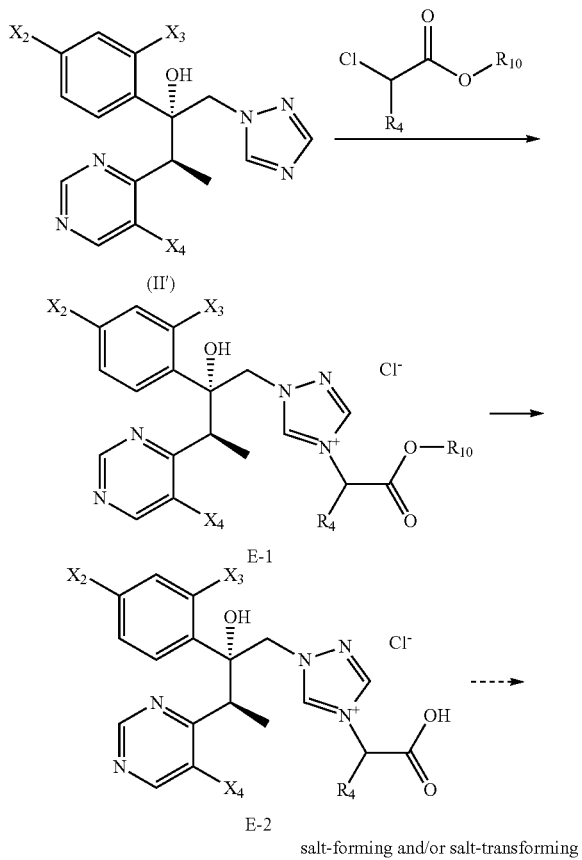

salt-forming and/or salt-transforming wherein, each of the other groups independently has the definition described above;

$R_{10}$ is preferably methyl, ethyl, isopropyl or t-butyl;

▸ represents a step optionally to be or not to be carried out.

Alternatively, if appropriate, the preparation method of the present disclosure also comprises an embodiment in which the reaction is carried out in when the reaction substrate is unprotected by the protecting group PG. It will be understood by those skilled in the art that in such cases, the deprotecting step is not required correspondingly.

It will be understood by those skilled in the art that the compound represented by the formula (I) and the racemate, stereoisomer, tautomer, oxynitride thereof can be used as a raw material or an intermediate to prepare pharmaceutically acceptable salts of the compound of formula (I) and the racemate, stereoisomer, tautomer, oxynitride thereof. Accordingly, the present disclosure also provides the use of the compound represented by the formula (I), the racemate, stereoisomer, tautomer, oxynitride thereof in the preparation of pharmaceutically acceptable salts of the compound represented by the formula (I), and the racemate, stereoisomer, tautomer, oxynitride thereof.

The present disclosure also provides a pharmaceutical composition comprising a therapeutically effective amount of the compound of the present disclosure (comprising the compound of formula (I), a racemate, stereoisomer, tautomer, oxynitride or pharmaceutically acceptable salt thereof). The pharmaceutical composition may also optionally comprise a pharmaceutically acceptable auxiliary material, such as a carrier, excipient. As an example, the auxiliary material may be one or more selected from the group consisting of a disintegrant, a glidant, a lubricant, a diluent or a filler, a binder and a colorant.

The present disclosure also provides the use of the compound represented by the formula (I), the racemate, stereoisomer, tautomer, oxynitride and pharmaceutically acceptable salt thereof in the preparation of antimicrobial, particularly in antifungal (including but not limited to, *Candida albicans, Aspergillus fumigatus*) drugs.

The present disclosure also provides the use of compounds comprising the compound represented by the formula (I), the racemate, stereoisomer, tautomer, oxynitride and pharmaceutically acceptable salt thereof for preventing or treating diseases, such as diseases caused by fungi (including, but not limited to, *Candida albicans, Aspergillus fumigatus*).

Term Definition and Description

Unless otherwise stated, the definitions of groups and terms recited in the specification and claims of the present application include their definitions as embodiments, exemplary definitions, preferred definitions, definitions in the tables, and definitions of specific compounds in the examples, etc., and any combination and incorporation thereof. Such combinations and incorporations of group definitions as well as compound structures are intended to fall within the scope of the specification.

When the numerical range set forth in the specification and the claims is defined as "integer", it should be understood that the two endpoints of the range and each integer within the range are recited. For example, "an integer of 0 to 10" should be understood to mean each integer of 0, 1, 2, 3, 4, 5, 6, 7, 8, 9, and 10. When the numerical range is defined as a "number", it is to be understood that the two endpoints of the range, each integer in the range, and each fraction in the range are recited. For example, "a number of 0 to 10" should be understood to mean not only each integer of 0, 1, 2, 3, 4, 5, 6, 7, 8, 9, and 10 but also at least the sum of each integer added with 0.1, 0.2, 0.3, 0.4, 0.5, 0.6, 0.7, 0.8, 0.9 respectively. Unless otherwise stated, when "the compound of the present disclosure" is used herein, it is intended to encompass the triazole derivative represented by the formula (I), the racemate, stereoisomer, tautomer, oxynitride and pharmaceutically acceptable salts thereof.

The term "halogen" refers to F, Cl, Br and I. In other words, F, Cl, Br, and I can be described as "halogen" in this specification.

The term "$C_{1-40}$ alkyl" is understood to preferably denote a straight or branched saturated monovalent hydrocarbon radical having from 1 to 40 carbon atoms, preferably $C_{1-10}$ alkyl. "$C_{1-10}$ alkyl" is understood to preferably denote a straight or branched saturated monovalent hydrocarbon radical having 1, 2, 3, 4, 5, 6, 7, 8, 9 or 10 carbon atoms. The alkyl group is, for example, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl, or the like, or isomers thereof. In particular, the group has 1, 2, 3, 4, 5 or 6 carbon atoms ("$C_{1-6}$ alkyl"), such as methyl, ethyl, propyl, butyl, isopropyl, isobutyl, sec-butyl, tert-butyl, and more particularly, the group has 1, 2 or 3 carbon atoms ("$C_{1-3}$ alkyl"), such as methyl, ethyl, n-propyl or isopropyl.

The term "$C_{2-40}$ alkenyl" is understood to preferably denote a straight or branched monovalent hydrocarbon radical which contains one or more double bonds and has 2 to 40 carbon atoms, preferably "$C_{210}$ alkenyl". "$C_{210}$ alkenyl" is understood to preferably denote a straight or branched monovalent hydrocarbon radical comprising one or more double bonds and having 2, 3, 4, 5, 6, 7, 8, 9 or 10 carbon atoms, especially 2 or 3 carbon atoms ("$C_{23}$ alkenyl"), and it is understood that where the alkenyl group contains more than one double bond, the double bonds may be separated or conjugated to each other. The alkenyl group is, for example, vinyl, allyl, (E)-2-methylvinyl, (Z)-2-methylvinyl, (E)-but-2-alkenyl, (Z)-But-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-ene, hex-5-alkenyl, (E)-hex-4-enyl, (Z)-hex-4-enyl, (E)-hex-3-enyl, (Z)-hex-3-Alkenyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbutyl-2-alkenyl, (E)-2-methylbut-2-enyl, (Z)-2-methylbut-2-enyl, (E)-1-methylbut-2-alkenyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-iso propyl vinyl.

The term "$C_{2-40}$ alkynyl" is understood to mean a straight or branched monovalent hydrocarbon radical which contains one or more triple bonds and has 2 to 40 carbon atoms, preferably "$C_2$-$C_{10}$ alkynyl". The term "$C_2$-$C_{10}$ alkynyl" is understood to preferably denote a straight or branched monovalent hydrocarbon radical which contains one or more triple bonds and has 2, 3, 4, 5, 6, 7, 8, 9 or 10 carbon atoms, especially 2 or 3 carbon atoms ("$C_2$-$C_3$-alkynyl"). The alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, Hex-5-alkynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpentyl 4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbutyl-2-Alkynyl, 1-propylprop-2-ynyl, 1-isopropylpropan-2-ynyl, 2,2-dimethylbut-3-ynyl, 1,1-dimethylbutyl 3-ynyl, 1,1-dimethylbut-2-ynyl or 3,3-dimethylbut-1-ynyl. In particular, the alkynyl group is ethynyl, prop-1-ynyl or prop-2-ynyl.

The term "$C_{3-20}$ cycloalkyl" is understood to mean a saturated monovalent monocyclic or bicyclic hydrocarbon ring having from 3 to 20 carbon atoms, preferably "$C_{3-10}$ cycloalkyl". The term "$C_{3-10}$ cycloalkyl" is understood to mean a saturated monovalent monocyclic or bicyclic hydrocarbon ring having 3, 4, 5, 6, 7, 8, 9 or 10 carbon atoms. The $C_{3-10}$ cycloalkyl group may be a monocyclic hydrocarbon group such as cyclopropyl, cyclobutyl, cyclopentyl, cyclohexyl, cycloheptyl, cyclooctyl, cyclononyl, cyclodecyl, or a bicyclic hydrocarbon group such as decalin ring group.

The term "3-20 membered heterocyclyl" means a saturated monovalent monocyclic or bicyclic hydrocarbon ring comprising from 1 to 5 heteroatoms independently selected from N, O and S, preferably "3-10 membered heterocyclyl". The term "3-10 membered heterocyclyl" means a saturated monovalent monocyclic or bicyclic hydrocarbon ring containing from 1 to 5, preferably from 1 to 3 heteroatoms selected from N, O and S. The heterocyclyl can be attached to the remainder of the molecule by any one of the carbon atoms or a nitrogen atom (if present). In particular, the heterocyclyl may include, but not limited to: a 4-membered ring such as azetidinyl, oxetanyl; a 5-membered ring such as tetrahydrofuranyl, dioxolyl, pyrrolidyl, imidazolidinyl, pyrazolidinyl, pyrrolinyl; or 6-membered ring, such as tetrahydropyranyl, piperidinyl, morpholinyl, dithianyl, thiomorpholinyl, piperazinyl, trithianyl; or a 7-membered ring such as a diazepanyl group. Optionally, the heterocyclyl can be benzo fused. The heterocyclyl may be bicyclic, such as, but not limited to, a 5,5-membered ring such as a hexahydrocyclopenta[c]pyrrole-2(1H)-yl ring, or a 5,6-membered bicyclic ring such as hexahydropyrrolo[1,2-a]pyrazine-2 (1H)-yl ring. The ring containing a nitrogen atom may be partially unsaturated, that is, it may contain one or more double bonds such as, but not limited to, 2,5-dihydro-1H-pyrrolyl, 4H-[1,3,4]thiadiazinyl, 4,5-dihydrooxazolyl or 4H-[1,4]thiazinyl, or it may be benzo fused, such as, but not limited to, dihydroisoquinolinyl. According to the present disclosure, the heterocyclyl is non-aromatic.

The term "$C_{6-20}$ aryl" is understood to mean preferably a monovalent, aromatic or partially aromatic monocyclic, bicyclic or tricyclic hydrocarbon ring having 6 to 20 carbon atoms, preferably "$C_{6-14}$ aryl". The term "$C_{6-14}$ aryl" is understood to preferably mean a monovalent, aromatic or partially aromatic monocyclic, bicyclic or tricyclic hydrocarbon ring ("$C_{6-14}$ aryl"), having 6, 7, 8, 9, 10, 11, 12, 13 or 14 carbon atoms, especially a ring having 6 carbon atoms ("$C_6$ aryl"), such as phenyl; or biphenyl, or a ring having 9 carbon atoms ("$C_9$ aryl"), such as indanyl or fluorenyl, or a ring having 10 carbon atoms ("$C_{10}$ aryl"), such as tetrahydronaphthyl, dihydronaphthyl or naphthyl, or a ring having 13 carbon atoms ("$C_{13}$ aryl"), such as fluorenyl, or a ring having 14 carbon atoms ("$C_{14}$ aryl"), such as anthryl. The term "5-20 membered heteroaryl" is understood to include a monovalent monocyclic, bicyclic or tricyclic aromatic ring system having from 5 to 20 ring atoms and containing 1-5 hetero atoms each independently selected from N, O, S, such as "5-14 membered heteroaryl". The term "5-14 membered heteroaryl" is understood to include a monovalent monocyclic, bicyclic or tricyclic aromatic ring system having 5, 6, 7, 8, 9, 10, 11, 12, 13 or 14 ring atoms, especially 5 or 6 or 9 or 10 carbon atoms, and containing 1-5, preferably 1-3 hetero atoms, each independently selected from N, O, S, and in each case, can be benzofused. In particular, the heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl, and the like, and benzo derivatives thereof, such as benzofuranyl, benzothienyl, benzoxazolyl, benzisoxazolyl, benzimidazolyl, benzotriazolyl, carbazolyl, indolyl, isoindolyl, etc.; or pyridyl, pyridazinyl, pyrimidinyl, pyrazinyl, triazinyl, etc., and a benzo derivative thereof, such as quinolinyl, quinazolinyl, isoquinolyl, etc.; or azocinyl, indolizinyl, purinyl and a benzo derivative thereof; or cinnolinyl, phthalazinyl, quinazolinyl, quinoxalinyl, naphthyridinyl, pteridinyl, carbazolyl, acridinyl group, phenazinyl group, phenothiazine group, a phenoxazinyl or the like.

Unless otherwise indicated, heterocyclyl, heteroaryl includes all possible isomeric forms thereof, such as positional isomers thereof. Thus, for some illustrative and non-limiting examples, pyridyl includes pyridin-2-yl, pyridin-3-yl, pyridin-4-yl; thienyl includes thiophen-2-yl, thiophen-3-yl.

The above definitions of the term "alkyl", such as "$C_{1-40}$ alkyl", apply equally to other terms containing "$C_{1-40}$ alkyl", such as the terms "$C_{1-40}$ alkyloxy", "$C_{1-40}$ alkylsilyl" and "$C_{1-40}$ alkylsilyloxy" and the like. Similarly, the definitions of the above terms "$C_{2-40}$ alkenyl", "$C_{2-40}$ alkynyl", "$C_{3-20}$ cycloalkyl", "$C_{5-20}$ cycloalkenyl", "3-20 membered heterocyclyl", "$C_{6-20}$ aryl" and "5-20 membered heteroaryl" apply equally to other terms containing them, such as the terms "$C_{2-40}$ alkenyloxy", $C_{2-40}$ alkynyloxy", "$C_{3-20}$ cycloalkyloxy", "3-20 membered heterocyclyl", "3-20 membered heterocyclyloxy", "$C_{6-20}$ aryloxy", "$C_{6-20}$ arylalkyl" and "5-20 membered heteroarylalkyl" and the like.

The term "leaving group" as used herein, unless otherwise indicated, shall mean a charged or uncharged atom or group leaving during the substitution or displacement reaction. Suitable examples include, but are not limited to, H, F, Br, Cl, I, mesylate, tosylate, and the like.

In any method for preparing the compound of the invention, it may be necessary and/or desirable to protect any sensitive or reactive groups of the molecule, which can be achieved by conventional protecting groups, such as the protecting groups described in textbooks or reference books in the field. The protecting group can be removed at a convenient subsequent stage using methods known in the art. Those skilled in the art will recognize that other reagents can be used in the deprotection step, including but not limited to Pd/C, Pd(OH)$_2$, PdCl$_2$, Pd(OAc)$_2$/Et$_3$SiH, Raney nickel, a suitably selected acid, a suitably selected base and fluoride, and the like, depending on the particular protecting group.

According to the preparation method of the present disclosure, "optionally be further" means that the subsequent steps or operations may or may not be carried out as needed. For example, "be further subjected to a salt-forming step" means that the salt-forming step may or may not be carried out. Those skilled in the art will be able to determine whether to perform the steps or operations as desired for the target compound.

The target compound can be isolated according to known methods, for example, by extraction, filtration or column chromatography.

Depending on the molecular structure, the compound of the invention may be chiral and thus may exist in various enantiomeric forms. Thus these compounds may exist in racemic or optically active form. The compound of the present disclosure or the intermediate thereof can be isolated as an enantiomeric compound by chemical or physical methods well known to those skilled in the art, or used for synthesis in the enantiomeric form. In the case of a racemic amine, its diastereomers are prepared by a mixture obtained by reacting the amine with an optically active resolving agent. Examples of suitable resolving agents are optically active acids such as tartaric acids in the R form and S form, diacetyltartaric acid, dibenzoyltartaric acid, mandelic acid, malic acid, lactic acid, suitable N-protected amino acids (eg N-benzoyl valine or N-benzenesulfonyl valine) or various optically active camphorsulfonic acids. Optically active resolving agents (for example dinitrobenzoylphenylglycine immobilized on silica gel, cellulose triacetate or other carbohydrate derivatives or chiral derivatized methacrylate polymers) can be used to facilitate chromatographic enantiomer resolution. Suitable eluents for this purpose are aqueous or alcohol-containing solvent mixtures, for example, hexane/isopropanol/acetonitrile.

Those skilled in the art will appreciate that since nitrogen is required to have available lone pairs of electrons for oxidation to an oxide, not all nitrogen-containing heterocycles can form N-oxides; those skilled in the art will recognize nitrogen-containing heterocycles capable of forming N-oxides. Those skilled in the art will also recognize that tertiary amines can form N-oxides. Methods for the synthesis of N-oxides of heterocycles and tertiary amines are well known to those skilled in the art, comprising using peroxyacids such as peroxyacetic acid, m-chloroperoxybenzoic acid (MCPBA), hydrogen peroxide, alkyl hydroperoxides such as t-butyl hydroperoxide, sodium perborate and dioxirane such as dimethyl dioxirane to oxidize heterocycles and tertiary amines. These methods of preparing N-oxides were extensively described and reviewed in literatures.

The pharmaceutically acceptable salt may be, for example, an acid addition salt of the compound of the present disclosure having a nitrogen atom in the chain or ring and alkaline enough, for example, an acid addition salt formed with an inorganic acid such as hydrochloric acid, hydrofluoric acid, hydrobromic acid, hydroiodic acid, sulfuric acid, pyrosulfuric acid, phosphoric acid, nitric acid, hydrogen sulfate, or an acid addition salt formed with an organic acid such as formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentane propionic acid, digluconic acid, 3-hydroxy-2-naphthoic acid, nicotinic acid, pamoic acid, pectic acid, persulfate, 3-phenylpropionic acid, picric acid, pivalic acid, 2-hydroxyethanesulfonic acid, itaconic acid, sulfamic acid, trifluoromethanesulfonic acid, lauryl sulfate, ethanesulfonic acid, benzenesulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic, glycerophosphoric acid, aspartic acid, sulfosalicylic acid, sulfuric acid, or semi-thiocyanic acid.

Additionally, another suitable pharmaceutically acceptable salt of the compound of the present disclosure having sufficient acidity is an alkali metal salt (e.g., sodium salt or potassium salt), an alkaline earth metal salt (e.g., a calcium or magnesium salt), an ammonium salt, or a salt formed with an organic base providing a physiologically acceptable cation, for example, a salt formed with sodium ion, potassium ion, N-methylglucamine, dimethyl glucosamine, ethyl glucosamine, lysine, dicyclohexylamine, 1, 6-hexanediamine, ethanolamine, glucosamine, meglumine, sarcosine, serinol, trishydroxymethylaminomethane, aminopropanediol, 1-amino-2, 3, 4-butanetriol. As an example, the pharmaceutically acceptable salt comprises a salt formed by the group —COOH with sodium ion, potassium ion, calcium ion, magnesium ion, N-methylglucamine, dimethyl glucosamine, ethyl glucosamine, lysine, dicyclohexylamine, 1,6-hexamethylenediamine, ethanolamine, glucosamine, meglumine, sarcosine, serinol, trishydroxymethylaminomethane, aminopropanediol, 1-amino-2,3,4-butanetriol; when 1, 2 or 3 of M$_1$, M$_2$, M$_3$ of the present disclosure are H, the pharmaceutically acceptable salts of the present disclosure comprise, for example, salts formed by —OP(O)(OM$_1$)(OM$_2$), —P(O)(OM$_1$)(OM$_2$), —OS(O)$_2$OM$_3$, —S(O)$_2$ OM$_3$ with sodium ion, potassium ion, calcium ion, magnesium ion, N-methylglucamine, dimethyl glucosamine, ethyl glucosamine, lysine, dicyclohexylamine, 1,6-hexamethylenediamine, ethanolamine, glucosamine, meglumine, sarcosine, serinol, trishydroxymethylaminomethane, aminopropanediol and 1-amino-2,3,4-butanetriol.

Alternatively, the basic nitrogen-containing group can be quaternized with the following reagents: lower alkyl halides such as chloride, bromide and iodide of methyl, ethyl, propyl, butyl, butyl and butyl; dialkyl sulfates such as dimethyl sulfate, diethyl sulfate, dibutyl sulfate and dipentyl sulfate; long chain halides such as chlorides, bromides and iodides of mercapto, lauryl, myristyl and stearyl; aralkyl halides such as benzyl bromide and phenethyl bromide. As an example, pharmaceutically acceptable salts comprise hydrochlorides, sulfates, nitrates, hydrogen sulfates, hydrobromides, acetates, oxalates, citrates, methanesulfonates, formates or meglumine salt and the like.

Since the compound of the present disclosure may have a plurality of salt-forming sites, the "pharmaceutically acceptable salts" comprise not only salts formed by one salt-forming site but also salts formed by 2, 3 or all of the salt-forming sites of the compound of the present disclosure. Accordingly, the molar ratio of the compound of formula (I) to the acid anion or base cation required for the salt formation in the "pharmaceutically acceptable salt" may vary within a wide range, for example, 4:1-1:4, such as 3:1, 2:1, 1:1, 1:2, 1:3 and the like.

According to the present disclosure, the pharmaceutically acceptable anion comprises an anion selected from mineral or organic acids. The "inorganic acids" comprise, but are not limited to, hydrochloric acid, hydrofluoric acid, hydrobromic acid, hydroiodic acid, sulfuric acid, pyrosulfuric acid, phosphoric acid or nitric acid. The "organic acids" comprise, but are not limited to, formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectic acid, persulfate, 3-phenylpropionic acid, picric acid, pivalic acid, 2-hydroxyethanesulfonic acid, itaconic acid, sulfamic acid, trifluoromethanesulfonic acid, dodecyl sulfate, ethanesulfonic acid, benzene sulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid or thiocyanic acid.

The term "anion formed by ionization" comprises all possible anionic forms formed by ionization of inorganic and organic acids, for example, different anions formed by first-order ionization, secondary ionization or tertiary ionization. As an example, phosphoric acid may generate dihydrogen phosphate by first-order ionization, may generate hydrogen phosphate by secondary ionization, or may generate phosphate by three-stage ionization; sulfuric acid may generate hydrogen sulfate by first-order ionization, or may generate sulfate by secondary ionization. A plurality of molecules of the compound of formula (I) of the present disclosure may share a multivalent anion formed by multistage ionization. All of these possible anions are encompassed within the scope of the anions of the invention.

The term "tautomer" refers to a functional group isomer that is formed by the rapid movement of an atom in a molecule at two positions. The compounds of the present disclosure may exhibit tautomerism. There may exist two or more interconvertible species of tautomeric compounds. Proton-shifting tautomers are derived from the migration of covalently bonded hydrogen atoms between two atoms. Tautomers generally exist in equilibrium, and the attempt to separate a single tautomer typically result in a mixture having physicochemical properties consistent with the mixture of compounds. The position of equilibrium depends on the inherent chemical properties of the molecule. For example, in many aliphatic aldehydes and ketones such as acetaldehyde, the keto form predominates; while in phenol, the enol form predominates. The present disclosure encompasses all tautomeric forms of the compounds.

The term "effective amount" or "therapeutically effective amount" refers to the amount of the compounds of the present disclosure sufficient to meet the intended application (comprising but not limited to, the treatment of diseases as defined below). The therapeutically effective amount may vary depending on factors such as the intended application (in vitro or in vivo), or the subject and disease conditions being treated, such as the weight and age of the subject, the severity of the disease condition, the way of administration, and the like, which can be readily determined by the person skilled in the art. The particular dosage may vary depending on the particular compound selected, the dosage regimen upon which it is administered, whether it is administered in combination with other compounds, the timing of administration, the tissue to be administered, and the physical delivery system to carry it.

The term "auxiliary" refers to a pharmaceutically acceptable inert ingredient. Examples of the kind of excipient comprise, without limitation, a binder, a disintegrant, a lubricant, a glidant, a stabilizer, a filler, a diluent, and the like. Excipients enhance the handling characteristics of the pharmaceutical formulation by increasing the fluidity and/or adhesion to make the formulation more suitable for direct compression. Examples of typical pharmaceutically acceptable carriers suitable for use in the above formulations are: sugars such as lactose, sucrose, mannitol and sorbitol; starches such as corn starch, tapioca starch and potato starch; cellulose and its derivatives, for example, sodium carboxymethylcellulose, ethylcellulose and methylcellulose; calcium phosphates such as dicalcium phosphate and tricalcium phosphate; sodium sulfate; calcium sulfate; polyvinylpyrrolidone; polyvinyl alcohol; stearic acid; alkaline earth metal salts of a fatty acid such as magnesium stearate and calcium stearate; stearic acid; vegetable oils such as peanut oil, cottonseed oil, sesame oil, olive oil and corn oil; nonionic, cationic and anionic surfactants; glycol polymers; fatty alcohols; and cereal hydrolyzed solid as well as other non-toxic compatible excipients commonly used in pharmaceutical preparations such as fillers, binders, disintegrants, buffers, preservatives, antioxidants, lubricants, colorants, and the like.

Advantageous effect of the present disclosure comprises:

1. The present disclosure, by designing the prodrug compounds, solved the problems of voriconazole such as poor solubility and being difficult to improve its solubility by salt formation. The present disclosure developed a series of compounds with good salt-forming properties or water solubility. Furthermore, the compounds or the pharmaceutically acceptable salts thereof have good stability and excellent solubility in vitro, and can be rapidly converted into active ingredients after entering the body to exert pharmacological effects, and therefore are suitable for developing novel antibacterial drugs.

2. The present disclosure, by designing the prodrug compounds, also solved the problems that voriconazole itself is insoluble in water and needs to be solubilized by using a large amount of β-cyclodextrin excipients and reduced the toxicity risk caused by the excipients. Moreover, the compound of the present disclosure can be formulated into injections without using β-cyclodextrin excipients having safety problems for solubilization, which accordingly not only enables the administration to patients inconvenient for oral administration, but also greatly improves clinical safety; The compound can also be used to patients with moderate or severe renal impairment, suitable for use as a drug for more people.

3. The compound of the present disclosure further has good salt-forming property and water solubility, which can be rapidly converted into voriconazole after entering the gastrointestinal tract and exert pharmacological effects, thereby having better antifungal effects and greatly improving the oral bioavailability of voriconazole.

4. The pharmaceutical composition comprising the compound of the present disclosure, with no need of addition of special excipients and special processes, can facilitate simplification of the production process, reduction of production cost and safety hazard, as well as industrial production.

DETAILED DESCRIPTION

The compounds of the general formula of the present disclosure, as well as the preparation methods and applications thereof, will be further described in detail below in conjunction with specific examples. The following examples are merely illustrative of the present disclosure and are not to be construed as limiting the scope of the present disclosure. The technology that is implemented based on the above-described contents of the present disclosure is encompassed within the scope of the present disclosure.

The starting materials and reagents used in the following examples are commercially available or can be prepared by known methods unless otherwise stated.

Example 1 Preparation of Compound (QR16001) and its Sulfate 1.1 Preparation of Compound (QR16001-001)

Under a nitrogen atmosphere, 80 mL dichloromethane, 2-methylamino-3-pyridinemethanol (2.0 g, 0.014 mol) and 1.87 g N,N-diisopropylethylamine were added, and the reaction system was cooled to −15 to −20° C. followed by addition of a solution of 2.0 g (0.014 mol) 1-chloroethyl chloroformate in dichloromethane (20 mL) drop by drop. The reaction mixture was kept at the temperature of −15 to −20° C. for 16 hours.

To the above reaction mixture, Boc-glycine (2.8 g, 0.016 mol, CAS No.: 4530-20-5) and 0.24 g 4-dimethylaminopyridine (DMAP) were added, at a temperature of −15 to −20 OC, dissolved, and added with 2.48 g 1-ethyl-3-(3-dimethylaminopropyl) carbonyldiimide hydrochloride (CAS No.: 25952-53-8), and after the completion of addition, kept at the temperature of −15 to −20 OC for 8 h. The end of the reaction was judged by TLC. The reaction mixture was washed with 0.1 M hydrochloric acid, saturated sodium hydrogen carbonate and brine, dried, filtered, concentrated to give the crude product, which was purified by silica gel column chromatography to give 2.8 g colorless oil of Compound (QR16001-001). 1.2 Preparation of Compound (QR16001-002) 70 mL acetonitrile and 2.7 g (QR16001-001) were added, stirred to dissolve, and then added with 1.75 g voriconazole, sodium iodide (0.10 g, 0.13 eq.). The reaction system was heated to 50-60° C. for 5 h, and the end of the reaction was judged by TLC. The reaction mixture was concentrated to give a crude oily material, which was purified by silica gel column chromatography to give 2.0 g Compound (QR16001-002).

1.3 Preparation of Compound (QR16001)

0.78 g Compound (QR16001-002) was dissolved in 10 mL dioxane at room temperature, cooled to 0° C., added with 10 mL 4 M HCl/dioxane solution dropwise. After the completion of addition, the reaction mixture was stirred at room temperature and the end of the reaction was judged by TLC. The reaction mixture was filtered to give 0.52 g onium hydrochloride salt of Compound (QR16001); ESI-MS: 615.2.

1.4 Preparation of Compound (16001)

At room temperature, 0.5 g onium hydrochloride salt of Compound (QR16001) was dissolved in 30 mL purified water, added with 2.2 eq. NaOH, stirred for 1 h and extracted with dichloromethane, and the organic phase was dried and concentrated to give the corresponding free base of Compound (16001); ESI-MS: 615.2.

1.5 Preparation of sulfate of Compound (SF16001)

0.5 g Compound (QR16001) was dissolved in 30 mL purified water at room temperature, added with 30 g ion exchange resin (sulfate type), stirred at 0° C. for 3 to 5 h, filtered, and the filtrate was lyophilized to obtain 0.2 g amorphous sulfate of Compound (SF16001), which was identified by mass spectrometry and ion chromatography as the target product; ESI-MS: 615.2.

Referring to the preparation method of Compound (16001), the obtained product was reacted with an appropriate amount of base to obtain the corresponding free compound.

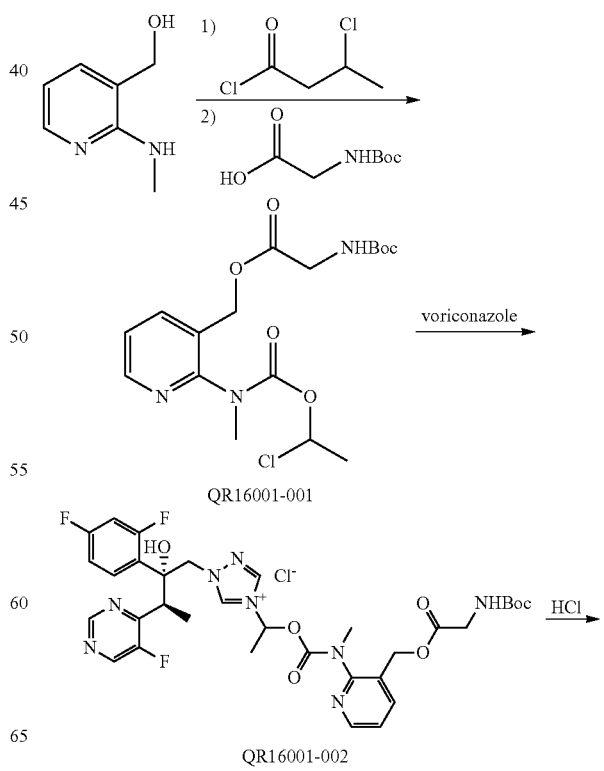

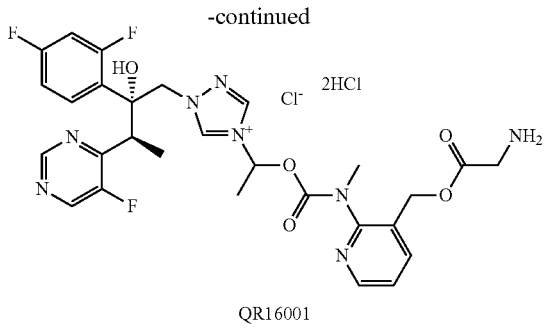

QR16001

The compound of the present disclosure can be obtained not only in the form of onium hydrochloride salt, but also onium hydrogeniodide salt or onium hydrobromide salt where the catalyst is NaBr or NaI or the catalyst exceeds a catalytic amount; onium sulfate, onium phosphate and onium nitrate salts can be prepared by using ion exchange resins, and each salt is freed with a suitable amount of base to obtain the corresponding anion product of the compound.

Example 2 Preparation of Compound (QR16002) and its Sulfate, Nitrate and Phosphate 2.1 Preparation of Compound (QR16002-001) Referring to the preparation method of Compound (QR16001-001), Compound (QR16002-001) was obtained by using (S)-2,5-bis(di-tert-butoxycarbonylamino)pentanoic acid (CAS No. 57133-29-6) instead of Boc-glycine as a starting material.

2.2 Preparation of Compound (QR16002-002)

Compound (QR16002-002) was prepared by taking the preparation method of Compound (QR16001-002) as a reference.

2.3 Preparation of Compound (QR16002)

0.80 g Compound (QR16002-002) was dissolved in 10 mL dioxane at room temperature, and the system was cooled to 0° C. after stirring, and added dropwise slowly with 10 mL 4 M HCl/dioxane solution at 0° C. After the completion of the addition, the reaction mixture was stirred at room temperature for 1 hour, and the end of the reaction was judged by TLC. The reaction mixture was filtered rapidly under nitrogen atmosphere, and the solid was washed successively with ethyl acetate and acetone, to obtain 0.54 g onium hydrochloride salt of Compound (QR16002); ESI-MS: 672.3.

2.4 Preparation of Compound (16002)

Compound (16002), the corresponding free base of Compound (QR16002), was prepared by taking the preparation method of Compound (16001) as a reference; ESI-MS: 672.3.

2.5 Preparation of Compound (SF16002)

Referring to the preparation method of Compound (SF160011), by using Compound (QR16002) as a raw material, the sulfate (SF16002) of Compound (QR16002) was obtained by ion exchange, and the target product was detected by ion chromatography; ESI-MS: 672.3.

Similarly, referring to the preparation method of Compound (16001), the obtained product was reacted with an appropriate amount of base to obtain the corresponding free compound 16010; ESI-MS: 672.3.

2.6 Preparation of Nitrate and Phosphate of the Compound

As described above, referring to the preparation method of Compound (SF16002), by using ion exchange resins of phosphate type and nitrate type, the corresponding onium phosphate salt (QR16011; ESI-MS: 672.3) and onium nitrate salt (QR16012; ESI-MS: 672.3) were respectively obtained, which were identified by ion chromatography as the target products.

Referring to the preparation method of Compound (16001), the above onium salts were reacted with an appropriate amount of base, and the corresponding free base (16011; ESI-MS: 672.3) and (16012; ESI-MS: 672.3) were obtained.

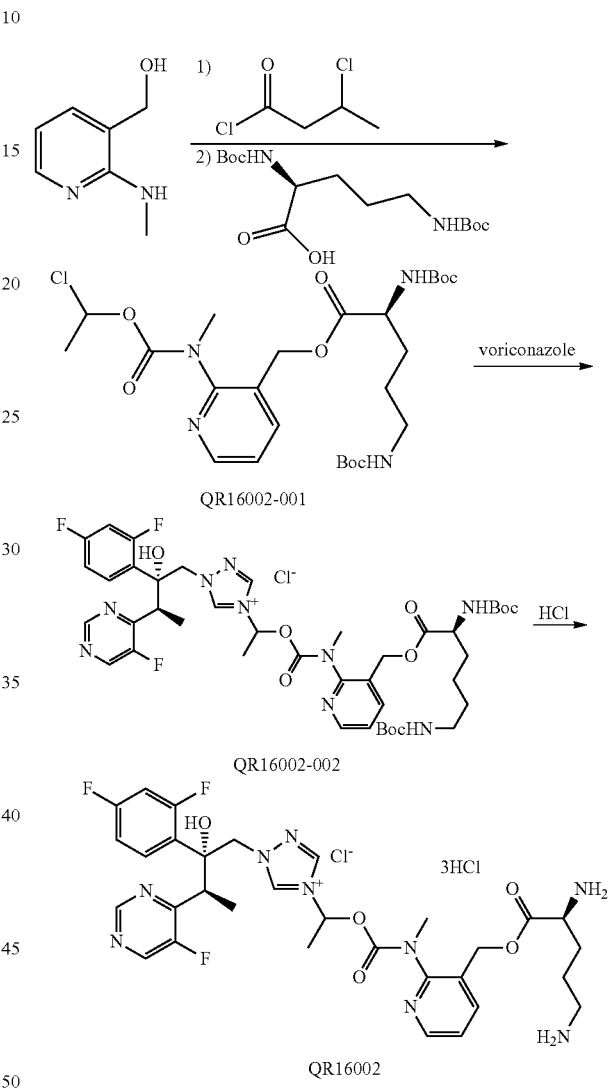

Example 3 Preparation of the Compound (QR16006) and (QR16008)

3.1 Preparation of Compound (QR16006)

Referring to the preparation method of Compound (QR16002) in the above example, onium iodide hydrochloride salt (QR16006) was obtained by using 1.4 eq. sodium iodide; ESI-MS: 672.3.

Referring to the preparation method of Compound (16001), the obtained product was reacted with an appropriate amount of base to obtain the corresponding free compound (16006); ESI-MS: 672.3.

3.2 Preparation of Compound (QR16008)

Referring to the preparation method of Compound (QR16002) in the previous example, onium bromide hydrochloride salt (QR16008) was obtained by using sodium bromide as a catalyst, the amount of which was 1.4 eq.; ESI-MS: 672.3.

Referring to the preparation method of Compound (16001), the obtained product was reacted with an appropriate amount of base to obtain the corresponding free compound (16008); ESI-MS: 672.3.

Example 4 Preparation of Compound (QR16003)

Referring to the preparation method of Compound (QR16001), Compound (QR16003) was obtained by replacing Boc-glycine with tert-butoxycarbonyl-L-aspartic acid tert-butyl ester (CAS No.: 34582-32-6), which was detected by mass spectrometry and ion chromatography as the target product; ESI-MS: 673.2.

Referring to the preparation method of Compound (16001), the free base compound (16003) of Compound (QR16003) was obtained; ESI-MS: 672.3. Furthermore, the other onium salts were also obtained.

Example 5 Preparation of Compound (QR16004)

5.1 Preparation of Compound (QR16004-001)

Referring to the preparation method of Compound (QR16001-001), Compound (QR16004-001) was obtained by using mono-tert-butyl succinate instead of Boc-glycine as a raw material.

5.2 Preparation of Compound (QR16004-002)

Referring to the preparation method of Compound (QR16001-002), Compound (QR16004-002) was obtained by using Compound (QR16004-001) as a raw material.

5.3 Preparation of Compound (16004)

Referring to the preparation method of Compound QR16001, the hydrochloride salt of Compound (16004) was obtained by using Compound (QR16004-002) as a raw material, and the formate of Compound (16004) was obtained by preparative HPLC, and the target products were identified as the target product by ion chromatography.

Referring to the preparation method of Compound (16001), the hydrochloride or formate of Compound (16004) was reacted with an appropriate amount of NaOH to give the corresponding free base (16004); ESI-MS: 658.2.

5.4 Preparation of Compound (QR16004)

To 0.15 g Compound (16004) hydrochloride, 5 mL methanol was added, and 2.5 equivalent NaOH methanol solution was added dropwise at 0° C. The reaction mixture was stirred for 30 min, and added with 60 mL methyl tert-butyl ether, further stirred for 15 min, filtered to obtain the sodium salt of Compound (QR16004), which was identified as the target product by mass spectrometry and ion chromatography; ESI-MS: 658.2.

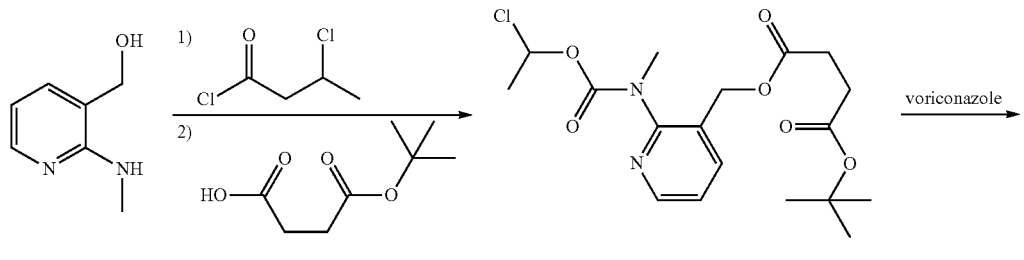

QR16004-001

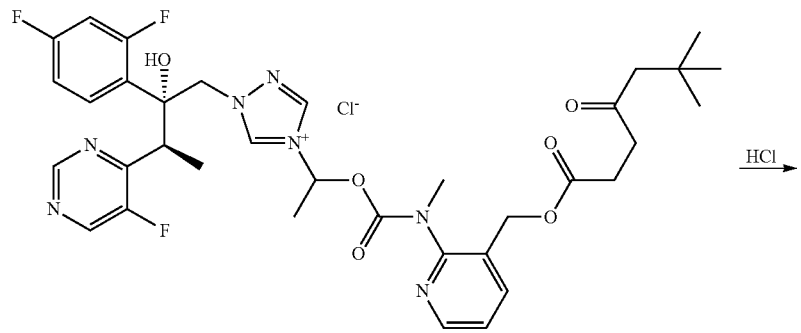

QR16004-002

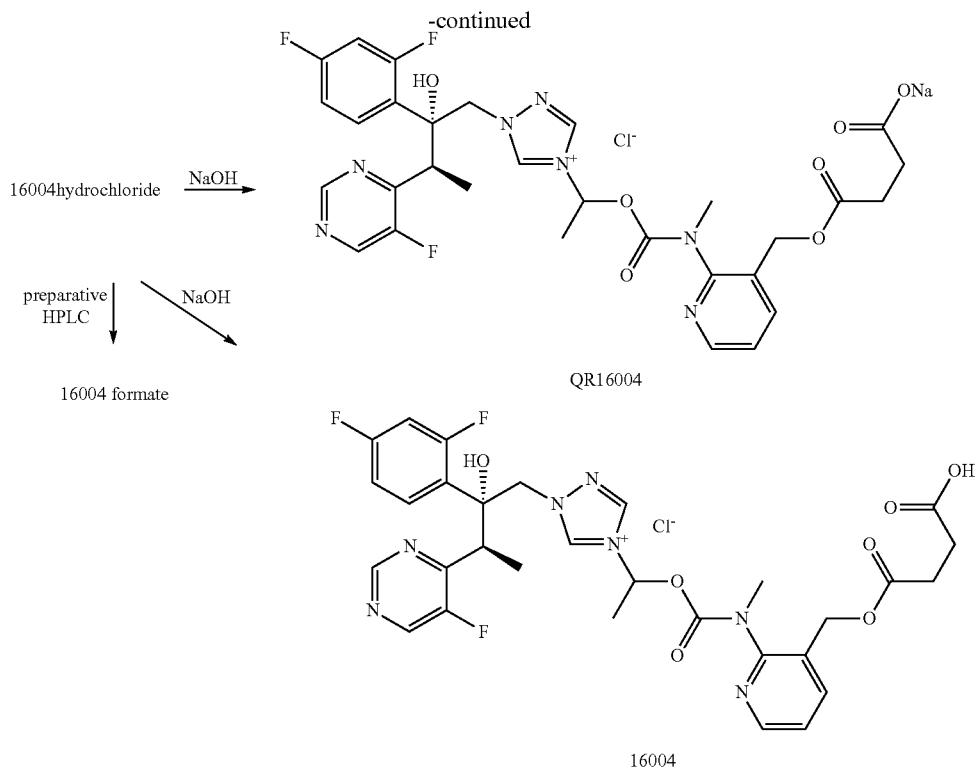

16004

Example 6 Preparation of Compound (QR16005)

Referring to the preparation method of Compound (QR16001), Compound (QR16005) was obtained by replacing Boc-glycine with QR16005-SM (the preparation method thereof referring to the Journal of Inorganic Biochemistry 98 (2004) 1933-1946), ESI-MS: 658.3.

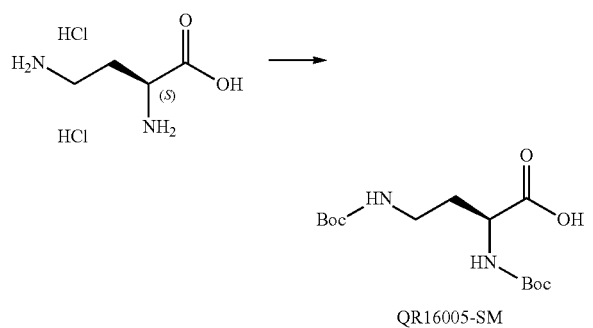

QR16005-SM

Referring to the preparation method of (16001) in the previous example, the free base (16005) of Compound (QR16005) was obtained; ESI-MS: 658.3.

Example 7 Preparation of Compound (QR16007)

Referring to the preparation method of Compound (QR16001), Compound (QR16007) was obtained by replacing Boc-glycine with (2S)-2,5-bis(tert-butoxycarbonylamino)pentanoic acid (CAS No. 57133-29-6) and replacing 2-methylamino-3-pyridinemethanol with 2-methylaminobenzyl alcohol; ESI-MS: 671.3.

Referring to the preparation method of (16001) in the previous examples, the corresponding free base (16007; ESI-MS: 671.3) of Compound (QR16007) was obtained, and other onium salts and corresponding free bases thereof were also obtained.

Example 8 Preparation of Compound (QR16009)

Referring to the preparation method of Compound (QR16001), Compound (QR16009) was obtained by replacing Boc-glycine with N-tert-butoxycarbonyl-L-citrulline (CAS No. 45234-13-7), ESI-MS: 715.3.

Referring to the preparation method of Compound (16001) in the previous example, the corresponding free base (16009) of the Compound (QR16009) was obtained by reacting it with a suitable amount of base; ESI-MS: 715.3.

Example 10 Preparation of Compound (QR16013), (SF16013) and (16013)

Referring to the preparation method of Compound (QR16001), Compound (QR16013) was obtained by replacing Boc-glycine with N-Boc-L-glutamine (CAS No. 13726-85-7), ESI-MS: 686.3.

By using Compound (QR16013) as a raw material, the sulfate (SF16013) of Compound (QR16013) was obtained referring to the preparation method of Compound (SF16001), and the target product was identified by mass spectrometry and ion chromatography; ESI-MS: 686.3.

Compound (QR16013) was used as a raw material, reacting with a suitable amount of base to obtain the corresponding free Compound (16013), referring to the preparation method of Compound (16001); ESI-MS: 686.3.

In the same manner, other onium salts and corresponding free bases were also be prepared.

Example 11 Preparation of Compound (QR16014), (SF16014) and (16014)

Referring to the preparation method of Compound (QR16001), Compound (QR16014) was obtained by replacing Boc-glycine with N-Boc-L-asparagine (CAS No. 7536-55-2), ESI-MS: 672.3. Compound (QR16014) was used as a starting material to give Compound (SF16014), referring to the preparation method of Compound (SF16001), and the target product was identified by mass spectrometry and ion chromatography; ESI-MS: 672.3.

Compound (QR16014) was used as a starting material to obtain the corresponding free Compound (16014), referring to the preparation method of Compound (16001); ESI-MS: 672.3.

Example 12 Preparation of Compound (QR16015), (SF16015) and (16015)

Referring to the preparation method of Compound (QR16001), Compound (QR16015) was obtained by replacing Boc-glycine with N-Boc-O-tert-butyldimethylsilyl-L-serine (CAS No. 90181-25-2, the preparation method thereof referring to Example 3 of the patent document CN103626825A); ESI-MS: 645.2.

Compound (QR16015) was used as a starting material to obtain Compound (SF16015), referring to the preparation method of Compound (SF16001), and the target product was identified by mass spectrometry and ion chromatography; ESI-MS: 645.2.

Compound (QR16015) was used as a starting material to obtain the corresponding free base (16015), referring to the preparation method of Compound (16001); ESI-MS: 645.2.

Example 13 Preparation of Compound (QR16016), (SF16016) and (16016)

Referring to the preparation method of Compound (QR16001), Compound (QR16016) was obtained by replacing Boc-glycine with N-Boc-O-tert-butyldimethylsilyl-L-threonine (CAS No. 90181-26-3, the preparation method thereof referring to the preparation of 614b on page 377 of the patent document WO2013130660A), ESI-MS: 659.3.

The compound (QR16016) was used as a raw material, to obtain the corresponding sulfate Compound (SF16016), referring to the preparation method of Compound (SF16001), and the target product was identified by mass spectrometry and ion chromatography; ESI-MS: 659.3.

Compound (QR16016) was used as a starting material, to obtain the corresponding free compound (16016), referring to the preparation method of Compound (16001), ESI-MS: 659.3.

Example 14 Preparation of Compound (QR16017)

Referring to the preparation method of Compound (QR16001), Compound (QR16017) was obtained by replacing boc-glycine with (S)-2,6-di-tert-butoxycarbonylaminocaproic acid (CAS No.: 2484-46-7), ESI-MS: 686.3.

Compound (QR16017) was used as a starting material, to obtain Compound (SF16017), referring to the preparation method of Compound (SF16001), and the target product was identified by mass spectrometry and ion chromatography; ESI-MS: 686.3.

Compound (QR16017) was used as a starting material, to obtain the corresponding free Compound (16017), referring to the preparation method of Compound (16001); ESI-MS: 686.3.

Example 15 Preparation of Compound (QR16018) and (16018)

Referring to the preparation method of Compound (QR16001), Compound (QR16018) was obtained by replacing Boc-glycine with N-Boc-O-tert-butyldimethylsilyl-L-tyrosine (CAS No. 94732-15-7, the preparation method thereof referring to the preparation of Compound 14 on page 21 of WO2008106860A1), ESI-MS: 721.3.

Compound (QR16018) was used as a starting material to obtain Compound (16018), referring to the preparation method of Compound (16001), ESI-MS: 721.3.

Example 16 Preparation of Compound (QR16019)

Referring to the preparation method of Compound (QR16001), Compound (QR16019) was obtained by replacing boc-glycine with (S)-2-tert-butoxycarbonylamino-5-tert-butoxycarbon-ylmethylaminovaleric acid (the preparation method thereof referring to Bioorg. Med. Chem. Lett. 15 (2005), 3934-3941), ESI-MS: 686.3.

Compound (QR16019) was used as a starting material to obtain Compound (16019), referring to the preparation of the Compound (16001); ESI-MS: 686.3.

Example 17 Preparation of Compound (QR16020), (16020) and (SF16020)

Referring to the preparation method of Compound (QR16001), Compound (QR16020) was obtained by replacing Boc-glycine with Boc-sarcosine as a starting material (CAS No.: 13734-36-6), ESI-MS: 629.3.

Compound (QR16020) was used as a starting material to obtain Compound (16020), referring to the preparation method of the Compound (16001); ESI-MS: 629.3.

Compound (QR16020) was used as a starting material to obtain compound (SF16020), referring to the preparation method of Compound (SF16001) and the target product was identified by mass spectrometry and ion chromatography; ESI-MS: 629.3. Compound (SF16020) was used as a starting material, and reacted with an appropriate amount of base to obtain a corresponding free base, referring to the preparation method of Compound (16001).

Example 18 Preparation of the Compound (QR16021)

Referring to the preparation method of Compound (QR16001), Compound (QR16021) was obtained by replacing Boc-glycine with (S)-2-tert-butoxycarbonylamino-4-tert-butoxy-carbonylmethylaminobutyric acid (the preparation method referring to Bioorg. Med. Chem. Lett. 15 (2005) 3934-3941), ESI-MS: 672.3.

Compound (QR16021) was used as a starting material to obtain the corresponding free base Compound (16021), referring to the preparation method of Compound (16001); ESI-MS: 672.3.

Example 19 Preparation of Compound (QR16022)

19.1 Preparation of Compound (QR16022-SM-002)

5 g (QR16022-SM-001) was dissolved in DMF (50 mL) under nitrogen protection, added with 2 eq. potassium carbonate, stirred at room temperature for 5-10 min, added successively with 0.1 molar eq. CuI, 1.2 eq. methylamine hydrochloride, and then heated to 100° C. for 20 h. The end of the reaction was confirmed by TLC. The reaction mixture was filtered, concentrated, and purified by column chromatography to give 1.71 g Compound (QR16022-SM-002).

19.2 Preparation of Compound (QR16022-SM)

0.5 g Compound (QR16022-SM-002) and 1.5 eq. Boc anhydride were dissolved in 8 mL ethanol, added with about 50 mg Raney Ni, and the reaction was carried out for 18 hours under a hydrogen atmosphere. The end of the reaction was confirmed by TLC, and the reaction mixture was filtered, concentrated and purified by column chromatography to give 308 mg Compound (QR16022-SM). 19.3 Preparation of Compound (QR16022-001)

Under nitrogen protection, 0.01 mol (QR16022-SM), 80 mL dichloromethane and 0.01 mol N,N-diisopropylethylamine were added into s a flask. The reaction mixture in the flask was stirred and cooled to −15 to −20 OC, and added dropwise with 0.01 mol 1-chloroethyl chloroformate in dichloromethane (20 mL). After completion of the addition, the reaction mixture was kept at the temperature of −15 to −20° C. to further react for 16 h, added with 100 mL water, stirred and separated to different liquid phases. The organic phase was washed with brine, dried, filtered and concentrated to give the crude product, which was then purified by silica gel column chromatography to give 2.70 g Compound (QR16022-001).

19.4 Preparation of Compound (QR16022-002)

0.005 mol above-prepared compound (QR16022-001), 70 mL of acetonitrile were added into a flask, stirred and dissolved, added with 0.005 mol voriconazole and 0.1 eq. sodium iodide, and then heated to 50-60° C. to react for 5 h. The end of the reaction was judged by TLC. The reaction mixture was concentrated to give a crude oil, which was then purified by silica gel column chromatography to give 2.56 g Compound (QR16022-002).

19.5 Preparation of Compound (QR16022)

0.001 mol Compound (QR16022-002) was dissolved in 20 mL ethyl acetate at room temperature. The reaction mixture was stirred and dissolved, added with a solution of hydrogen chloride in ethyl acetate (5 mL, 4 mol/L) dropwise at 0° C. After the addition was completed, the temperature was raised to room temperature while keeping stirring. The end of the reaction was judged by TLC. The reaction mixture was filtered to give 0.45 g Compound (QR 16022), ESI-MS: 557.2.

19.6 Preparation of Compound (16022)

Compound (QR16022) was used as a starting material to obtain Compound (16022), referring to the preparation method of Compound (16001); ESI-MS: 557.2.

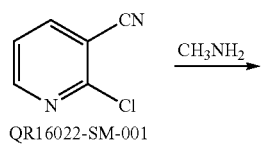

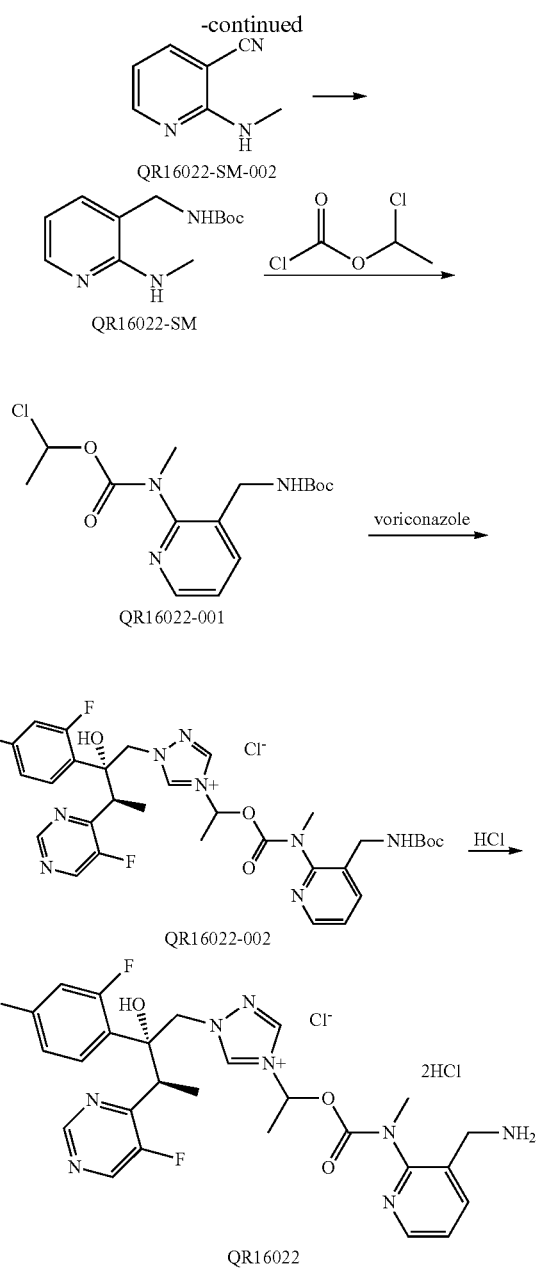

Example 20 Preparation of Compound (QR16023)

20.1 Preparation of Compound (QR16023-SM-002)

The preparation method was referring to literature Chem. Asian J, 2014, 9, 739-743.

20.2 Preparation of Compound (QR16023-SM)

The preparation method was referring to the preparation of Compound 27 on page 73 of patent document WO 2015/112801.

20.3 Preparation of Compound (QR16023)

The preparation method was referring to the preparation method of (QR16022) in the above examples, and the target compound was obtained by replacing Compound (QR16022-SM) with (QR16023-SM); ESI-MS: 571.2.

The preparation route of Compound (QR16023-SM) was as follows:

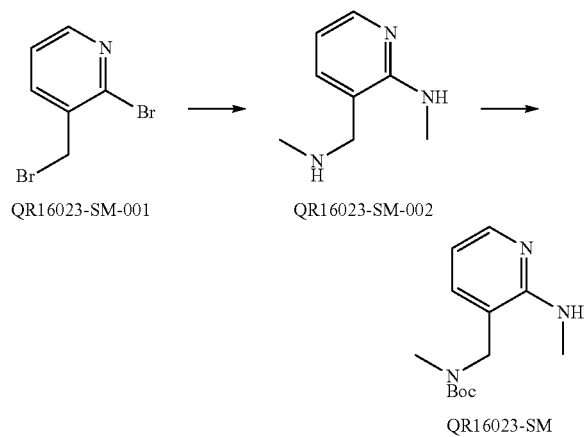

Compound (QR16023) was used as a starting material to obtain the corresponding free base Compound (16023) referring to the preparation method of Compound (16001); ESI-MS: 571.2.

Example 21 Preparation of Compound (16046) and (QR16046)

21.1 Preparation of Compound (16046-001)

Under nitrogen protection, 0.01 mol ethylene glycol was dissolved in dichloromethane (45 mL), stirred and cooled to −5 to 5° C., added with pyridine (0.012 mol), and added with 0.01 mol phosphorus oxychloride di-tert-butyl ester dropwise (CAS No.: 56119-60-9), and the reaction mixture was kept for 2 h under the same temperature after the completion of the dropwise addition. The reaction was judged by TLC. The reaction mixture was added with 0.1M hydrochloric acid (30 mL), stirred, separated to different liquid phases and the organic phase was washed successively by 1N diluted hydrochloric acid, brine, dried, filtered, concentrated, and purified by silica gel column chromatography to give 2.10 g Compound (16046-001).

21.2 Preparation of Compound (16046-002)

Under nitrogen protection, 0.005 mol Compound (16046-001) was dissolved in acetonitrile (60 mL), added with pyridine (0.012 mol), and added dropwise with 1-chloroethyl chloroformate (0.006 mol). The reaction mixture was kept under the same temperature for 2 h after the completion of addition. The end of the reaction was judged by TLC. The reaction mixture was added with 0.1M hydrochloric acid (30 mL), stirred, separated to different liquid phases and the organic phase was washed successively with saturated sodium bicarbonate, brine, dried, filtered, concentrated, and purified by silica gel column chromatography to give 1.20 g Compound (16046-002).

21.3 Preparation of Compound (16046-003)

Under nitrogen protection, 0.0025 mol Compound (16046-002) was dissolved in acetonitrile (60 mL) added with 0.0025 mol voriconazole and 0.1 eq. sodium iodide, stirred and heated to 65-70° C. for 16 h, and the reaction was judged by TLC. The reaction mixture was cooled to room temperature, added with silica gel to mix and purified by column chromatography to give 0.65 g Compound (16046-003).

21.4 Preparation of Compound (16046)

0.002 mol Compound (16046-003) was dissolved in 10 mL ethyl acetate at room temperature, added with HCl/dioxane (4 mol/L, 5 mL) dropwise at 0° C. After the addition was completed, the reaction mixture was warmed to room temperature and stirred. The end of the reaction was judged by TLC. The reaction mixture was filtered to give 0.68 g Compound (16046), ESI-MS: 5621.

21.5 Preparation of Compound (QR16046)

Under nitrogen protection, 0.001 mol (16046) was dissolved in 5 mL methanol stirred and cooled to −5 to 5° C., and added with 0.002 mol sodium hydroxide aqueous solution (1 mL) dropwise. After the completion of addition, the reaction mixture was kept for 10 to 20 min at the same temperature. The reaction mixture was concentrated at room temperature with a small amount of methanol remaining, then added with MTBE to precipitate solid, which was filtered to give 0.46 g Compound (QR16046), ESI-MS: 562.1.

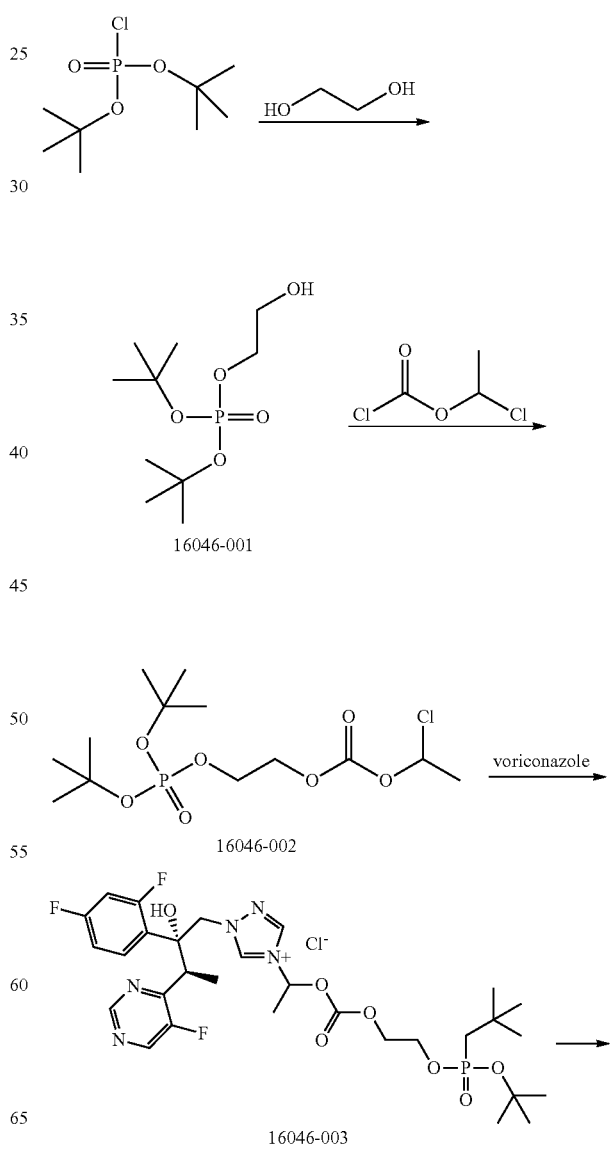

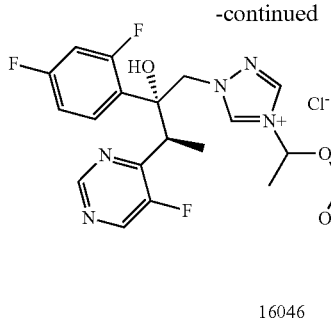

16046

Example 22 Preparation of Compounds (16024) and (QR16024)

Starting from butanediol, the preparation method was carried out with reference to the preparation of Compound (16046) to give Compound (16024), ESI-MS: 590.1.

Compound (QR16024) was obtained referring to the preparation method of Compound (QR16046). ESI-MS: 590.1.

Example 23 Preparation of Compounds (16025) and (QR16025)

Starting from pentanediol, the preparation method was carried out with reference to Compound (16046) and (QR16046) to give Compound (16025, ESI-MS: 604.2) and a salt thereof (QR16025, ESI-MS: 604.2).

Example 24 Preparation of Compounds (16026) and (QR16026)

24.1 Preparation of Compound (16026-001)

Under nitrogen protection, 0.01 mol (16026-SM) (CAS No.: 50595-15-8), 80 mL dichloromethane, 0.01 mol N,N-diisopropylethylamine were added into a reaction flask. The reaction mixture was stirred, cooled to −15 to −20 OC, and added with a solution of 0.01 mol 1-chloroethyl chloroformate in dichloromethane (20 mL) dropwise. The reaction mixture was kept at a temperature of −15 to −20 OC for 16 h, added with water, stirred, and separated to different liquid phases. The organic phase was washed with brine, dried, filtered, concentrated to give a crude product and purified by column chromatography to give Compound (16026-001).

24.2 Preparation of Compound (16026-002)

0.005 mol above-prepared compound (16026-001) and 70 mL acetonitrile were added into a reaction flask, stirred and dissolved, added with 0.005 mol voriconazole and 0.1 g sodium iodide, heated to 50-60° C. for 5 h. The end of the reaction was judged by TLC. The reaction mixture was concentrated to give a crude oily product, which was purified by column chromatography to give Compound (16026-002).

24.3. Preparation of Compound (16026)

0.001 mol Compound (16026-002) was dissolved in 20 mL ethyl acetate at room temperature, stirred and dissolved, and added with a solution of hydrogen chloride in ethyl acetate (5 mL, 4 mol/L) dropwise at 0° C. After the addition was completed, the temperature was raised to room temperature while stirring was continued for 1 h. The end of the reaction was judged by TLC. The reaction mixture was filtered to give Compound (16026), ESI-MS: 496.1.

24.4 Preparation of Compound (QR16026)

Compound (QR16026) was obtained referring to the preparation method of Compound (QR16046); ESI-MS: 496.1.

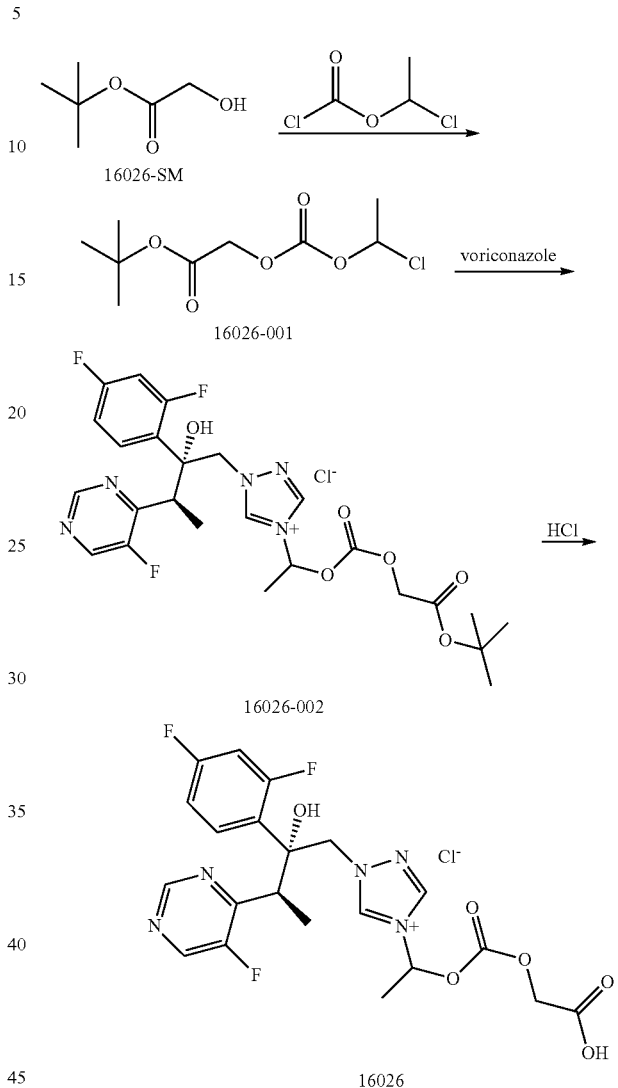

Example 25 Preparation of Compound (QR16027)

25.1 Preparation of Compound (QR16027-SM)

0.01 mol (QR16027-SM-001) was dissolved in tetrahydrofuran, added with 0.012 mol triethylamine, cooled to −5 to 5° C., added dropwise with 0.012 mol isopropyl chloroformate, reacted at room temperature for 3 hours, and filtered. The filtrate was added dropwise to an aqueous solution (5 mL) of 0.02 mol $NaBH_4$ while the temperature of the reaction mixture was controlled within the range of −5 to 5° C. And then the reaction mixture reacted overnight at room temperature after the dropwise addition was completed. The reaction mixture was added successively 50 mL water and 50 mL ethyl acetate, stirred and separated to different liquid phases, and the organic phase was washed successively with diluted hydrochloric acid of pH=2, 1M sodium hydrogencarbonate and brine, dried, filtered, and concentrated to obtain a crude product, which was purified by silica gel column chromatography to give 1.56 g Compound (QR16027-SM). The preparation route of the compound (QR16027-SM) was as follows:

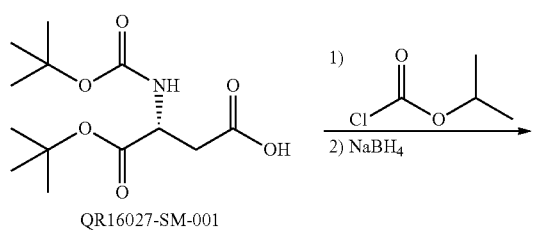

QR16027-SM-001

QR16027-SM

25.2 Preparation of Compound (QR16027)

Referring to the preparation method of Compound (QR16026), Compound (QR16027) was obtained by replacing (16026-SM) with Compound (QR16027-SM); ESI-MS: 539.2.

25.3 Preparation of Compound (16027)

Compound (16027) was obtained referring to the preparation method of Compound (16001); ESI-MS: 539.2.

Example 26 Preparation of Compound (16042)

26.1 Preparation of Compound (16042-002)

15 ml acetonitrile, 15 ml water and 3.96 g silver carbonate were added to a reaction flask, stirred for 5 minutes, added with 3 g di-tert-butyl phosphate, and stirred at room temperature for 1 h. The reaction mixture was concentrated under reduced pressure to give the di-tert-butyl phosphate silver salt (16042-001).

Toluene, 0.01 mol di-tert-butyl phosphate silver salt (16042-001), and 0.01 mol 1-chloro-1-iodomethane were added into a reaction flask, heated to 100° C. overnight, cooled to room temperature, filtered, concentrated under reduced pressure to give a crude product, which was purified by silica gel column chromatography to give 1.8 g Compound (16042-002).

26.2 Preparation of Compound (16042-003)

Under nitrogen protection, 0.005 mol (16042-002) was dissolved in acetonitrile (100 mL), added with 0.01 mol voriconazole and 0.1 g sodium iodide, stirred and heated to 70° C. for 16 h. The end of the reaction was judged by TLC. The reaction mixture was cooled to room temperature, and purified by column chromatography to give 1.8 g compound (16042-003).

26.3 Preparation of Compound (16042)

0.5 g Compound (16042-003) was dissolved in 5 mL dichloromethane, stirred and dissolved, added dropwise with a solution of hydrogen chloride in dioxane, and then kept stirring at room temperature for reaction after the completion of dropwise addition. The end of the reaction was judged by TLC. The reaction mixture was kept standing still, and then the supernatant obtained was decanted and concentrated to give 0.260 g solid product (16042); ESI-MS: 460.1.

26.4 Preparation of Compound (QR16042)

3 mL methanol and 0.1 g compound (16042) were added into a reaction flask, stirred and dissolved, cooled to 0° C., added dropwise with a methanol solution of sodium hydroxide (13 mg NaOH dissolved in 4 mL methanol), stirred for 30 minutes, then added with 30 mL methyl tert-butyl ether, stirred for 15 mins, and filtered to give 52 mg Compound (QR16042), ESI-MS: 460.1.

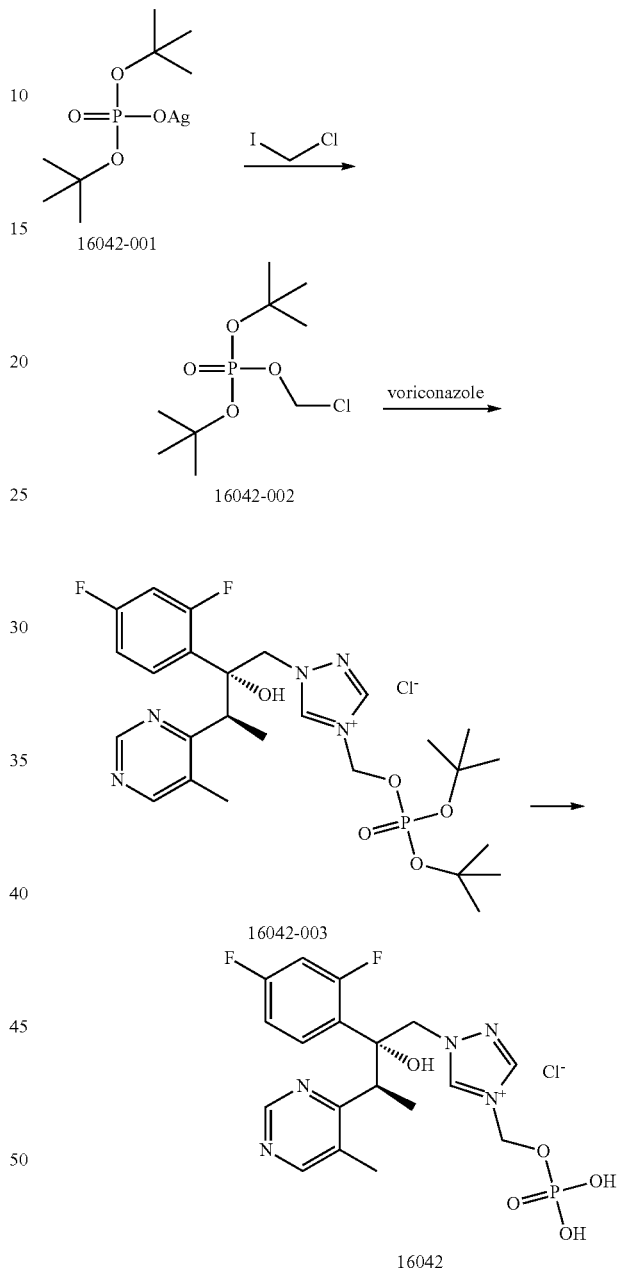

Example 27 Preparation of Compound (16028) and Compound (QR16028)

Starting from 1-chloro-1-iodoethane (CAS No. 594-00-3), the preparation was carried out with reference to Compound (16042) to give Compound (16028); ESI-MS: 474.1.

Compound (16028) was used as a starting material to obtain Compound (QR16028), referring to the preparation method of Compound (QR16042), ESI-MS: 474.1.

Example 28 Preparation of Compound (QR16029) and Compound (16029)

Starting from N-Boc-L-serine tert-butyl ester (CAS No. 7738-22-9), the preparation method was carried out with reference to Compound (QR16027) to give Compound (QR16029), ESI-MS: 474.1.

Referring to the preparation method Compound (16001), by reacting (QR16029) as a starting material with a suitable amount of a base, the free base Compound (16029) thereof was obtained; ESI-MS: 474.1.

Example 29 Preparation of Compound (16032) and Compound (QR16032)

Referring to the preparation method of Compound (16026), the target Compound (16032) was obtained by replacing the starting material 2-tert-butyl glycolate (CAS No. 50595-15-8) with bis-tert-butylphosphoric acid (CAS No. 33494-81-4); ESI-MS: 518.1.

Preparation of Compound (QR16032):
5 mL methanol and 0.2 g Compound (16032) were added to a reaction flask, stirred and dissolved, cooled to 0° C., added with a methanol solution of sodium hydroxide (15 mg NaOH dissolved in 5 mL methanol) dropwise, stirred for 30 minutes, added with 30 mL methyl tert-butyl ether, stirred for 20 min, and filtered to give Compound (QR16032), ESI-MS: 518.1.

Example 30 Preparation of Compound (16030) and Compound (QR16030)

Starting from diethylene glycol, the preparation method was carried out with reference to (16046) and (QR16046) to give Compound (16030) and its salt (QR16030); ESI-MS: 606.1.

Example 31 Preparation of Compound of (16031)

31.1 Preparation of Compound (16031-001)
16031-SM (CAS 29167-28-0, preparation method referring to Burslem, G M, et al., "Synthesis of highly functionalized oligobenzamide proteomimetic foldamers by late stage introduction of sensitive groups.", Organic & Biomolecular Chemistry 14.15 (2016): 3782) was used as a starting material to obtain the product, referring to the preparation method of Compound (16026-001).

31.2 Preparation of Compound (16031-002)
Using Compound (16031-001) as a reaction substrate, the target product was obtained referring to the preparation method of Compound (16026-002).

31.3 Preparation of Compound (16031)
15 mL dichloromethane and 0.001 mol Compound (16031-002) were added to a reaction flask, stirred and dissolved, added with trifluoroacetic acid dropwise, reacted at 0° C. overnight. The reaction mixture was concentrated under reduced pressure to give 0.35 g Compound (16031), ESI-MS: 498.1.

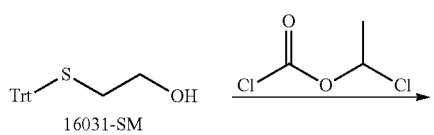

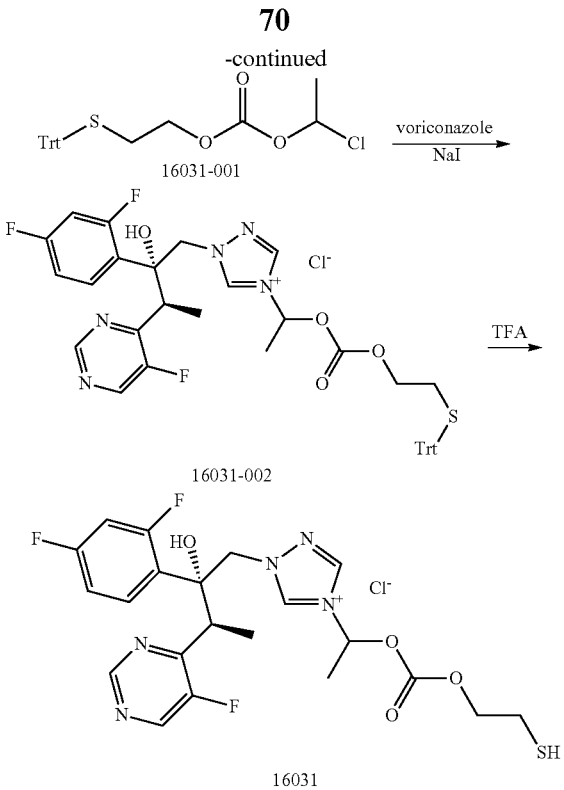

Example 32 Preparation of Compound (16033) and Compound (QR16033)

Starting from triethylene glycol, the preparation method was carried out with reference to (16046) and (QR16046) to give Compound (16033, ESI-MS: 650.1) and its salt (QR16033, ESI-MS: 650.1).

Example 33 Preparation of Compound (QR16034) and Compound (16034)

33.1 Preparation of Compound (QR16034-SM-002)
To a three-necked flask, L-cystine di-tert-butyl ester dihydrochloride (QR16034-SM-001) 7.68 g, DMF 180 mL, and triethylamine 3.84 g were added successively, stirred at room temperature for 5 min, added with 2 eq. Boc anhydride, and reacted at room temperature. The end of the reaction was judged by TLC. The reaction mixture was poured into water and extracted with MTBE. The obtained organic phase was washed by 1N HCl and saturated brine, dried, filtered, concentrated to give 8.10 g Compound (QR16034-SM-002).

33.2 Preparation of Compound (QR16034-SM)
1 g Compound (QR16034-SM-002) was added with 26 mL diethyl ether, under nitrogen protection, stirred to dissolve, cooled to 0° C., added with 1.4 mL acetic acid, and then added with 7.34 g activated zinc powder in batches, and kept reacting at the same temperature until the end of the reaction which was confirmed by TLC. The reaction mixture was filtered, and the filtrate was concentrated, added with 1N HCl, extracted with EtOAc. The organic phase was washed by saturated brine, dried and concentrated to 1.02 g Compound (QR16034-SM).

33.3 Preparation of Compound (QR16034)
Referring to the preparation method of example (QR16026), Compound (QR16034) was obtained by replacing the starting material (16026-SM) with Compound (QR16034-SM). ESI-MS: 541.1.

33.4 Preparation of Compound (16034)

Referring to the preparation method of Compound (16001), Compound (QR16034) was reacted with an appropriate amount of base to give Compound (16034); ESI-MS: 541.1.

The preparation route of Compound (QR16034-SM) was as follows:

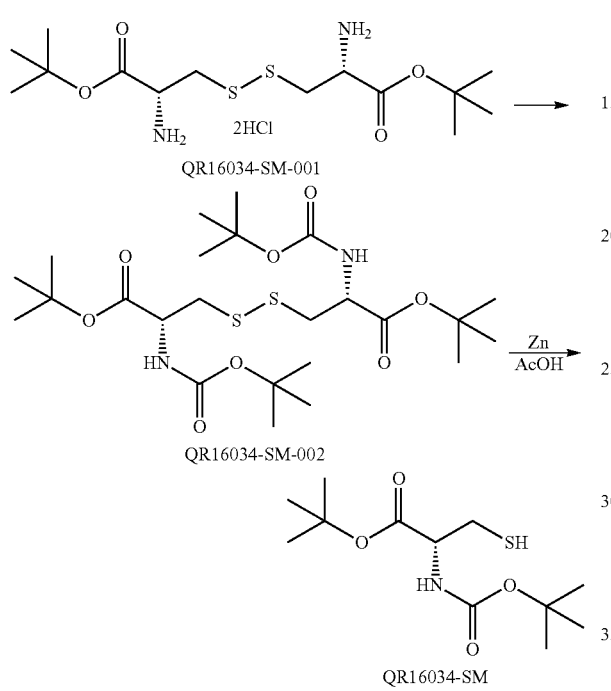

Example 34 Preparation of Compound (QR16035) and Compound (16035)

Referring to the preparation method of Compound (QR16034), Compound (QR16035) was obtained, ESI-MS: 555.2.

Referring to the preparation method of Compound (16001), Compound (QR16035) was reacted with an appropriate amount of base to give Compound (16035), ESI-MS: 555.2.

Example 35 Preparation of Compound (16036) and Compound (QR16036)

35.1 Preparation of Compound (16036-001)

The preparation method was carried out with reference to the preparation of Compound (16026-001) in which benzyl thioglycolate (CAS No. 7383-63-3) was used instead of the starting material 2-tert-butyl glycolate (CAS No. 50595-15-8).

35.2. Preparation of Compound (16036-002)

Compound (16036-001) was used as a starting material to obtain the title compound, referring to the preparation method of Compound (16026-002).

35.3. Preparation of Compound (16036)

15 mL methanol and 0.001 mol Compound (16036-002) were added into a reaction flask, stirred and dissolved, added with 0.1 g Pd/C catalyst, kept reacting under hydrogen at 25° C. overnight. The reaction mixture was filtered, and the filtrate was concentrated to obtain Compound (16036). ESI-MS: 512.1.

Referring to the preparation method of Compound (QR16046), the corresponding sodium salt (QR16036) was obtained; ESI-MS: 512.1.

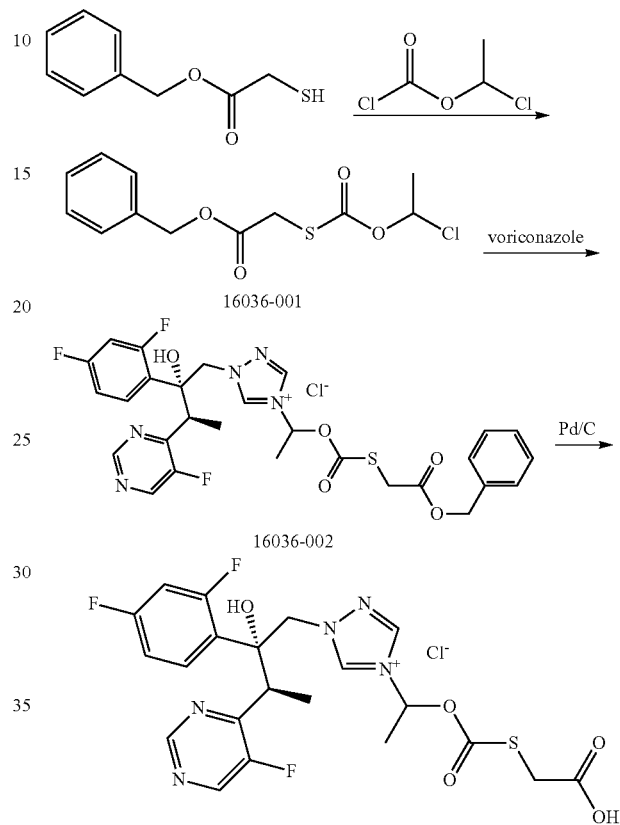

Example 36 Preparation of Compound (16037)

36.1 Preparation of Compound (16037-001)

16037-SM (CAS No. 127084-56-4, preparation method referring to Minch, Britt A., et al. "Octakis(2-benzyloxyethylsulfanyl) Copper (II) Phthalocyanine: A New Liquid Crystalline Discotic Material with Benzyl-Terminated, Thioether-Linked Side Chains. "Chemical of Materials 17.7 (2005)) was used as a starting material to obtain the title product, referring to the preparation method of Compound (16026-001).

36.2 Preparation of Compound (16037-002)

Compound (16037-001) was used as a reaction substrate to obtain the title compound, referring to the preparation of Compound (16026-002).

36.3 Preparation of Compound (16037)

15 mL methanol and 0.001 mol Compound (16037-002) were added into a reaction flask, stirred to dissolve, added with 0.1 g Pd/C catalyst, kept reacting under hydrogen at 25° C. overnight. The reaction solution was filtered, and the filtrate was concentrated to give 0.48 g Compound (16037), ESI-MS: 498.14.

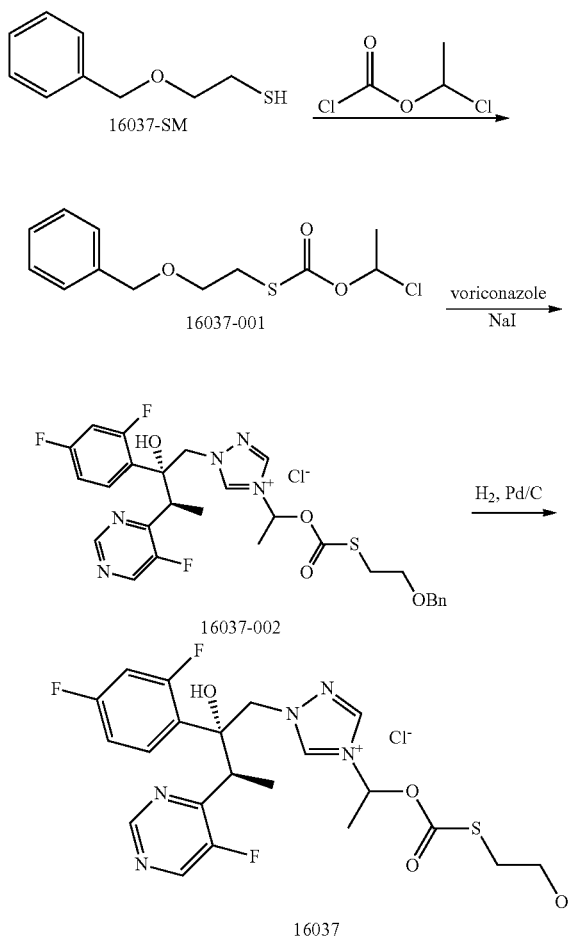

Example 37 Preparation of Compound (16038) and Compound (QR16038)

Referring to the preparation method of Compound (16026), Compound (16038) was obtained by replacing the starting material 2-tert-butyl glycolate (CAS No. 50595-15-8) with t-butyl glycinate (CAS No. 6456-74-2); ESI-MS: 495.2.

Compound (QR16038) was obtained referring to the preparation method of Compound (QR16046), ESI-MS: 495.2.

Example 38 Preparation of Compound (QR16039) and Compound (16039)

Referring to the preparation method of Compound (16026), the starting material 2-tertiary-butyl glycolate (CAS No. 50595-15-8) was replaced with tert-butyl (S)-2-tert-butoxycarbonylamino-4-aminobutyrate (CAS No. 190447-69-9) to give Compound (QR16039), ESI-MS: 538.2.

Referring to the preparation method of Compound (16001), the free compound (16039) was also obtained; ESI-MS: 538.2.

Example 39 Preparation of Compound (QR16040) and Compound (16040)

39.1 Preparation of Compound (QR16040-001)

10 g D-xylose (QR16040-SM) was added to 20 mL anhydrous methanol added with 0.01 eq. ammonium chloride, stirred (suspension) and cooled to 0° C.; The reaction mixture gradually clarified after ammonia gas was fed for 30 minutes. After ammonia gas was continuously fed for another 1 h, the reaction solution was cooled and crystallized to obtain 3 g solid product (QR16040-001).

39.2 Preparation of Compound (QR16040-002)

Under nitrogen protection, 15 g 2,2-dimethoxypropane, 40 mL anhydrous acetone were added, stirred, added with 1.6 eq. p-toluenesulfonic acid, stirred at room temperature for about 15 min, added with 3 g Compound (QR16040-001), stirred, precipitated a solid, and filtered to give 2.3 g Compound (QR 16040-002).

Preparation of 39.3 compound (QR16040-003)

0.01 mol Compound (QR16040-002) was dissolve in 50 mL dichloromethane, stirred under nitrogen protection, cooled to −15 to −18 OC, added with 0.024 mol N,N-diisopropylethylamine, stirred and cooled to −15 to −20 OC, added dropwise with 0.011 mol 1-chloroethyl chloroformate in dichloromethane (20 mL), and after that the reaction mixture was kept at a temperature of −15 to −20 OC for 16 h. The reaction mixture was used in the next reaction without isolation.

39.4 Preparation of Compound (QR16040-004)

While keeping the temperature of −15 to −20 OC, the above reaction mixture was added with 0.012 mol Boc-sarcosine, 0.003 mol DMAP, and 0.012 mol 1-ethyl-3-(3-dimethylaminopropyl) carbodiimide hydrochloride (EDCI·HCl), and then reacted for 2-3 h at the above temperature. The reaction mixture was then added with 50 mL 0.1N HCl, stirred, raised to room temperature, and separated to different liquid phases. The organic phase was washed with 0.1N HCl, saturated solution of sodium bicarbonate and brine, dried, filtered and concentrated to obtain 3.6 g crude product.

39.5 Preparation of Compound (QR16040-005)

The title compound was obtained referring to the preparation method of Compound (QR16032-002).

39.6 Preparation of Compound (QR16040)

The hydrochloride salt Compound (QR16040) was obtained referring to the preparation method of Compound (QR16032), ESI-MS: 640.2.

39.7 Preparation of Compound (16040)

Compound (16040) was obtained referring to the preparation method of Compound (16001), ESI-MS: 640.2.

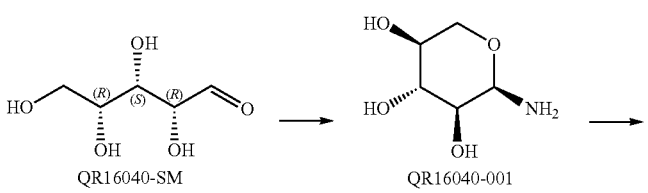

-continued
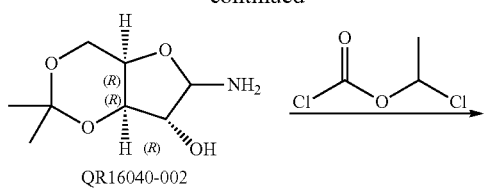
QR16040-002
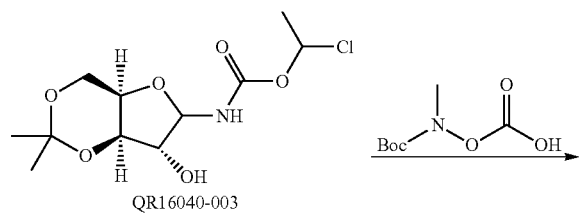
QR16040-003
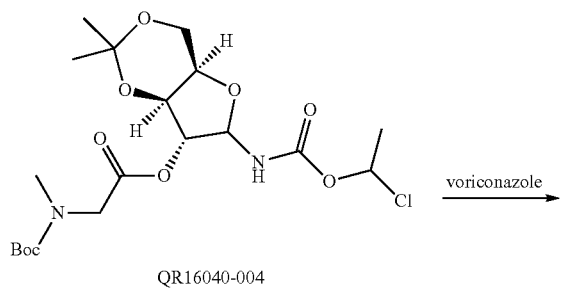
QR16040-004
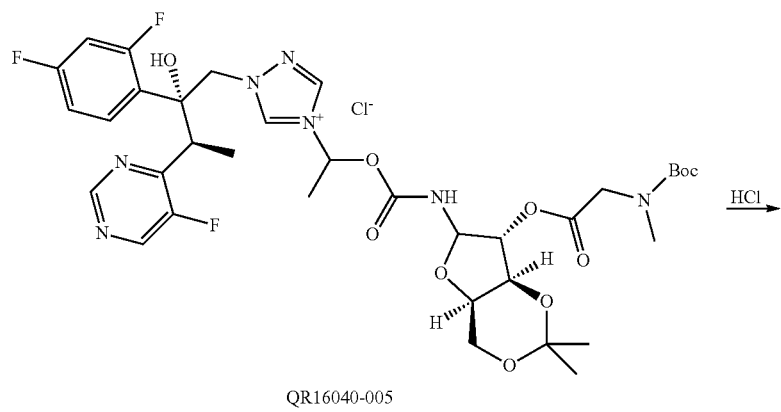
QR16040-005
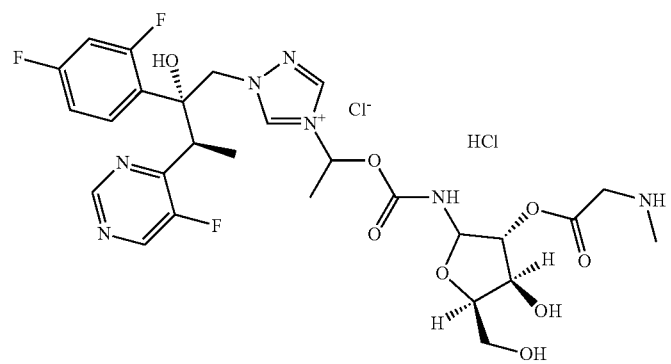
QR16040

77

Example 40 Preparation of Compound (QR16041) and Compound (16041)

Compound (QR 16041) was obtained referring to the preparation method of Compound (16026) in which the starting material 2-tert-butyl glycolate (CAS No. 50595-15-8) was replaced with tert-butyl N-(3-aminopropyl)carbamate (CAS No. 75178-96-0); ESI-MS: 494.2.

According to the above examples, Compound (QR16041) was reacted with an appropriate amount of base to give Compound (16041); ESI-MS: 494.2.

Example 41 Preparation of Compound (16043) and Compound (QR16043)

41.1 Preparation of compound (16043-001)

Under nitrogen protection, 3.3 g voriconazole was dissolved in 100 mL acetonitrile, added with 0.1 eq. sodium bromide and 1.2 eq. t-butyl chloroacetate, heated to 65-70° C. for 16 h under stirring. The end of the reaction was judged by TLC. The reaction mixture was cooled to room temperature and purified by column chromatography to give 1.5 g Compound (16043-001).

41.2 Preparation of Compound (16043)

0.8 g Compound (16043-001) was dissolved in 20 mL ethyl acetate at room temperature, stirred and dissolved, and added with a solution of hydrogen chloride in ethyl acetate (10 mL, 4 mol/L) dropwise at 0° C. After the addition was completed, the temperature of the reaction mixture was raised to room temperature under continuous stirring. The end of the reaction was judged by TLC. The reaction mixture was filtered to give 0.48 g Compound (16043), ESI-MS: 408.1.

41.3 Preparation of Compound (QR16043)

Compound (QR16043) was obtained referring to the preparation method of Compound (QR16042), ESI-MS: 408.1.

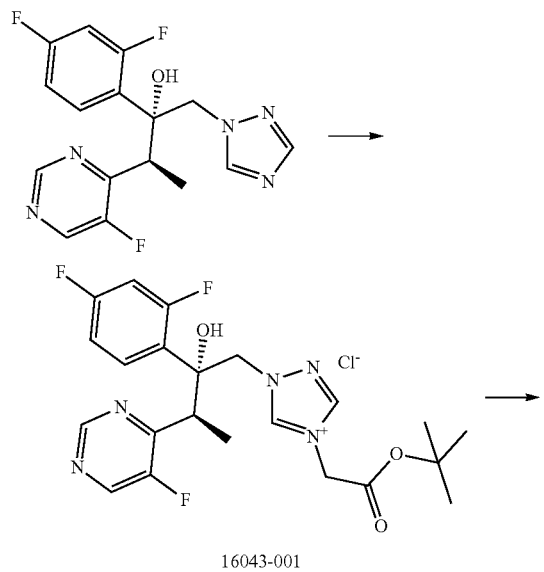

16043-001

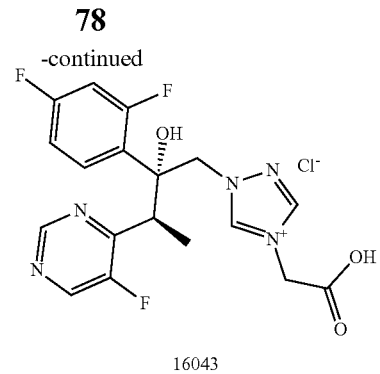

16043

Example 42 Preparation of Compound (16045) and Compound (QR16045)

Compound (16045) was obtained referring to the preparation of paragraphs 1.1 and 1.2 of Example 1, wherein Boc-glycine of Example 1 was replaced with dimethylglycine (CAS No. 1118-68-9) to give the compound (16045). ESI-MS: 643.3.

Compound (16045) was dissolved in 20 mL methanol, added with 3 eq. 4 N hydrochloric acid dropwise at room temperature, stirred and lyophilized to give the hydrochloride salt Compound (QR16045), which was determined by mass spectrometry and ion chromatography to as the target product; ESI-MS: 643.3.

Test of Biological Activity and Related Properties

Example I: Solubility Test of Compounds of the Present Disclosure

Experimental condition: 25±2° C.
Experimental instrument: Agilent 1260 HPLC
Dissolving medium: deionized water
Experimental method: 1 mg voriconazole and appropriate amount of each compound were weighed, placed in 1 ml deionized water separately, shaken vigorously for 30 s every 5 mins for 30 mins. The dissolution state of the mixture was observed, and the solubility of each compound was determined by HPLC using external calibration method. In the experiment, it was found that there was no significant difference in solubility between different onium salts of the same compound, such as QR16006, QR16008, SF16002, QR16011, QR16012 and QR16002, SF16001 and QR16001; SF16020 and QR16020. The solubility results of each compound were shown as follows:

TABLE 1

| results of solubility test | |
|---|---|
| Compound No. | Solubility (mg/mL) |
| Voriconazole | <1 |
| QR16001 | >50 |
| QR16002 | >50 |
| QR16003 | >50 |
| QR16004 | >50 |
| QR16005 | >50 |
| QR16006 | >50 |
| QR16007 | >50 |
| QR16008 | >50 |
| QR16009 | >50 |
| SF16002 | >50 |
| QR16011 | >50 |
| QR16012 | >50 |

TABLE 1-continued results of solubility test

| Compound No. | Solubility (mg/mL) |
|---|---|
| QR16013 | >50 |
| QR16014 | >50 |
| QR16015 | >50 |
| QR16016 | >50 |
| QR16017 | >50 |
| QR16018 | >50 |
| QR16019 | >50 |
| QR16020 | >50 |
| QR16021 | >50 |
| QR16022 | >50 |
| QR16023 | >50 |
| QR16024 | >50 |
| QR16025 | >50 |
| QR16028 | >50 |
| QR16029 | 14.2 |
| QR16030 | >50 |
| QR16032 | >50 |
| QR16033 | >50 |
| QR16034 | 12.5 |
| QR16040 | 16.8 |
| QR16042 | >50 |
| SF16001 | >50 |
| QR16045 | >50 |
| QR16046 | >50 |

According to the above data, the example compounds of the present disclosure have effects superior to voriconazole, and their solubility in pure water is significantly higher than that of voriconazole. This advantage makes it possible to avoid the safety risk associated with the use of sulfobutyl ether β-cyclodextrin as a solubilizer in the formulation.

Example II: Study of In Vitro Stability of the Compounds of the Present Disclosure The metabolic stability of the compounds of the present disclosure in human (rat) plasma and intestinal S9 in vitro were detected in this example. 990 μl of human (rat) plasma was taken from the human (rat) plasma reaction system, pre-incubated at 37° C. for 5 mins, and added with 10 μl mother liquor of the compound to initiate the reaction. The human (rat) intestinal S9 stability test was carried out by adding the sample in the order according to the following table and incubating in a 37° C. water bath. The two reaction systems were set up three samples in parallel, while each sample was taken in an amount of 100 μL at 1 min, 2 mins, 5 mins, 15 mins, and 30 mins after the reaction, added to the centrifuge tube containing 400 μL of 0° C. pre-cooled internal standard working fluid and terminated the reaction. The sample was mixed by vortex for 1 min, centrifuged at 10,000×g for 10 mins in a 4° C. pre-cooled high-speed centrifuge. The supernatant was taken for HPLC detection. The test results were calculated by a non-compartment model using WinNonlin (version 6.2 Pharsight, Mountain View, Calif.) to calculate the metabolic half-life.

Concentration of mother liquor of compounds: 1 mM

Reaction matrix: human (rat) plasma, intestinal S9 purchased from Shanghai Ruide Liver Disease Research Co., Ltd.

TABLE 2

Composition of the reaction system of each compound in human (rat) intestinal S9

| | composition | Volume (μL) | Initial concentration | Final concentration |
|---|---|---|---|---|
| | PBS buffer (pH 7.4) | 740 | 0.1M | 0.1M |
| | Intestinal S9 | 50 | 20 mg/mL | 1 mg/mL |
| | 37° C. pre-incubation for 5 min | | | |
| | Aqueous solution of the compound | 10 | 1 mM | 10 μM |
| | NADPH regeneration system | | | |
| 1 mL Human intestinal incubation system (rat) S9 | MgCl$_2$ | 200 | 100 mM | 5 mM |
| | NADP | | 20 mM | 1 mM |
| | Glucose-6-phosphate | | 200 mM | 10 mM |
| | Glucose-6-phosphate dehydrogenase | | 20 unit/mL | 1 unit/mL |

The metabolic half-lives of the compounds of the present disclosure in human (rat) plasma and intestinal S9 in vitro were detected in this example, wherein the half-lives of QR16003-QR16005, and QR16009 were similar, wherein QR16005 was shown as an example; the half-lives of QR16018, QR16019, QR16021-QR16023 were similar, wherein QR16022 was shown as an example; the half-lives of QR16024, QR16025, QR16032-QR16036, QR16038-QR16040 and QR16043 were similar, wherein QR16035 was shown as an example; the half-life of QR16026-QR16030, 16031 were similar, wherein QR16029 was shown as an example. In the experiment, it was also found that there was no significant difference in the experimental data of different onium salts of the same compound, such as QR16006, QR16008, SF16002, QR16011, QR16012 and QR16002; SF16001 and QR16001; SF16020 and QR16020. Therefore one experimental datum of such different onium salts of each compound was selected and listed in the following table.

TABLE 3

Metabolic half-life of each compound in human (rat) plasma and intestinal S9

| Compound | Human plasma $T_{1/2}$ (min) | Human intestinal S9 $T_{1/2}$ (min) | Rat plasma $T_{1/2}$ (min) | Rat intestinal S9 $T_{1/2}$ (min) |
|---|---|---|---|---|
| QR16001 | 1.56 ± 0.26 | 10.09 ± 1.75 | 1.23 ± 0.45 | 10.15 ± 2.65 |
| QR16002 | 0.76 ± 0.20 | 14.75 ± 2.16 | 0.89 ± 0.33 | 14.85 ± 4.25 |
| QR16005 | 6.15 ± 0.75 | 18.21 ± 2.04 | 8.25 ± 1.28 | 26.52 ± 3.69 |
| QR16008 | 9.49 ± 1.31 | 30.25 ± 4.90 | 10.58 ± 2.95 | 32.52 ± 7.82 |
| QR16013 | 1.91 ± 0.13 | 19.21 ± 1.32 | 1.25 ± 0.68 | 21.85 ± 6.59 |
| QR16014 | 0.83 ± 0.19 | 17.15 ± 2.25 | 0.87 ± 0.56 | 18.55 ± 5.69 |
| QR16015 | 2.05 ± 0.26 | 12.72 ± 1.72 | 1.58 ± 0.95 | 15.95 ± 4.96 |
| QR16016 | 2.12 ± 1.07 | 15.72 ± 0.98 | 1.95 ± 0.87 | 19.62 ± 3.69 |
| QR16017 | 0.95 ± 0.28 | 11.25 ± 2.21 | 0.78 ± 0.86 | 15.69 ± 6.95 |
| QR16020 | 1.44 ± 0.62 | 16.94 ± 1.62 | 1.25 ± 0.39 | 20.95 ± 6.66 |
| QR16022 | 26.01 ± 2.39 | 43.22 ± 1.03 | 29.52 ± 7.85 | 55.95 ± 10.28 |

TABLE 3-continued

Metabolic half-life of each compound in human (rat) plasma and intestinal S9

| Compound | Human plasma $T_{1/2}$ (min) | Human intestinal S9 $T_{1/2}$ (min) | Rat plasma $T_{1/2}$ (min) | Rat intestinal S9 $T_{1/2}$ (min) |
|---|---|---|---|---|
| QR16029 | 27.56 ± 2.43 | 40.56 ± 2.34 | 22.85 ± 8.88 | 53.52 ± 8.55 |
| QR16035 | 14.15 ± 3.75 | 29.12 ± 2.09 | 11.85 ± 3.77 | 35.62 ± 8.12 |
| 16037 | 7.75 ± 0.56 | 10.75 ± 1.97 | 7.65 ± 0.78 | 15.96 ± 6.88 |
| QR16042 | 10.47 ± 2.36 | 25.28 ± 4.75 | 11.28 ± 2.39 | 23.52 ± 8.55 |
| QR16045 | 8.95 ± 0.12 | 32.97 ± 8.45 | 8.88 ± 0.55 | 27.85 ± 6.58 |

It can be seen from the data in the table that the compounds of the present disclosure have similar half-lives in plasma of both human and rat and in two kinds of intestinal S9, and the results of pharmacological experiments in rats have reference significance for the study of the effects of drugs in human.

Example III: Test of Solid Stability of the Compound of the Present Disclosure

Experimental conditions: 25° C.±2° C., relative humidity 60%±2%
Experimental instrument: Agilent 1260 HPLC; chamber for stability test
Experimental method: each compound of the present disclosure was packaged (the inner packaging material was a penicillin bottle; the outer packaging material was a double-layer aluminum foil bag, and a desiccant was added inside and outside the package), placed in the chamber for stability test, at a temperature of 25° C.±2° C. and a relative humidity of 60%±2%. The degradation situation of the compounds for 30 days was examined. The contents of total impurities before and after 30 days of each compound were compared and the results were as follows:

TABLE 4

Results of solid stability test

| Compound No. | Content increase of total impurity (25° C., placed for 30 days) | Compound No. | Content increase of total impurity (25° C., placed for 30 days) |
|---|---|---|---|
| QR16001 | 0.53% | SF16013 | 0.48% |
| QR16002 | 1.02% | SF16014 | 0.36% |
| QR16003 | 1.37% | SF16015 | 0.32% |
| QR16006 | 1.14% | QR16024 | 2.84% |
| QR16007 | 0.73% | QR16025 | 1.57% |
| QR16008 | 1.05% | QR 16028 | 1.52% |
| QR16009 | 0.71% | QR 16029 | 1.17% |
| SF16002 | 0.67% | QR 16030 | 0.94% |
| QR16011 | 0.96% | 16031 | 0.97% |
| QR16012 | 0.92% | QR16035 | 1.21% |
| QR16013 | 0.42% | QR16036 | 1.35% |
| QR16014 | 0.53% | 16037 | 2.15% |
| QR16015 | 0.39% | QR 16039 | 1.22% |
| QR16016 | 0.62% | QR 16040 | 2.84% |
| QR16017 | 0.55% | SF16001 | 0.37% |
| QR16018 | 1.15% | QR 16045 | 2.23% |
| QR16019 | 0.88% | QR 16046 | 0.79% |
| QR16020 | 0.56% | SF16020 | 0.62% |
| QR16021 | 1.14% | SF16016 | 0.49% |
| QR16023 | 2.63% | SF16017 | 0.46% |

By analyzing the above data, it can be shown that the compounds of the present disclosure exhibited good stability when being placed at a temperature of 25° C.±2° C. and a relative humidity of 60%±2% for 30 days, wherein QR16001, QR16002, QR16013, QR16014, QR16015, QR16016, QR16017, QR16020 and the like, as well as their different salt types such as hydrochloride or sulfate, all exhibited better stability.

Example IV: Pharmacokinetics (PK) Study of Intravenous Administration of the Compounds of the Present Disclosure Dosage for administration: 2.5 mg/kg (calculated as voriconazole)
Dosing volume for administration: 2.5 ml/kg
Drug concentration: 1 mg/mL (calculated as voriconazole)
Solvent medium for administration: physiological saline; since voriconazole was insoluble in the medium (physiological saline), commercially available voriconazole injection (Pfizer, product batch number Z467001) was used in the study as a control, that is, voriconazole (cyclodextrin) with sulfobutylether-β-cyclodextrin as a solubilizer was used.
Route of administration: tail vein injection
Experimental animals: SD rats, SPF grade, weighing 180-220 g, half male and half female; the SD rats were randomized into groups of 6 animals each, three males and three females in each group.
Experimental method: Blood samples were collected at different time points after tail vein administration, and the plasma concentrations of voriconazole were measured.
Among the PK parameters of voriconazole in plasma: the PK parameters of QR16003-QR16005 and QR16009 were similar, wherein QR16004 was shown as an example; the PK parameters of QR16018, QR16019, QR16021-QR16023 were similar, wherein QR16021 was shown as an example; the PK parameters of QR16024, QR16025, QR16032-QR16036, QR16038-QR16040 and QR16043 were similar, wherein QR16035 was shown as an example; the PK parameters of QR16026-QR16030 and 16031 compounds were similar, wherein QR16028 was shown as an example. In the experiment, it was found that there was no significant difference in experimental data of different onium salts of the same compound, such as QR16006, QR16008, SF16002, QR16011, QR16012 and QR16002, SF16001 and QR16001; SF16020 and QR16020. Therefore one experimental datum of such different onium salts of each compound was selected and listed in the following table.

TABLE 5

Main pharmacokinetic parameters of single intravenous administration of each compound in rats

| Compound | $T_{1/2}$ (h) | $AUC_{last}$ (ng/mL*h) |
|---|---|---|
| Voriconazole | — | — |
| Voriconazole (cyclodextrin) | 2.58 ± 1.25 | 10856 ± 2351 |
| QR16001 | 2.14 ± 0.98 | 10515 ± 1985 |
| QR16002 | 1.95 ± 1.21 | 10152 ± 3280 |
| QR16004 | 2.92 ± 1.62 | 9586 ± 2352 |

TABLE 5-continued

Main pharmacokinetic parameters of single intravenous administration of each compound in rats

| Compound | $T_{1/2}$ (h) | $AUC_{last}$ (ng/mL*h) |
|---|---|---|
| QR16007 | 2.88 ± 1.22 | 10278 ± 3225 |
| QR16013 | 2.25 ± 0.85 | 10252 ± 4526 |
| QR16014 | 1.98 ± 0.88 | 10156 ± 3654 |
| QR16015 | 2.85 ± 1.78 | 10526 ± 2695 |
| QR16016 | 2.65 ± 0.88 | 10477 ± 1854 |
| QR16017 | 2.78 ± 0.75 | 10259 ± 3285 |
| QR16020 | 2.45 ± 0.75 | 10122 ± 3525 |
| QR16021 | 2.97 ± 1.12 | 7056 ± 2532 |
| QR16028 | 2.55 ± 0.85 | 7256 ± 3251 |
| QR16035 | 2.74 ± 0.81 | 8256 ± 1256 |
| 16037 | 2.47 ± 0.75 | 9120 ± 3254 |
| QR16042 | 2.88 ± 0.21 | 7898 ± 4251 |
| QR16045 | 2.74 ± 0.78 | 8586 ± 1856 |

$T_{1/2}$: half-life,
$AUC_{last}$: area under the time curve;
"—": The parameter could not be calculated because voriconazole was not detected.

It can be seen from the data in the table that voriconazole is not detected in the control group of voriconazole dissolved in physiological saline. However, after intravenous administration to rats of the compound group of the present disclosure, the exposures of voriconazole were much higher than that of voriconazole dissolved in physiological saline, but similar with the positive drug voriconazole (cyclodextrin), indicating that most of the original drug has been converted to voriconazole after intravenous administration, which can avoid the safety risk caused by β-cyclodextrin used as a solubilizer.

Example V: Pharmacokinetics (PK) Study of Gastrointestinal Administration of the Compounds of the Present Disclosure Dosage for administration: 2.5 mg/kg (calculated as voriconazole)
Dosing volume for administration: 10 ml/kg
Drug concentration: 0.25 mg/mL
Solvent medium for administration: except for the positive voriconazole group using CMC-Na, the other groups using normal saline
Route of administration: gavage
Experimental animals: SD rats, SPF grade, weighing 180-220 g, half male and half female; the SD rats were randomized into groups of 6 animals each, three males and three females in each group.
Experimental method: After oral gavage, blood samples were collected at different time points to detect the plasma concentration of voriconazole, and the pharmacokinetic parameters of voriconazole were obtained: the PK parameters of QR16003-QR16005, QR16009 and QR16007 were similar, wherein QR16009 was shown as an example; the PK parameters of QR16018-QR16019, QR16021-QR16025 compounds were similar, wherein QR16023 was shown as an example; the PK parameters of QR16026-QR16030, 16031, QR16046 were similar, wherein QR16030 was shown as an example; the PK parameters of QR16032-QR16036, QR16038-QR16041, QR16043 were similar, wherein QR16036 was shown as an example. It was also found that there were no significant differences in PK parameters of different onium salts of the same compound, such as QR16006, QR16008, SF16002, QR16011, QR16012 and QR16002, SF16001 and QR16001; SF16020 and QR16020. Therefore one experimental datum of such different onium salts of each compound was selected and listed in the following table.

TABLE 6

Main pharmacokinetic parameters of single gastrointestinal administration of rats in each compound

| Compound | $C_{max}$ (ng/mL) | $T_{1/2}$ (h) | $AUC_{last}$ (ng/mL*h) |
|---|---|---|---|
| Voriconazole (CMC-Na) | 412 ± 102 | 2.95 ± 1.65 | 4252 ± 1235 |
| QR16001 | 789 ± 362 | 3.21 ± 1.28 | 8562 ± 1125 |
| QR16002 | 895 ± 178 | 2.65 ± 0.58 | 8654 ± 1085 |
| QR16008 | 825 ± 256 | 2.65 ± 0.58 | 8745 ± 2365 |
| QR16009 | 925 ± 121 | 1.98 ± 0.87 | 7225 ± 1310 |
| QR16013 | 895 ± 178 | 1.95 ± 0.77 | 8855 ± 2152 |
| QR16014 | 1022 ± 365 | 2.88 ± 0.85 | 8332 ± 2996 |
| QR16015 | 996 ± 365 | 2.78 ± 1.23 | 8144 ± 1468 |
| QR16016 | 885 ± 344 | 2.24 ± 1.25 | 8332 ± 3254 |
| QR16017 | 952 ± 421 | 2.95 ± 1.25 | 8695 ± 2958 |
| QR16020 | 815 ± 365 | 2.45 ± 0.68 | 8562 ± 2586 |
| QR16023 | 358 ± 105 | 2.75 ± 1.41 | 4553 ± 1252 |
| QR16030 | 362 ± 152 | 2.54 ± 1.05 | 4324 ± 1362 |
| QR16036 | 625 ± 214 | 2.62 ± 0.78 | 5954 ± 1895 |
| 16037 | 859 ± 358 | 2.78 ± 0.74 | 8562 ± 1895 |
| QR16042 | 785 ± 325 | 2.58 ± 1.21 | 6656 ± 1456 |
| QR16045 | 562 ± 158 | 2.59 ± 0.88 | 7859 ± 2256 |

$C_{max}$: peak of drug blood concentration,
$T_{1/2}$: half-life,
$AUC_{last}$: area under the time curve The above experimental results showed that the exposures of voriconazole after gastrointestinal administration of the compounds in rats were higher than or similar as that of the positive drug voriconazole (CMC-Na), indicating that most of the compound of the present disclosure are converted to voriconazole, and have high bioavailabilities.

Example VI: Experimental Study on the Effect of Intravenous Administration of the Compound of the Present Disclosure Against Systemic Fungal Infection in Mice 1. Experimental Material
1.1 Experimental Instruments
Multiskan MK3 type enzyme labeling detector, water-blocking electrothermal constant temperature incubator, ZQ-F160 full temperature shaking incubator, MJX type intelligent mold incubator, SW-CT-IF type ultra-cleaning workbench, ultraviolet spectrophotometer.
1.2 Experimental Reagents
Dimethyl sulfoxide, Sabouraud Dextrose Agar solid medium (SDA).
1.3 Experimental Animals
ICR mice, weighing 18-22 g, male, provided by the Hubei Experimental Animal Center.
1.4 Experimental Strain
The standard strain *Candida albicans* was purchased from the American Type Culture Collection, and the strain number was ATCC10231.
2. Experimental Method
Before the experiment, a small amount of *Candida albicans* was picked from the SDA medium preserved at 4° C. by inoculation circle, and inoculated into 1 ml YPD (Yeast Extract Peptone Dextrose Medium, the same below) culture medium, under shake cultivation at 30° C., 200 rpm, activated for 16 hours to make the fungus in the late stage of the exponential growth phase. Blood cell counting plate was used to count. The concentration of the broth was adjusted to $1*10^3$-$5*10^3$ CFU/ml with RPMI1640 (Roswell Park Memorial Institute 1640, the same below) culture medium. The *Candida albicans* monoclone on the SDA plate was picked and inoculated into 1 ml YPD medium, cultured at 35° C., 200 rpm for 16 hours to the late exponential growth phase, 1% of which was then inoculated in fresh medium for 6 hours, centrifuged at 1000×g for 5 mins, washed three times with saline until the supernatant was colorless, while hemocytometer was used to count. The cell concentration was adjusted to $5*10^6$/ml. The tail vein injection of 0.1 ml/10 g was carried out to cause a systemic fungal infection in mice. The mice were randomized into groups of 10 each. Since voriconazole was insoluble in vehicle (physiological saline), the mice of the voriconazole group in the test were injected a commercially available voriconazole (Pfizer, product lot number Z467001), that is, sulfobutyl ether-β-cyclodextrin used as a solubilizer, while other groups used physiological saline as a solvent. After establishing a systemic fungal infection model in mice for 2 hours, each administration group was administered with 5 mg/kg (calculated as voriconazole) drug in the tail vein, with the volume for administration of 0.1 ml/10 g. The mice in the model group were administered 0.1 ml/10 g of 0.9% sodium chloride solution, once daily, for 5 consecutive days. The death situation of the mice was inspected and the survival time was recorded. After a total of 7 days of observation, all dead mice were treated with fire using ethanol.

3. Experimental Results

The pharmacodynamic data of the intravenous administration of the compound of the present disclosure against systemic fungal infection in mice were shown in the following table. Wherein, the pharmacodynamic data of QR16003-QR16005, QR16009, QR16024-QR16030, QR16032-QR16033, QR16038-QR16043 and QR16046 were similar, wherein QR16004 was shown as an example; the pharmacodynamic data of QR16007, QR16018-QR16019, QR16021-QR16023, QR16040-QR16041 and QR16045 were similar, wherein QR16007 was shown as an example; the pharmacodynamic data of 16031, QR16034-QR16036, and 16037 were similar, wherein 16037 was shown as an example. It was found that in this experiment different onium salts of the same compound had similar pharmacodynamic data. For example the pharmacodynamic data of QR16006, QR16008, SF16002, QR16011 and QR16012 were similar to that of QR16002; the pharmacodynamic data of SF16001 was similar to that of QR16001; the pharmacodynamic data of SF16020 and QR16020 were similar. Therefore one experimental datum of such different onium salts of each compound was selected and listed in the following table.

TABLE 7

Systemic fungal infection (intravenous administration): survival rate of mice in each group after administration (%)

| Group | Dose (mg/kg) | Time (day) | | | | | | |
|---|---|---|---|---|---|---|---|---|
| | | 1 | 2 | 3 | 4 | 5 | 6 | 7 |
| Solvent group | — | 90% | 60% | 30% | 20% | 20% | 0% | 0% |
| voriconazole (β-cyclodextrin) | 5 | 100% | 100% | 100% | 100% | 100% | 100% | 90% |
| QR16001 | 5 | 100% | 100% | 100% | 100% | 100% | 100% | 90% |
| QR16002 | 5 | 100% | 100% | 100% | 100% | 100% | 90% | 90% |
| QR16004 | 5 | 100% | 100% | 100% | 90% | 90% | 80% | 80% |
| QR16007 | 5 | 100% | 100% | 100% | 100% | 100% | 90% | 90% |
| QR16013 | 5 | 100% | 100% | 100% | 100% | 90% | 90% | 90% |
| QR16014 | 5 | 100% | 100% | 100% | 90% | 90% | 90% | 90% |
| QR16015 | 5 | 100% | 100% | 100% | 100% | 100% | 90% | 90% |
| QR16016 | 5 | 100% | 100% | 100% | 100% | 100% | 90% | 90% |
| QR16017 | 5 | 100% | 100% | 100% | 100% | 100% | 100% | 90% |
| QR16020 | 5 | 100% | 100% | 100% | 100% | 90% | 90% | 90% |
| 16037 | 5 | 100% | 100% | 90% | 90% | 90% | 80% | 80% |

It can be seen from the data in the table that after 7 days of administration, the survival rates of the groups administrated with the compounds according to the present disclosure were significantly higher than that of the solvent group. Among the data, the survival rates of the mice on the 7th day in QR16001, QR16002, QR16007, QR16013, QR16014, QR16015, QR16016, QR16017 and QR16020 groups were similar with that of the mice in the positive drug voriconazole group, indicating that the efficacy of the compounds of the present disclosure is comparable to that of voriconazole, thereby having good efficiency. It is true that the survival rates of the mice on the 7th day of QR16004 and 16037 groups were slightly lower than that of the positive drug voriconazole group; however, in the voriconazole group of this experiment, voriconazole is in the form of commercially available voriconazole injection, which is solubilized with sulfobutylether-β-Cyclodextrin, whereas the compounds of the present disclosure were all dissolved in physiological saline, thereby avoiding the safety risk caused by β-cyclodextrin used as a solubilizer.

Example VII: Experimental Study on the Effect of the Compound by Gastrointestinal Administration of the Present Disclosure on Systemic Fungal Infection in Mice 1. Experimental Material 1.1 Experimental Instruments Multiskan MK3 type enzyme labeling detector, water-blocking electrothermal constant temperature incubator, ZQ-F160 full temperature shaking incubator, MJX type intelligent mold incubator, SW-CT-IF type ultra-cleaning workbench, ultraviolet spectrophotometer.

1.2 Experimental Reagents

Dimethyl sulfoxide, Sabouraud dextrose agar solid medium.

1.3 Experimental Animals

ICR mice, weighing 18-22 g, male, provided by the Hubei Experimental Animal Center.

1.4 Experimental strain

The standard strain *Candida albicans* was purchased from the American Type Culture Collection, and the strain number was ATCC10231.

2. Experimental Method

Before the experiment, a small amount of *Candida albicans* was picked from the SDA medium preserved at 4° C. by inoculation circle, inoculated into 1 ml of YPD culture medium, and cultured at 30° C. while being shaken at 200 rpm for 16 hours to make the fungus in the late stage of exponential growth. Blood cell counting plate was used to count, and the concentration of the broth was adjusted to $1*10^3$–$5*10^3$ CFU/ml with RPMI1640 medium. The *Candida albicans* monoclone on the SDA plate was picked, inoculated into 1 ml YPD medium, cultured at 35° C., 200 rpm for 16 hours to the late exponential growth phase, 1% of which was then inoculated in fresh medium for 6 hours, centrifuged at 1000×g for 5 mins, washed three times with saline until the supernatant was colorless, while hemocytometer was used to count. The cell concentration was adjusted to $5*10^6$/ml. The tail vein injection of 0.1 ml/10 g was carried out to cause a systemic fungal infection in mice. The mice were randomized into groups of 10 each. Voriconazole used was in the form of a suspension prepared with CMC-Na (Shanghai Panhong Chemical Technology Co., Ltd.), while other tested drugs were dissolved in saline and sonicated until clarified for administration. After establishing a systemic fungal infection model in mice for 2 hours, each group was administered by gavage with 5 mg/kg (calculated as voriconazole) drug, with the volume for administration of 0.1 ml/10 g. The mice in the model group were administered 0.1 ml/10 g of 0.9% sodium chloride solution, once daily, for 5 consecutive days. The death situation of the mice was inspected and the survival time was recorded. After a total of 7 days of observation, all dead mice were treated with fire using ethanol.

3. Experimental Results

The pharmacodynamic data of the compound of the present disclosure administered by gavage against systemic fungal infection in mice were shown in the following table, wherein the pharmacodynamic data of QR16003-QR16005, QR16007, and QR16009 compounds were similar, wherein QR16009 was shown as an example; the pharmacodynamic data of QR16018-QR16019, QR16021-QR16025 were similar, wherein QR16023 was shown as an example; the pharmacodynamic data of QR16026-QR16030 and 16031 compound were similar, wherein QR16030 as an example; the pharmacodynamic data of QR16032-QR16036, QR16038-QR16041 and QR16043 were similar, wherein QR16036 was shown as an example; In the experiment, it was found that different onium salts of the same compound had comparable pharmacodynamic data. For example, the pharmacodynamic data of QR16006, QR16008, SF16002, QR16011 and QR16012 were similar with QR16002; the pharmacodynamic data of SF16001 was similar with QR16001; the pharmacodynamic data of SF16020 and QR16020 were similar. Therefore one experimental datum of such different onium salts of each compound was selected and listed in the following table.

TABLE 8

Systemic fungal infection (gavage): survival rate of mice in each group after administration (%)

| Group | Dose (mg/kg) | Time (day) | | | | | | |
|---|---|---|---|---|---|---|---|---|
| | | 1 | 2 | 3 | 4 | 5 | 6 | 7 |
| Solvent group | — | 90% | 80% | 40% | 20% | 10% | 0% | 0% |
| Voriconazole (CMC-Na) | 5 | 100% | 100% | 90% | 80% | 60% | 50% | 50% |
| QR16001 | 5 | 100% | 100% | 100% | 100% | 90% | 80% | 80% |
| QR16002 | 5 | 100% | 100% | 100% | 100% | 90% | 80% | 80% |
| QR16008 | 5 | 100% | 100% | 100% | 100% | 90% | 80% | 80% |
| QR16009 | 5 | 100% | 80% | 80% | 70% | 70% | 70% | 70% |
| QR16013 | 5 | 100% | 100% | 90% | 90% | 80% | 80% | 80% |
| QR16014 | 5 | 100% | 100% | 100% | 100% | 90% | 90% | 80% |
| QR16015 | 5 | 100% | 100% | 100% | 100% | 100% | 80% | 80% |
| QR16016 | 5 | 100% | 100% | 90% | 90% | 90% | 90% | 80% |
| QR16017 | 5 | 100% | 100% | 90% | 90% | 90% | 90% | 80% |
| QR16020 | 5 | 100% | 90% | 90% | 90% | 90% | 90% | 80% |
| QR16023 | 5 | 100% | 90% | 70% | 70% | 60% | 60% | 50% |
| QR16030 | 5 | 100% | 90% | 80% | 70% | 60% | 50% | 50% |
| QR16036 | 5 | 100% | 90% | 80% | 80% | 70% | 60% | 60% |
| 16037 | 5 | 100% | 100% | 100% | 100% | 90% | 80% | 80% |
| QR16042 | 5 | 100% | 100% | 90% | 90% | 80% | 70% | 70% |
| QR16045 | 5 | 100% | 100% | 90% | 90% | 90% | 90% | 80% |

It can be seen from the data in the above table that after 7 days administration, the amounts of corneal bacteria in the mice of the compound groups according to the present disclosure were greatly reduced as compared with that of the solvent group, indicating the therapeutic effect of the compounds of the present disclosure was very significant. The survival rates of mice on the 7th day of most of the compound groups were higher than that of the positive drug voriconazole group, indicating that the pharmaceutical effect of these compounds was superior to that of the voriconazole suspension prepared with CMC-Na, and the survival rates of mice on the 7th day of QR16023 and QR16030 groups were same with the positive drug voriconazole group, proving that their efficacy were equivalent to the voriconazole suspension prepared with CMC-Na.

The invention claimed is:

1. A compound of formula (I), and a racemate, a stereoisomer, a tautomer, an oxynitride, or a pharmaceutically acceptable salt thereof:

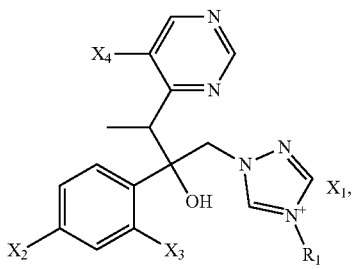

(I)

wherein, $R_1$ is selected from

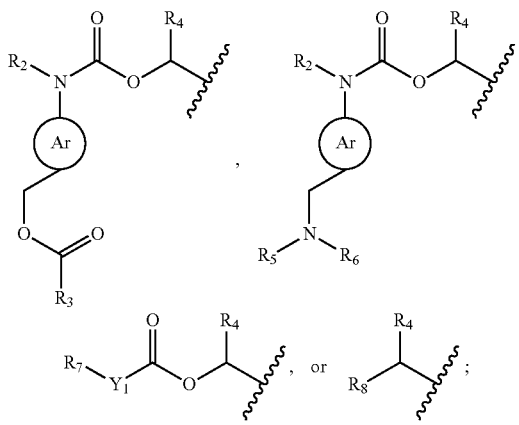

$X_1$ is a pharmaceutically acceptable anion;

$X_2$, $X_3$, $X_4$ are independently selected from F, Cl, Br, and I;

$R_2$ is independently selected from H, unsubstituted $C_{1-40}$ alkyl, and $C_{1-40}$ alkyl substituted by one or more $R_a$;

$R_4$ independently selected from unsubstituted $C_{1-40}$ alkyl and $C_{1-40}$ alkyl substituted by one or more $R_a$;

$R_3$ is selected from unsubstituted $C_{1-40}$ alkyl and $C_{1-40}$ alkyl substituted by one or more $R_b$;

$R_5$ and $R_6$ are the same or different, independently selected from H, a first group of functional groups that are unsubstituted, and the first group of functional groups that are substituted by one or more $R_m$, wherein the first group of functional groups consists of $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, and —C(O)$R_f$;

Ar is selected from a second group of functional groups that are unsubstituted and the second group of functional groups that are substituted by one or more $R_c$, wherein the second group of functional groups consists of $C_{6-20}$ aryl, 5-20 membered heteroaryl, wherein the 5-20 membered heteroaryl comprises 1-5 heteroatoms independently selected from N, O, and S;

$R_7$ is selected from a third group of functional groups that are unsubstituted and the third group of functional groups that are substituted by one or more $R_c$, wherein the third group of functional groups consists of $C_{1-40}$ alkyl, $C_{3-20}$ cycloalkyl, 3-20 membered heterocyclyl, $C_{6-20}$ aryl, 5-20 membered heteroaryl, —Y$_2$P(O)(OM$_1$)(OM$_2$), —C(O)R$_f$, and —(CH$_2$CH$_2$O)$_z$—R$_b$;

$R_8$ is selected from H, a fourth group of functional groups that are unsubstituted, and the fourth group of functional groups that are substituted by one or more $R_b$, wherein the fourth group of functional groups consists of $C_{1-40}$ alkyl, $C_{3-20}$ cycloalkyl, 3-20 membered heterocyclyl, $C_{6-20}$ aryl, 5-20 membered heteroaryl, —NR$_d$R$_e$, —CONR$_d$R$_e$, —C(O)Y$_2$R$_f$, —Y$_2$C(O)R$_f$, —Y$_2$P(O)(OM$_1$)(OM$_2$), and —Y$_2$S(O)$_2$OM$_3$;

$Y_1$ and $Y_2$ are the same or different, independently selected from a chemical bond, —O—, —S—, a fifth group of functional groups that are unsubstituted, and the fifth group of functional groups that are substituted by one or more $R_a$, wherein the fifth group of functional groups consists of —NH—, $C_{1-40}$ alkyl, $C_{1-40}$ alkoxy, $C_{3-20}$ cycloalkyl, 3-20 membered heterocyclyl, $C_{6-20}$ aryl, 5-20 membered heteroaryl, and —(CH$_2$CH$_2$O)$_j$—;

each $R_a$ is the same or different, independently selected from H, $C_{1-40}$ alkyl, $C_{1-40}$ alkoxy, $C_{2-40}$ alkenyl, $C_{2-40}$ alkynyl, $C_{3-20}$ cycloalkyl, F, Cl, Br, I, OH, SH, CN, =O, —NR$_d$R$_e$, —C(O)Y$_2$R$_f$, —Y$_2$C(O)R$_f$, —CONR$_d$R$_e$—, —Y$_2$P(O)(OM$_1$)(OM$_2$), and —Y$_2$S(O)$_2$OM$_3$;

each $R_b$ is the same or different, independently selected from H, F, Cl, Br, I, OH, SH, CN, a sixth group of functional groups that are unsubstituted, and the sixth group of functional groups that are substituted by one or more $R_a$, wherein the sixth group of functional groups consists of $C_{1-40}$ alkyl, $C_{1-40}$ alkoxy, $C_{2-40}$ alkenyl, $C_{2-40}$ alkynyl, $C_{3-20}$ cycloalkyl, $C_{3-20}$ cycloalkyloxy, 3-20 membered heterocyclyl, 3-20 membered heterocyclyloxy, $C_{6-20}$ aryl, $C_{6-20}$ aryloxy, 5-20 membered heteroaryl, 5-20 membered heteroaryloxy, —[(CH$_2$)$_n$O]$_m$—, —NR$_d$R$_e$, —CONR$_d$R$_e$, —C(O)Y$_2$R$_f$, —Y$_2$C(O)R$_f$, —Y$_2$P(O)(OM$_1$)(OM$_2$), and —Y$_2$S(O)$_2$OM$_3$, with the proviso that $R_b$ is not $C_{1-40}$ alkyl in (CH$_2$CH$_2$O)$_z$—R$_b$;

each $R_c$ is the same or different, independently selected from F, Cl, Br, I, OH, SH, CN, a seventh group of functional groups that are unsubstituted, and the seventh group of functional groups that are substituted by one or more $R_a$, wherein the seventh group of functional groups consists of $C_{1-40}$ alkyl, $C_{1-40}$ alkoxy, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, $C_{3-20}$ cycloalkyloxy, 3-20 membered heterocyclyloxy, $C_{6-20}$ aryloxy, 5-20 membered heteroaryloxy, —NR$_d$R$_e$, —CONR$_d$R$_e$, —C(O)Y$_2$R$_f$, —Y$_2$C(O)R$_f$, —Y$_2$P(O)(OM$_1$)(OM$_2$), and —Y$_2$S(O)$_2$OM$_3$;

each $R_d$ and $R_e$ are the same or different, independently selected from H, the eighth group of functional groups that are unsubstituted, and the eighth group of functional groups that are substituted by one or more $R_m$, wherein the eighth group of functional groups consists of $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, —CONR$_f$R$_g$, —C(O)Y$_2$R$_f$, —Y$_2$C(O)R$_f$, —Y$_2$P(O)(OM$_1$)(OM$_2$), and —Y$_2$S(O)$_2$OM$_3$;

each $R_f$ and $R_g$ are the same or different, independently selected from H, a ninth group of functional groups that are unsubstituted, and the ninth group of functional groups that are substituted by one or more $R_m$, wherein the ninth group of functional groups consists of $C_{1-40}$ alkyl, $C_{2-40}$ alkenyl, $C_{2-40}$ alkynyl, $C_{3-20}$ cycloalkyl, —COOH, 3-20 membered heterocyclyl, $C_{6-20}$ aryl, and 5-20 membered heteroaryl;

each $R_m$ is the same or different, independently selected from H, F, Cl, Br, I, OH, SH, CN, a tenth group of functional groups that are unsubstituted, and the tenth group of functional groups that are substituted by one or more $R_a$ wherein the tenth group of functional groups consists of $C_{1-40}$ alkyl, $C_{1-40}$ alkoxy, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, —$NR_dR_e$, —$CONR_dR_e$, —$C(O)Y_2R_f$, —$Y_2C(O)R_f$, —$Y_2P(O)(OM_1)(OM_2)$, and —$Y_2S(O)_2OM_3$;

$M_1$, $M_2$, and $M_3$ are the same or different, independently selected from H, unsubstituted $C_{1-40}$ alkyl, and $C_{1-40}$ alkyl substituted by one or more $R_b$; and n, m, j, and z are the same or different, independently selected from integers from 1 to 20, inclusive.

2. The compound, the racemate, the stereoisomer, the tautomer, the oxynitride, or the pharmaceutically acceptable salt thereof according to claim 1, wherein:

$X_1$ is selected from one or more monovalent anions, ½ of a polyvalent anion, ⅓ of a polyvalent anion, ⅔ of a polyvalent anion, and mixtures thereof; wherein $X_1$ is formed by ionization of inorganic or organic acids;

wherein the inorganic acid is selected from hydrochloric acid, hydrofluoric acid, hydrobromic acid, hydroiodic acid, sulfuric acid, pyrosulfuric acid, phosphoric acid, and nitric acid;

wherein the organic acid is selected from formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectic acid, persulfate, 3-phenylpropionic acid, picric acid, pivalic acid, 2-hydroxyethanesulfonic acid, itaconic acid, sulfamic acid, trifluoromethanesulfonic acid, lauryl sulfate, ethanesulfonic acid, benzenesulfonic acid, p-toluene sulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, algae acid, maleic acid, fumaric acid, D-gluconic acid, mandelic acid, ascorbic acid, glucoheptanoic acid, glycerol phosphate, aspartic acid, sulfosalicylic acid, hemisulfuric acid, and thiocyanic acid.

3. The compound, the racemate, the stereoisomer, the tautomer, the oxynitride, or the pharmaceutically acceptable salt thereof according to claim 1, wherein the pharmaceutically acceptable salt is selected from:

an alkali metal salt of the compound of formula (I), an alkaline earth metal salt of the compound of formula (I), an ammonium salt of the compound of formula (I), and a salt formed by the compound of formula (I) with an organic base which provides a physiologically acceptable cation.

4. The compound, the racemate, the stereoisomer, the tautomer, the oxynitride, or the pharmaceutically acceptable salt thereof according to claim 1, wherein the compound of formula (I) is of formula (I'):

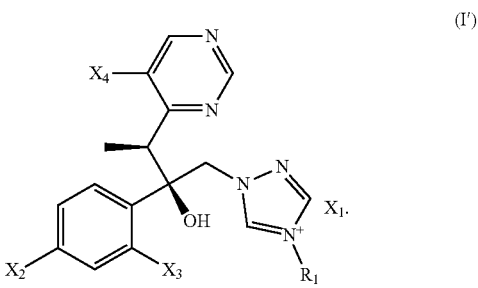

(I')

5. A compound selected from

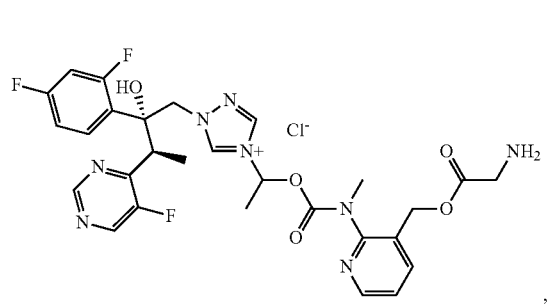

16001

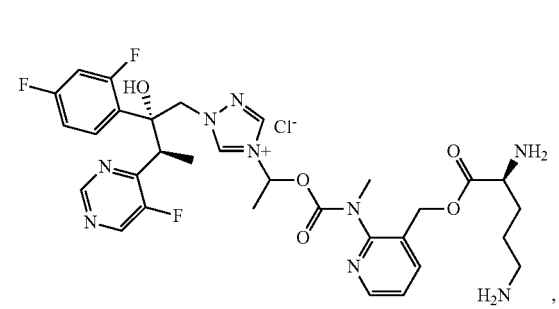

16002

,

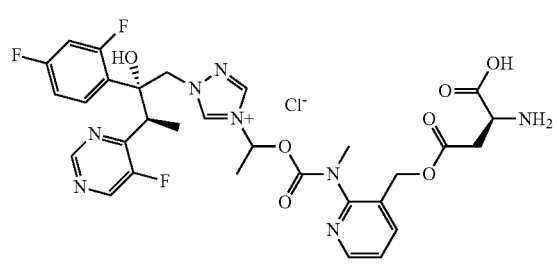

16003

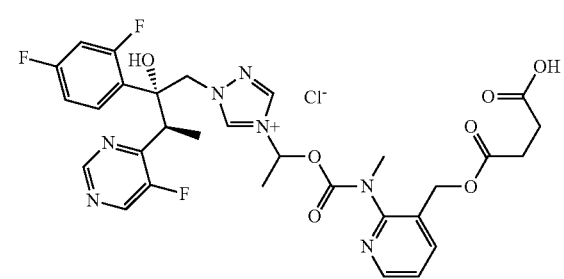

16004

,

-continued
16005
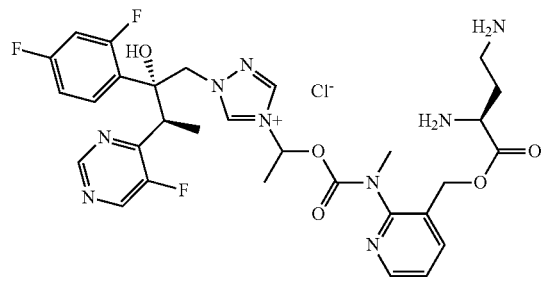
16006
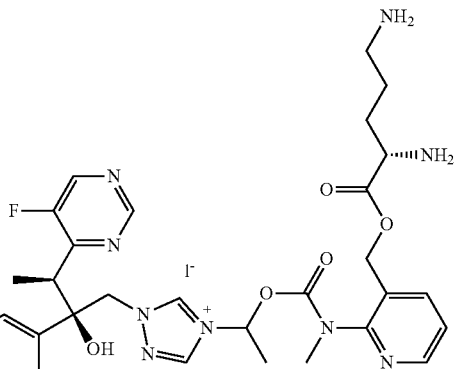
16007
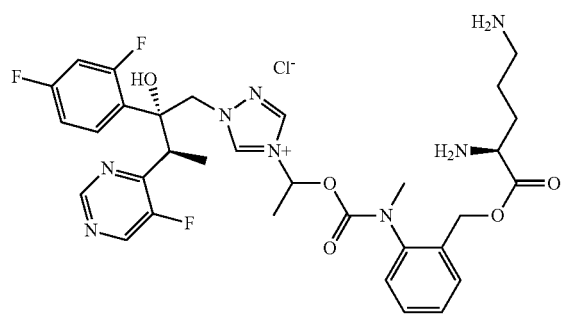
16008
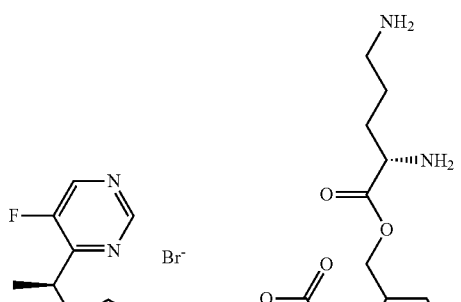
16009
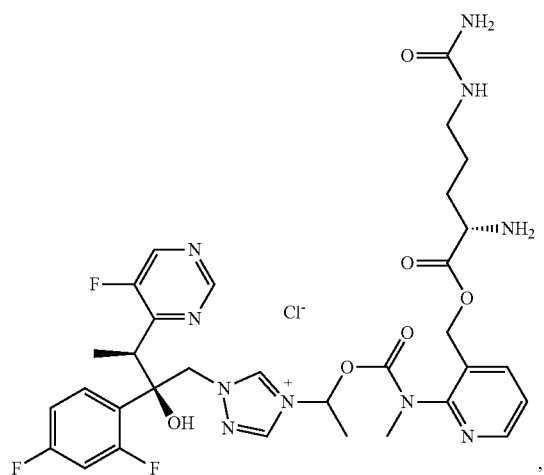
16010
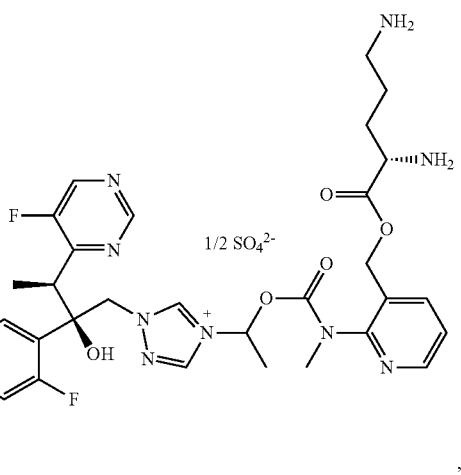

-continued
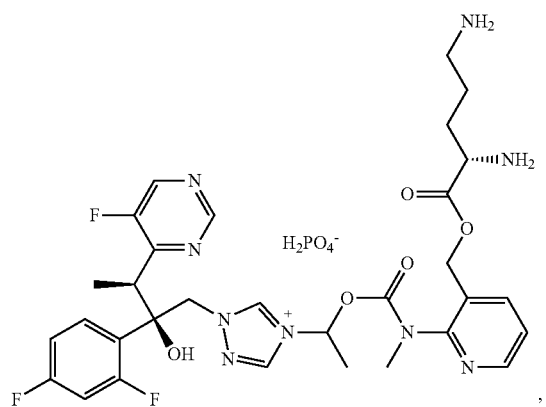
16011
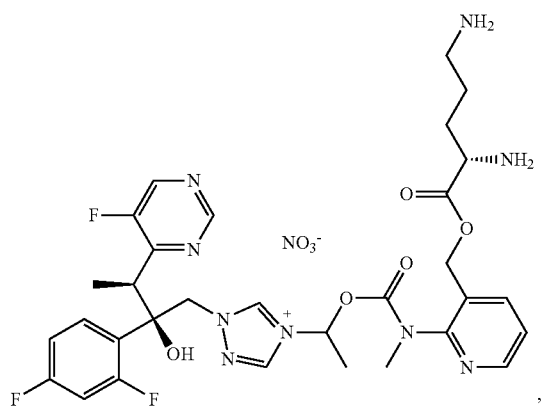
16012
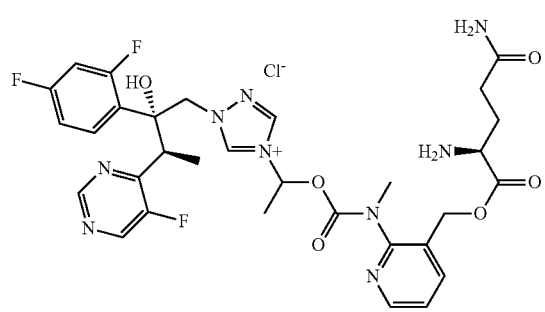
16013
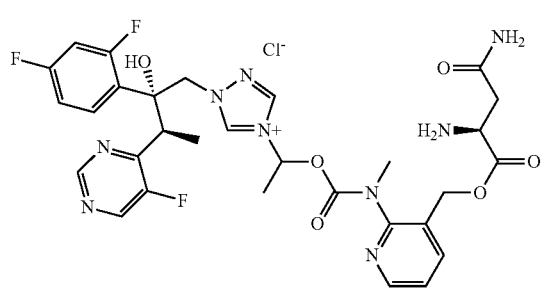
16014
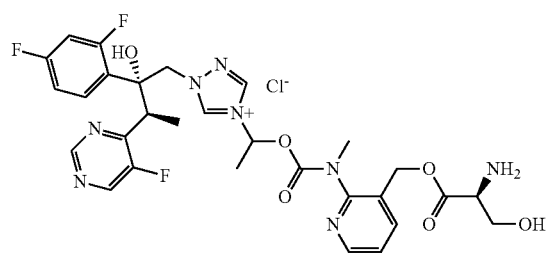
16015
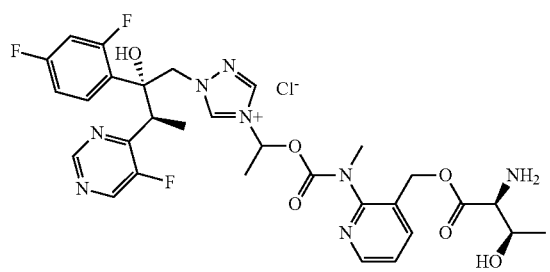
16016
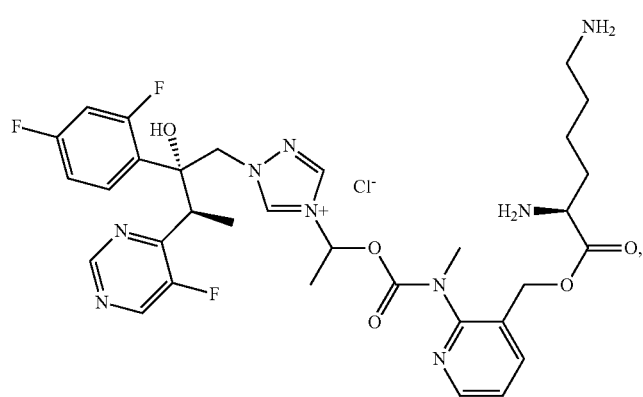
16017

-continued
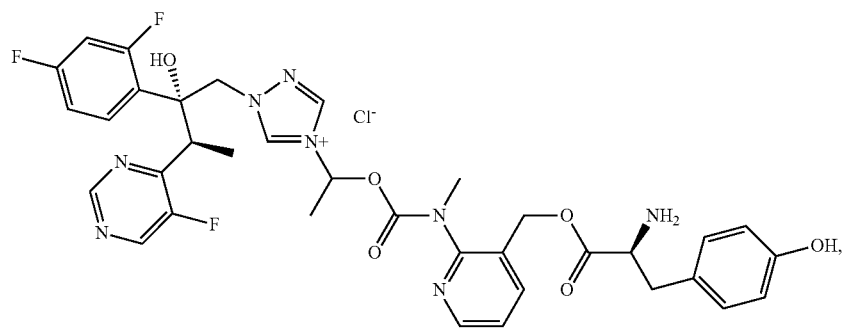
16018
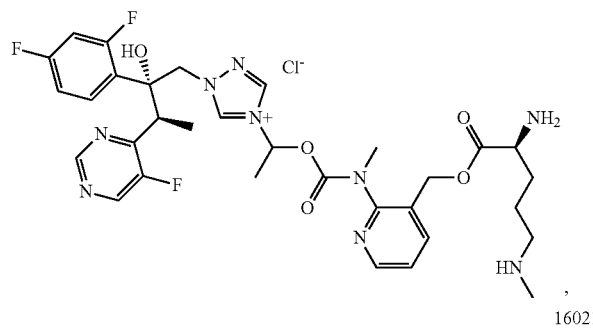
16019
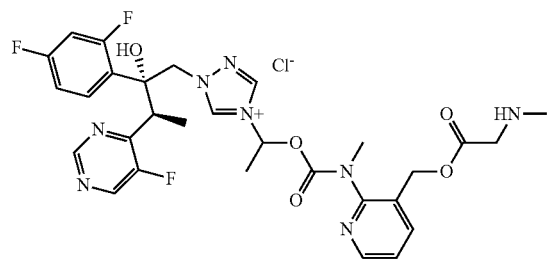
16020
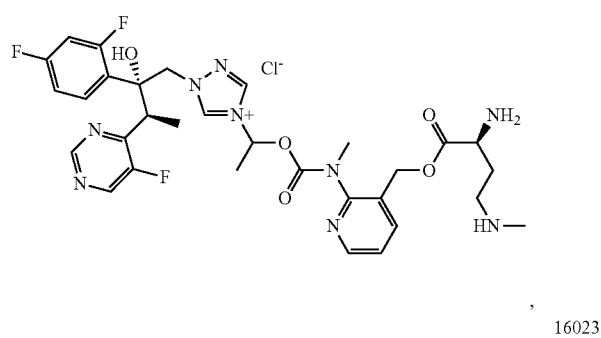
16021
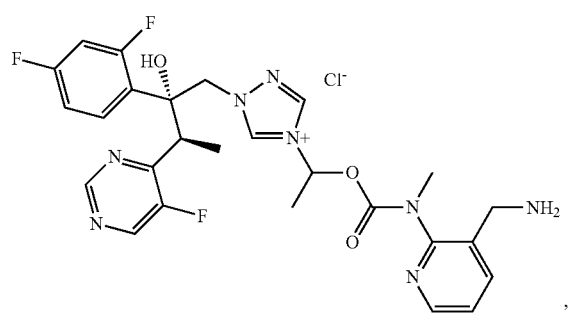
16022
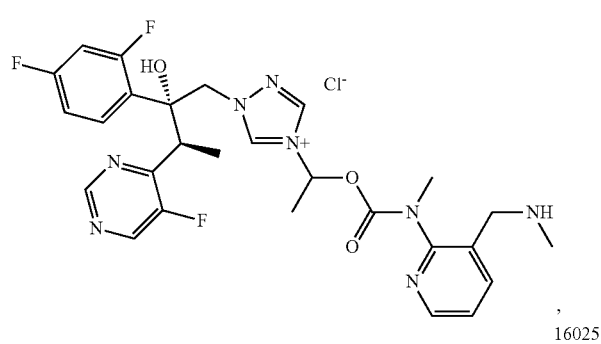
16023
16024
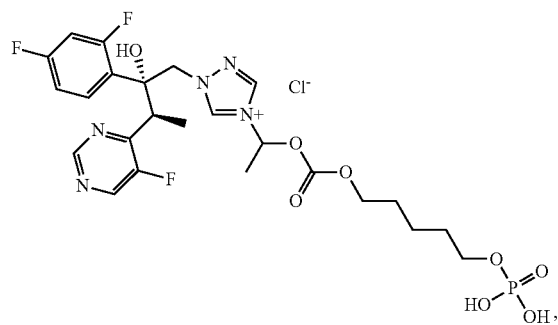
16025
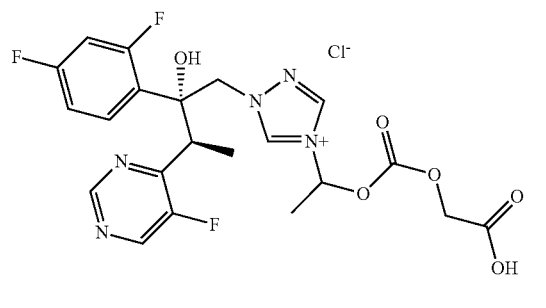
16026

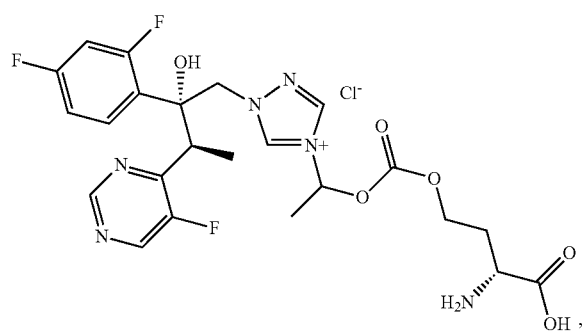
16027
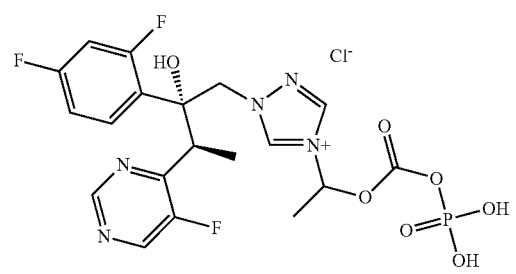
16028
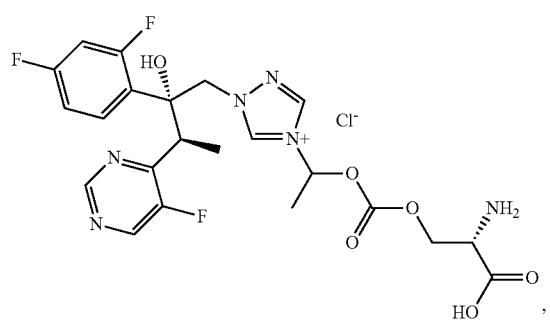
16029
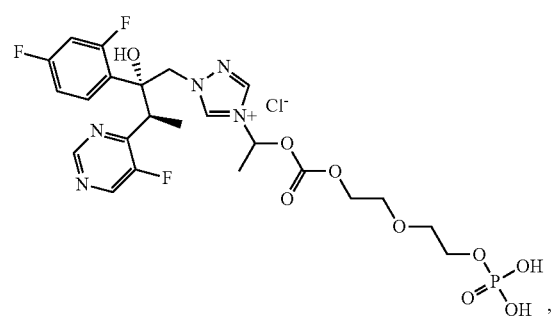
16030
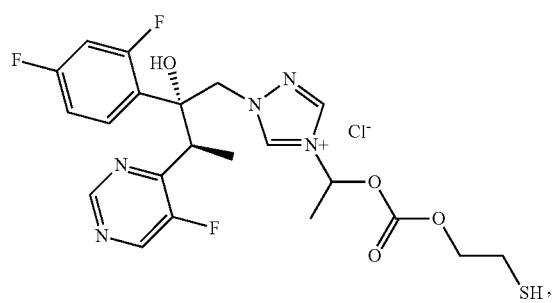
16031
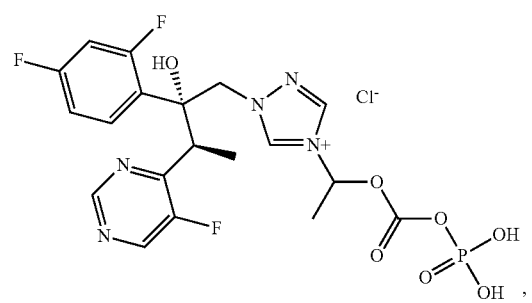
16032
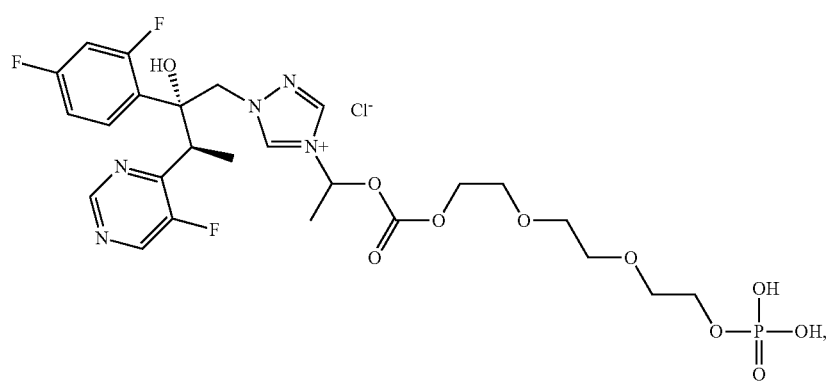
16033

-continued
16034
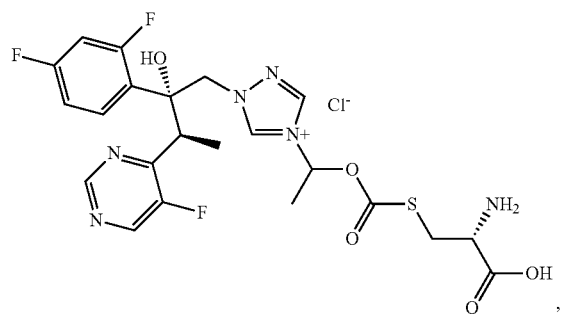
16035
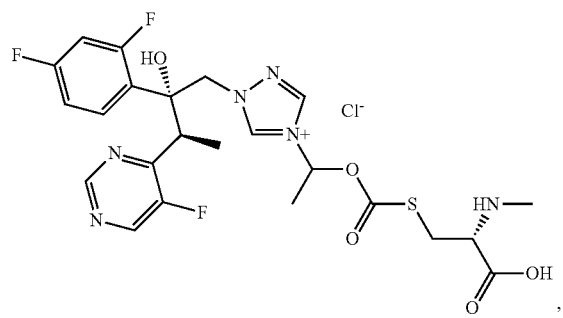
16036
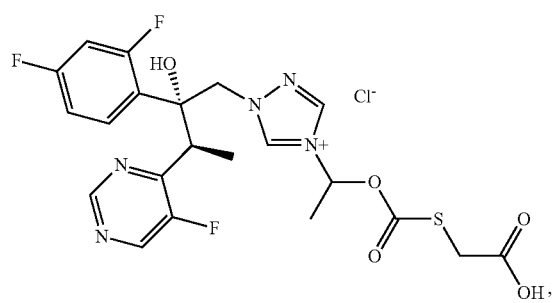
16037
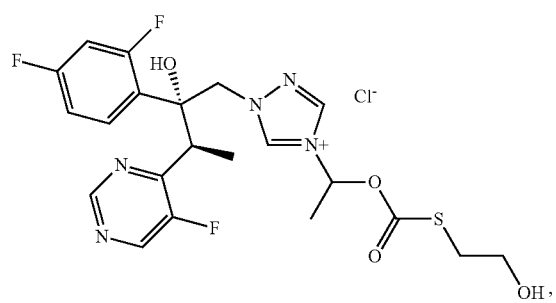
16038
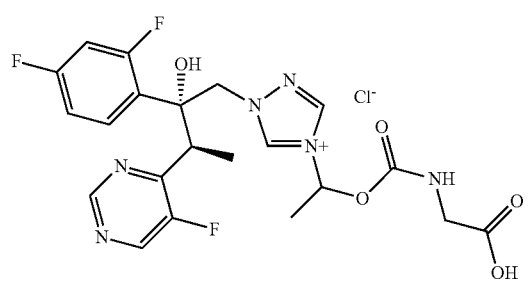
16039
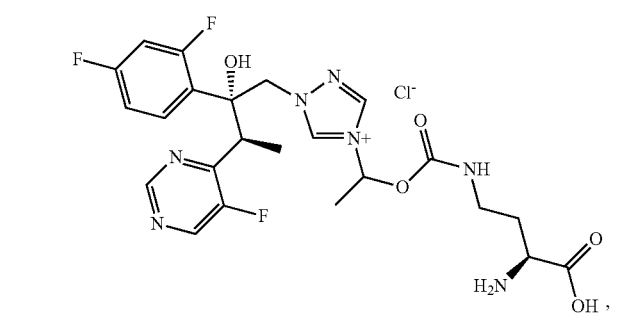
16040
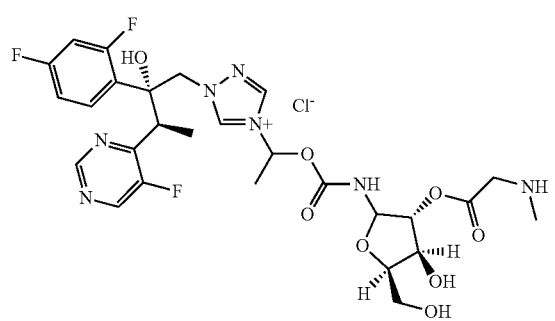
16041
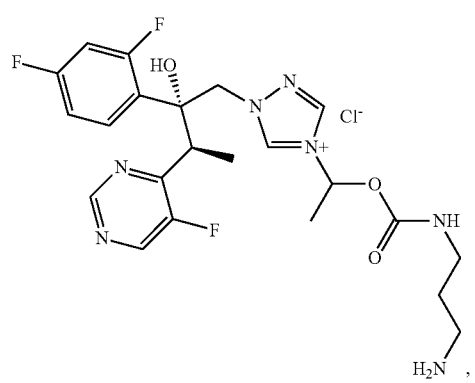

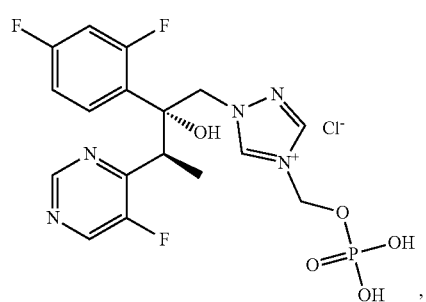
16042
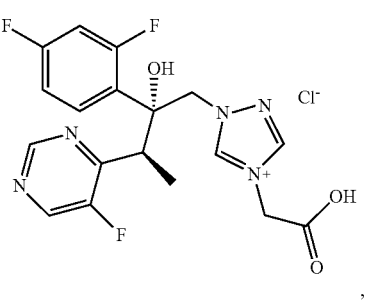
16043
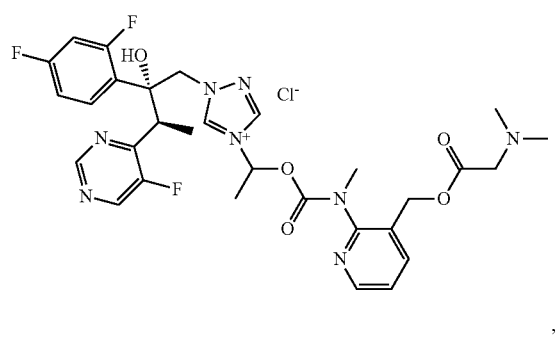
16045
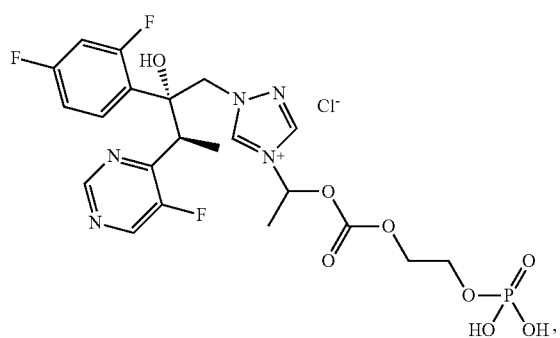
16046
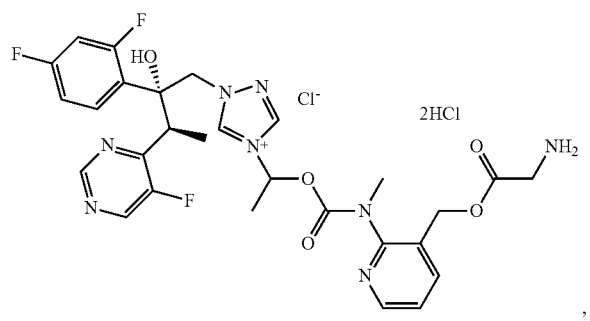
QR16001
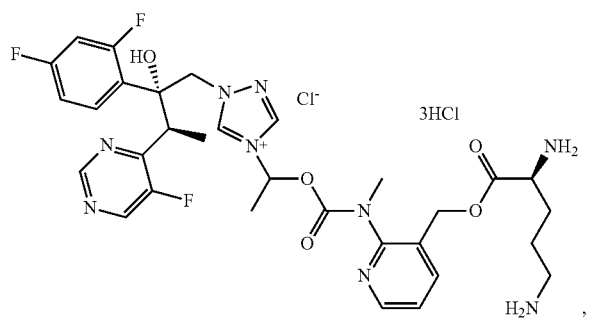
QR16002
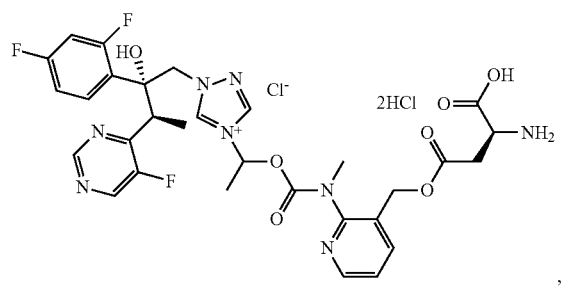
QR16003
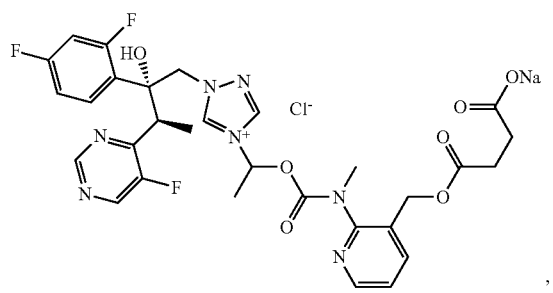
QR16004

-continued
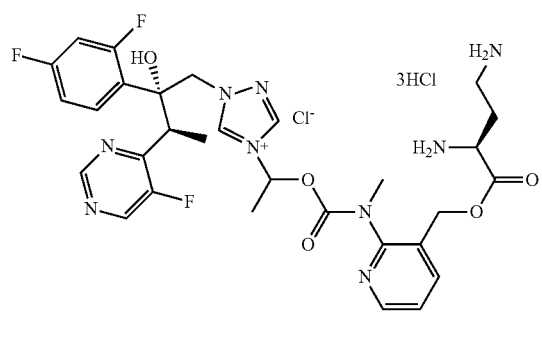
QR16005
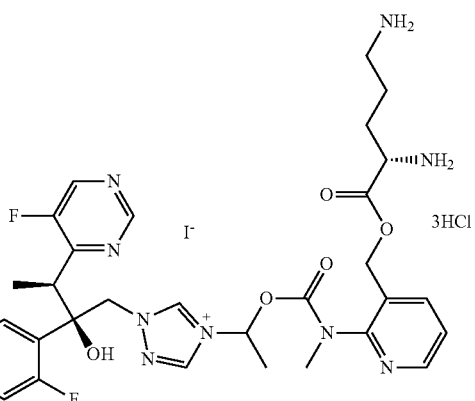
QR16006
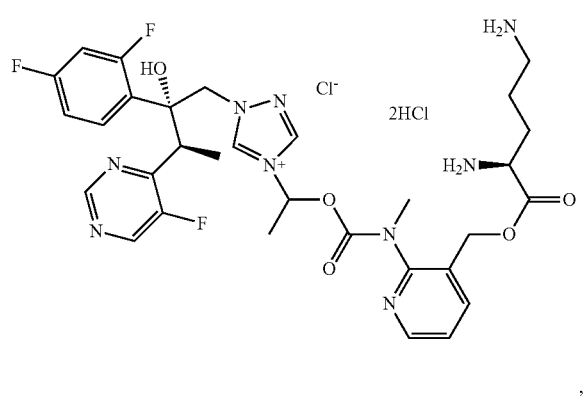
QR16007
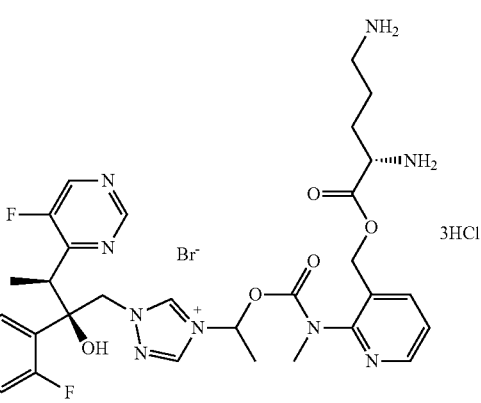
QR16008
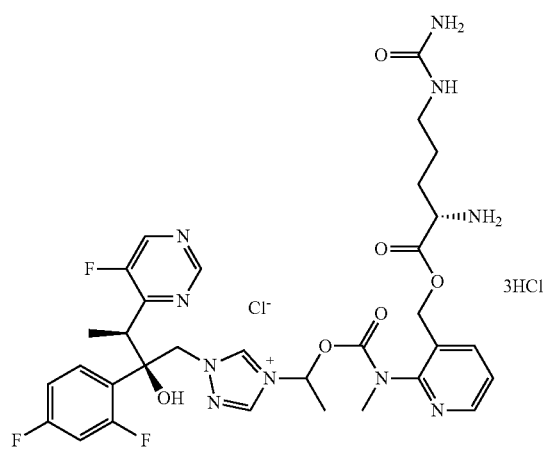
QR16009
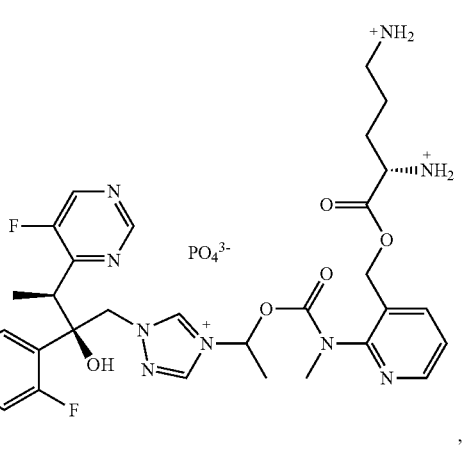
QR16011

-continued
QR16012
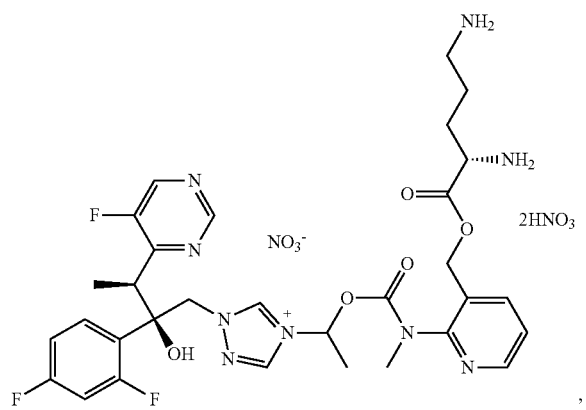
QR16013
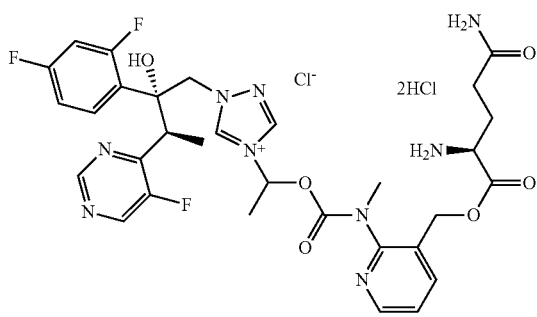
QR16014
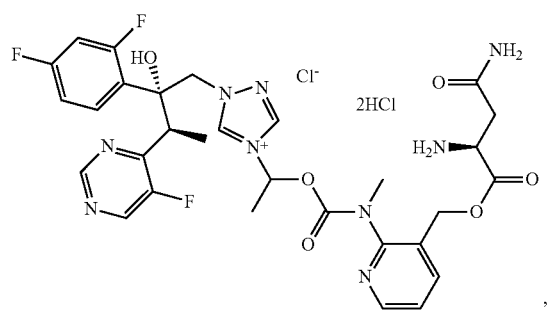
QR16015
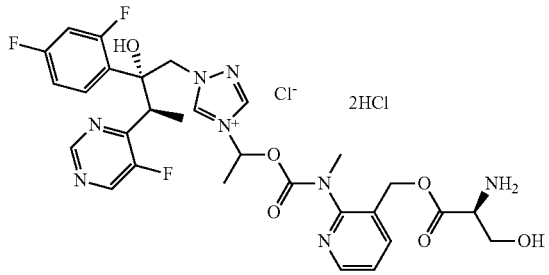
QR16016
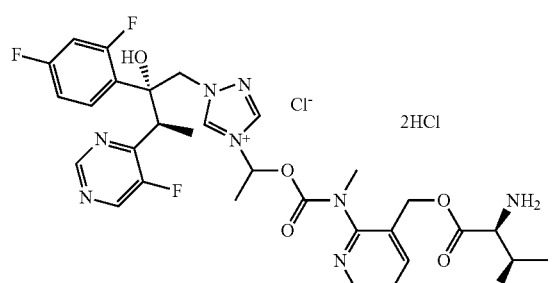
QR16017
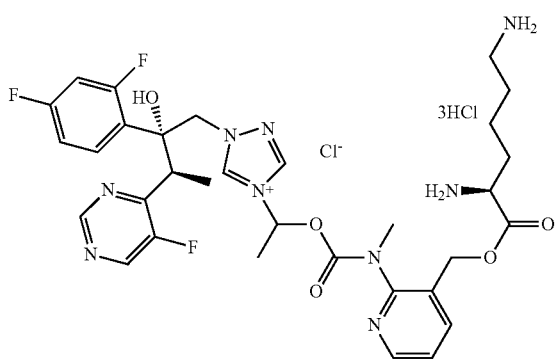
QR16018
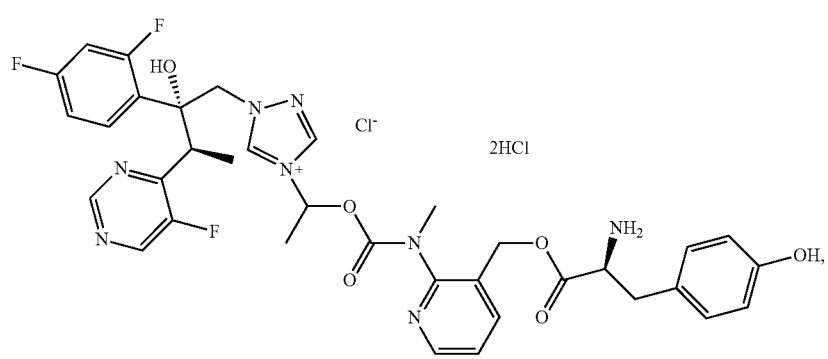

-continued
QR16019
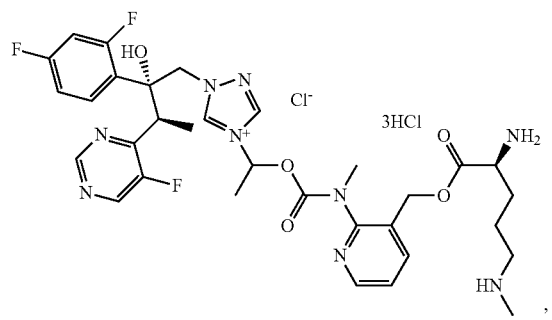
QR16020
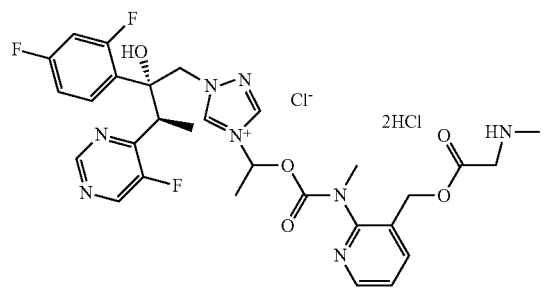
QR16021
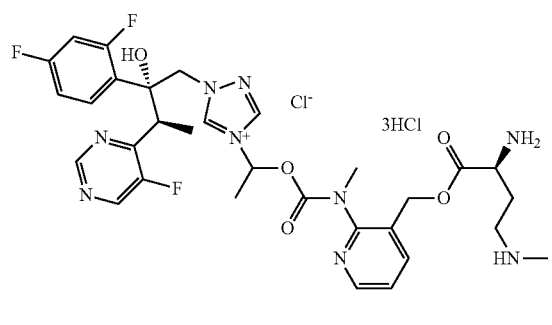
QR16022
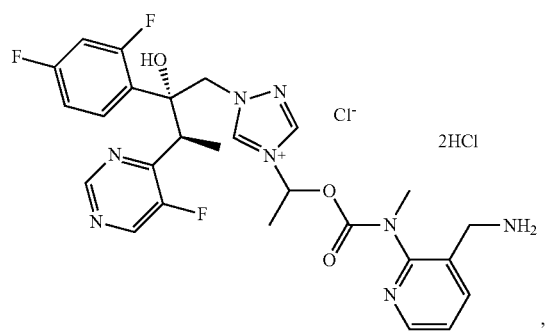
QR16023
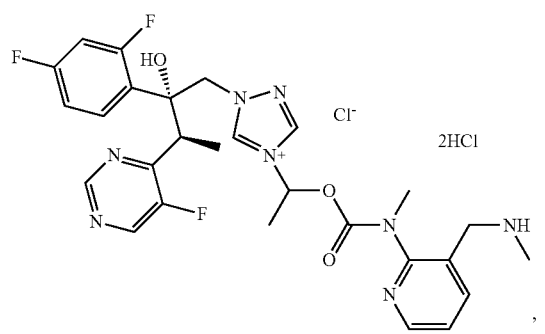
QR16024
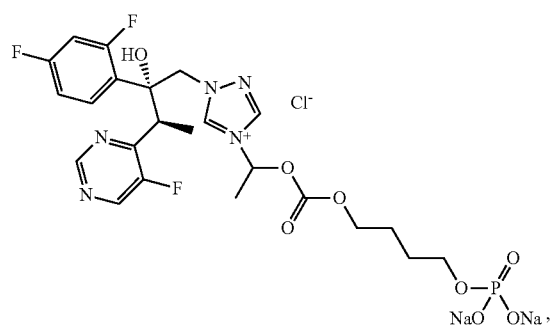
QR10625
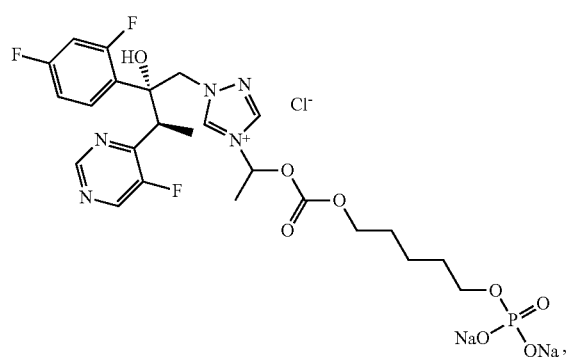
QR10626
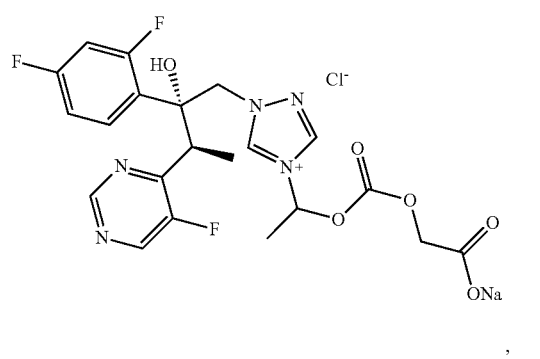

-continued
QR16027
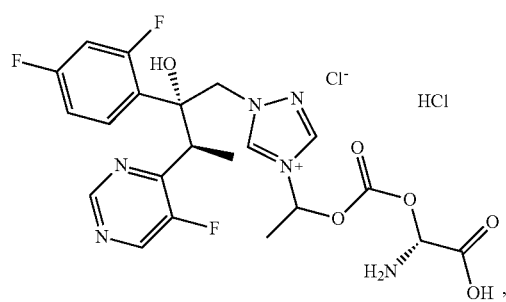
QR16028
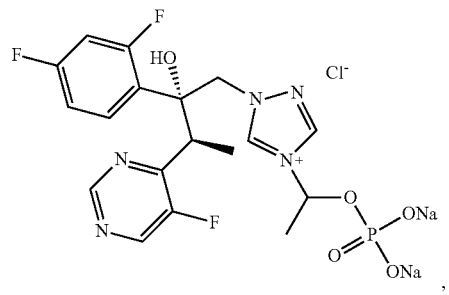
QR16029
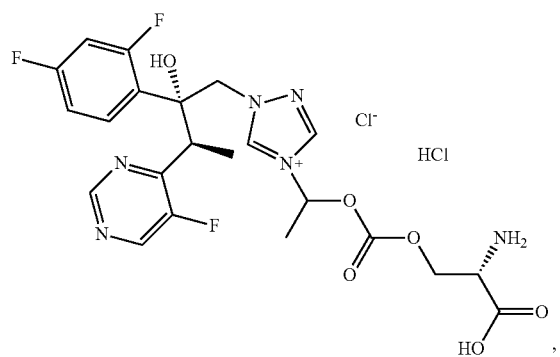
QR16030.
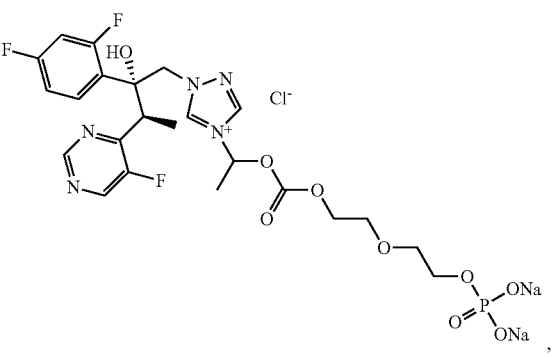
QR16032
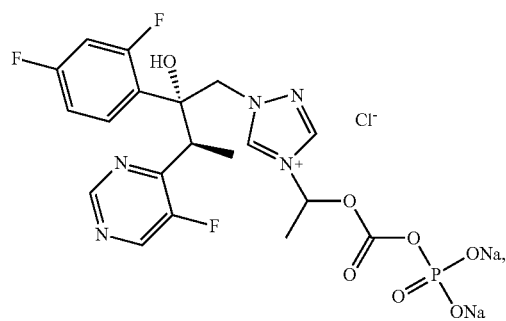
QR16033
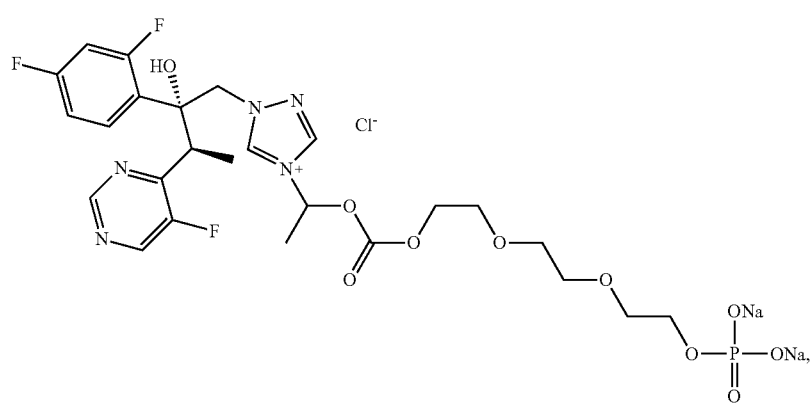

-continued
QR16034
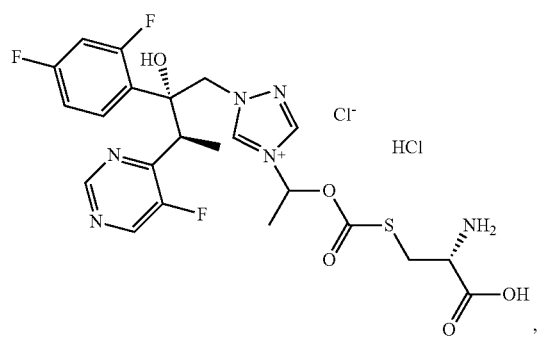
QR16035
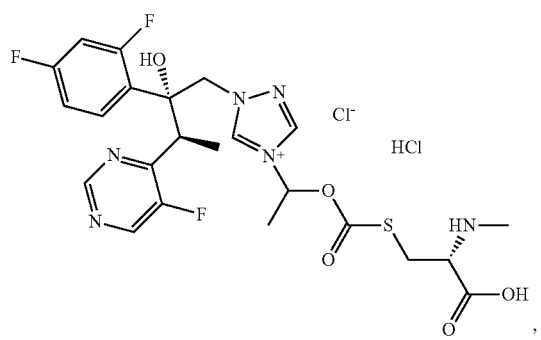
QR16036
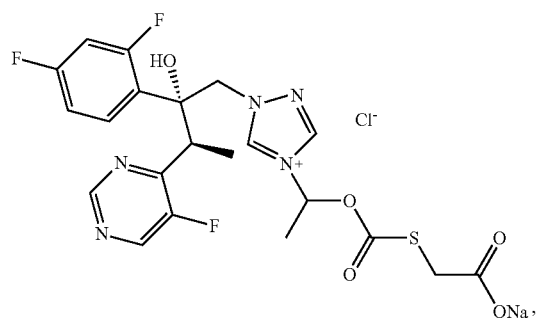
QR16038
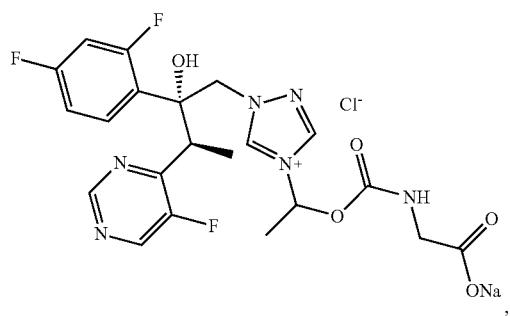
QR16039
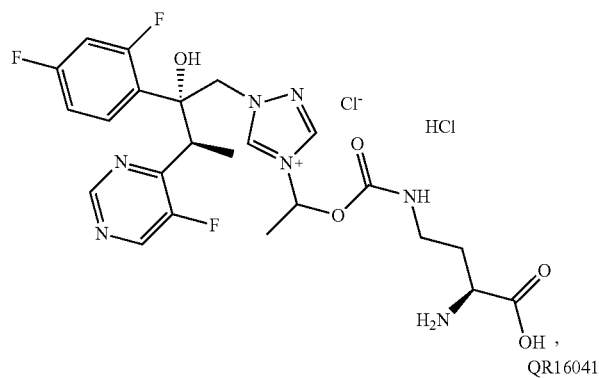
QR16040
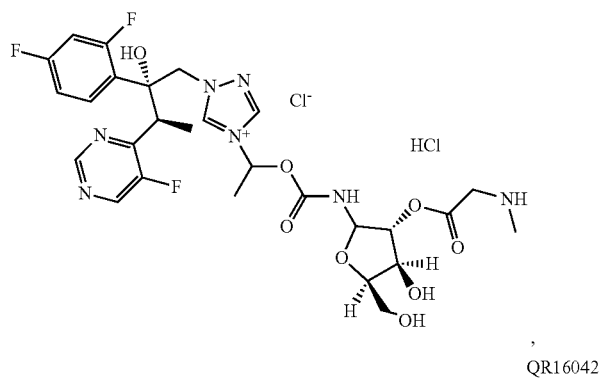
QR16041
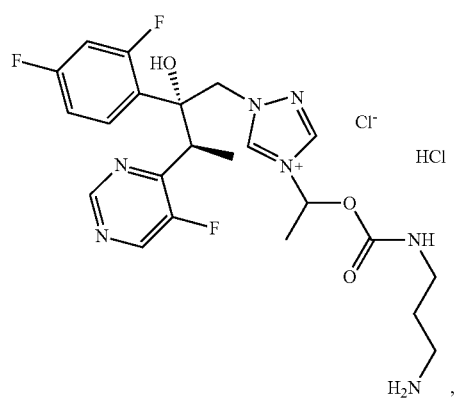
QR16042
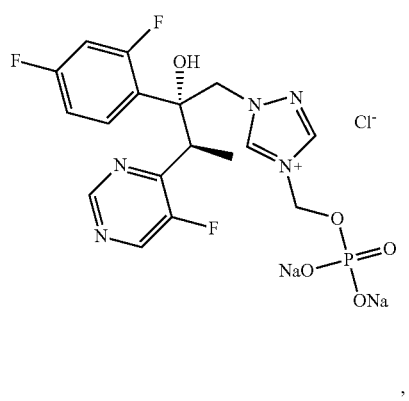

-continued
QR16043
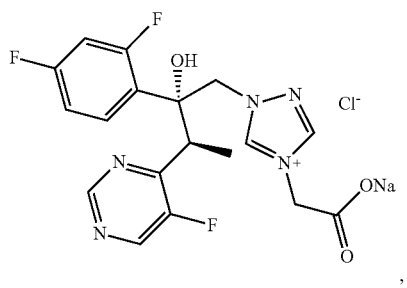
QR16045
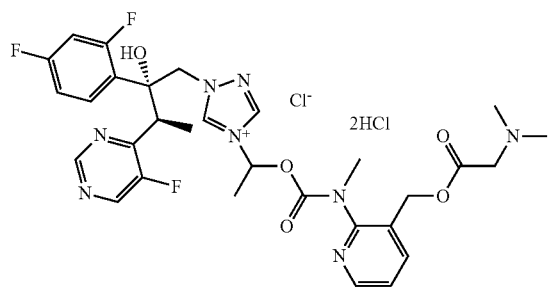
QR16046
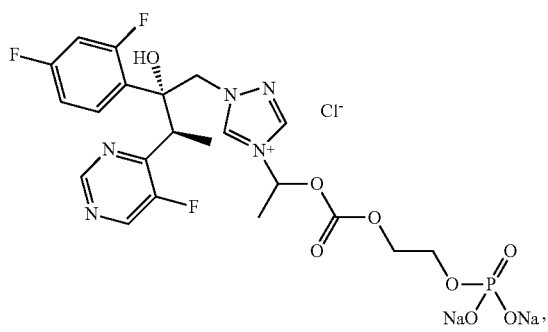
SF16001
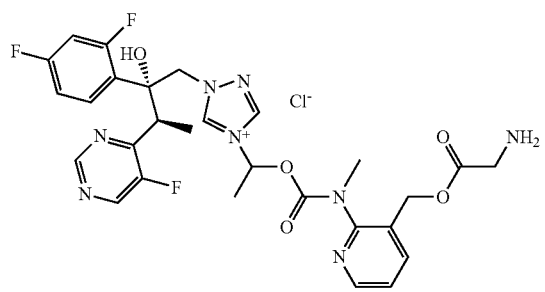
SF16002
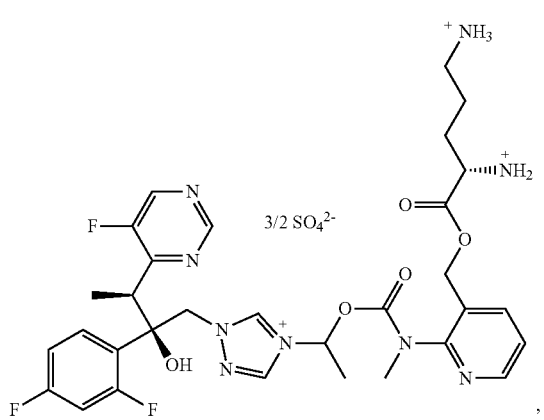
SF16020
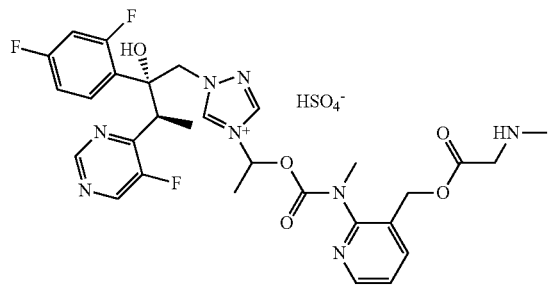
SF16013
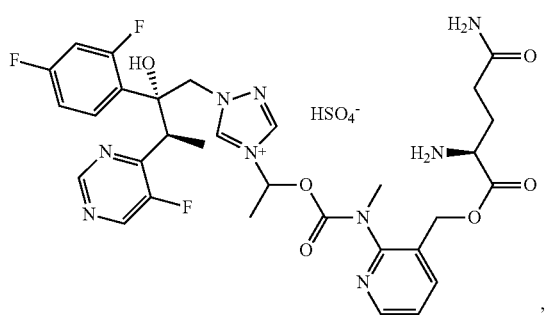
SF16014
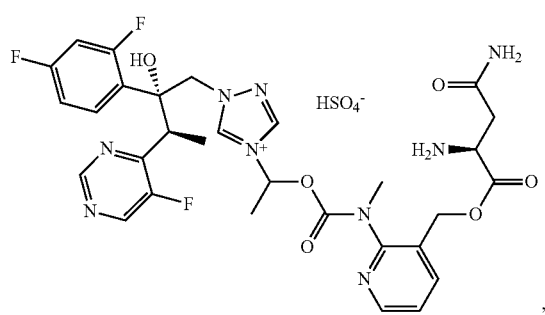

SF16015

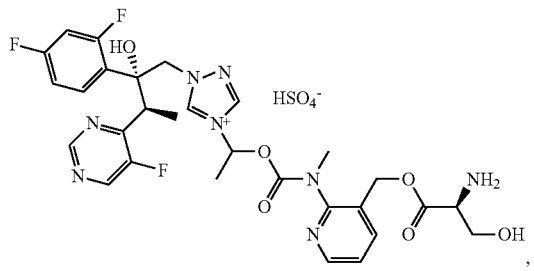

SF16016

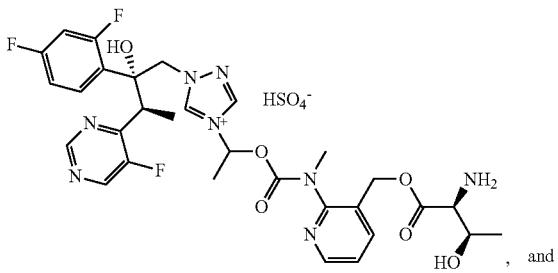
, and

SF16017

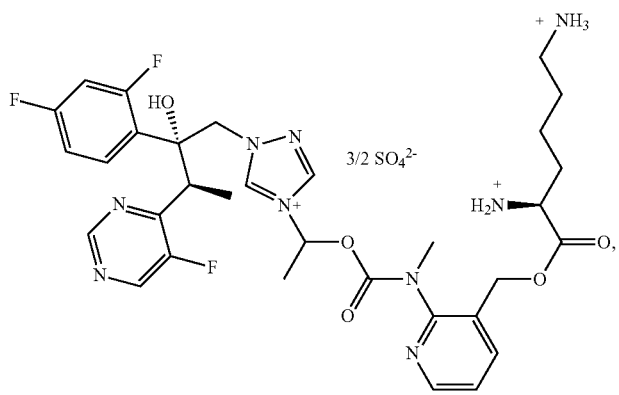

or a racemate, a stereoisomer, a tautomer, an oxynitride, or a pharmaceutically acceptable salt thereof.

6. A preparation method of the compound according to claim 1, comprising preparing the compound of formula (I) by using a compound of formula (II) as a starting material:

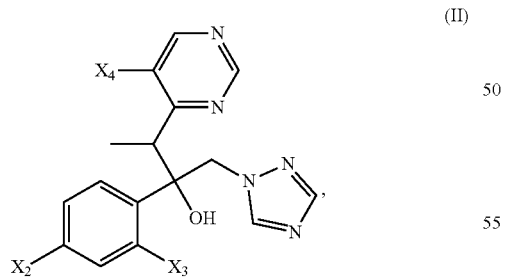

(II)

the preparation method comprises:
reacting the compound of formula (II) with a compound of $R_z$-L, wherein $R_z$ is $R_1$ or $R_1'$, wherein $R_1'$ is a functional group that reacts to form $R_1$, and L is a leaving group.

7. The preparation method according to claim 6, wherein the compound of formula (II) is a compound of formula (II'):

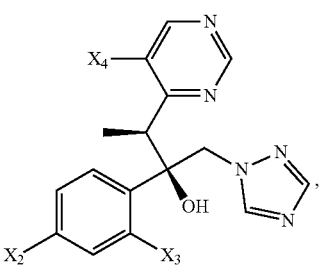

(II')

wherein the method comprises one of the methods selected from method (1) to method (5) in the following:

1) reacting a hydroxymethyl-substituted arylamine or heteroarylamine with an acylating reagent to form amide A-1, reacting amide A-1 with a carboxylic acid optionally containing a protecting group in the presence of a condensing agent to give compound A-2, and reacting compound A-2 and the compound of formula (II') to obtain compound A-3, optionally deprotecting compound A-3 to give compound A-4, and optionally subjecting compound A-4 to a salt-forming and/or salt-transforming step:

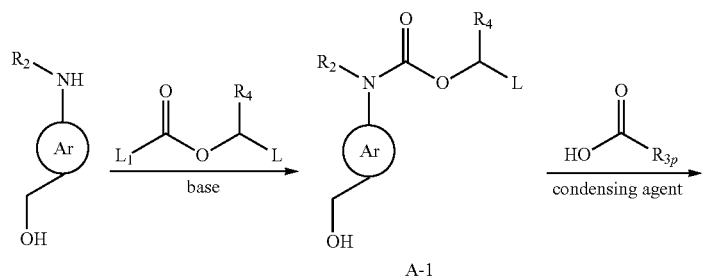
A-1
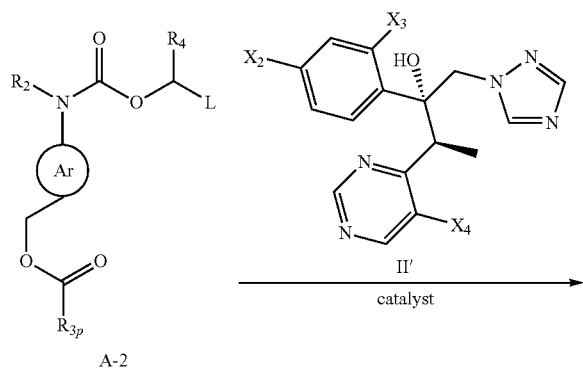
A-2
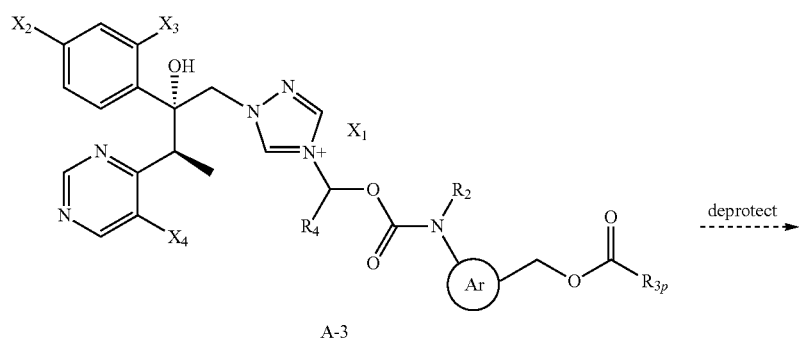
A-3
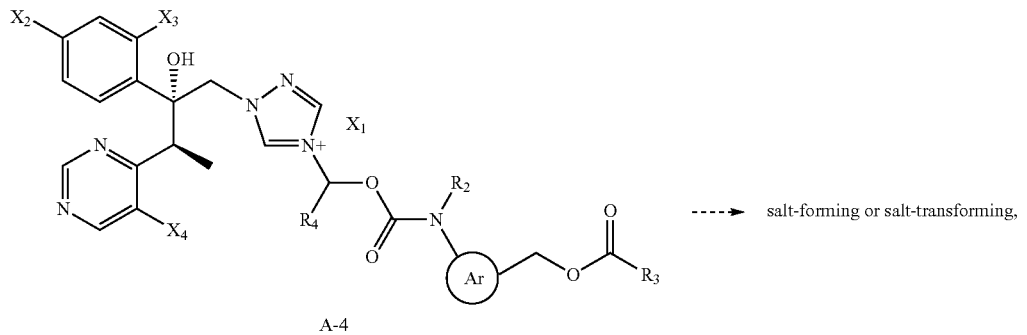
A-4 wherein R_{3p} represents R_3 or —R_3—PG, and PG is a protecting group;

2) reacting a substituted alcohol, substituted amine or substituted thiol optionally containing a protecting group with an acylating reagent to form compound B-1, reacting compound B-1 with the compound of formula (II') to obtain compound B-2, and optionally deprotecting compound B-2 to give compound B-3, optionally subjecting compound 3 to a salt-forming and/or salt-transforming step:

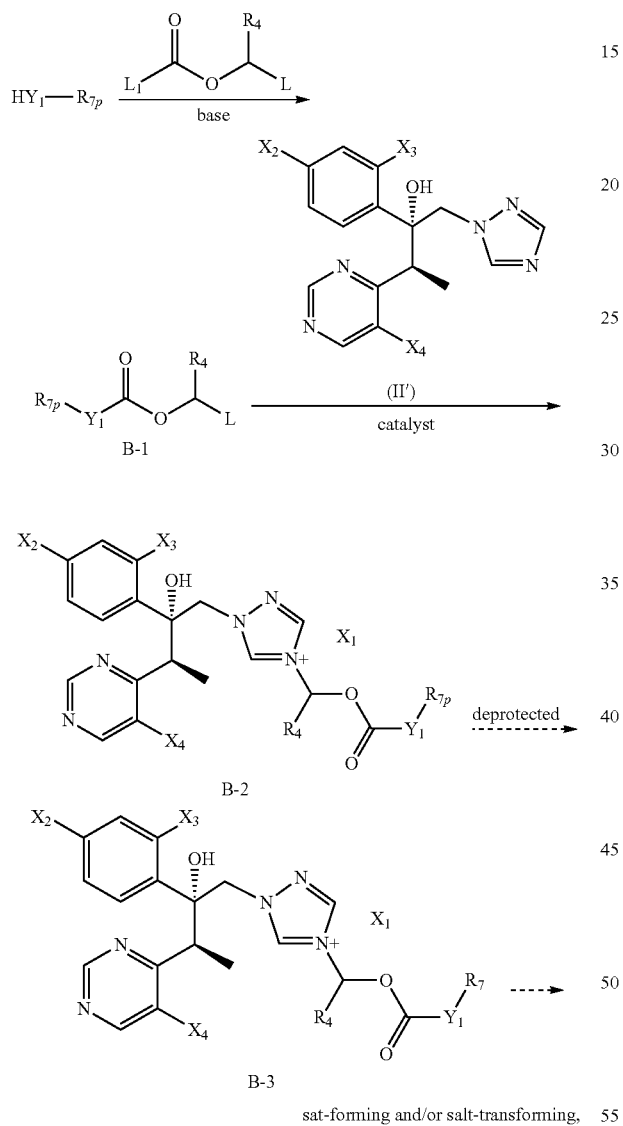

sat-forming and/or salt-transforming, wherein R_{7p} represents R_7 or —R_{7p}—PG;

3) reacting a diol as a starting material with phosphorus oxychloride di-tert-butyl ester to form compound C-1, acylating compound C-1 to obtain compound C-2, and reacting compound C-2 with the compound of formula (II') to give compound C-3; and deprotecting compound C-3 to give compound C-4; optionally subjecting compound C-4 to a salt-forming and/or salt-transforming step:

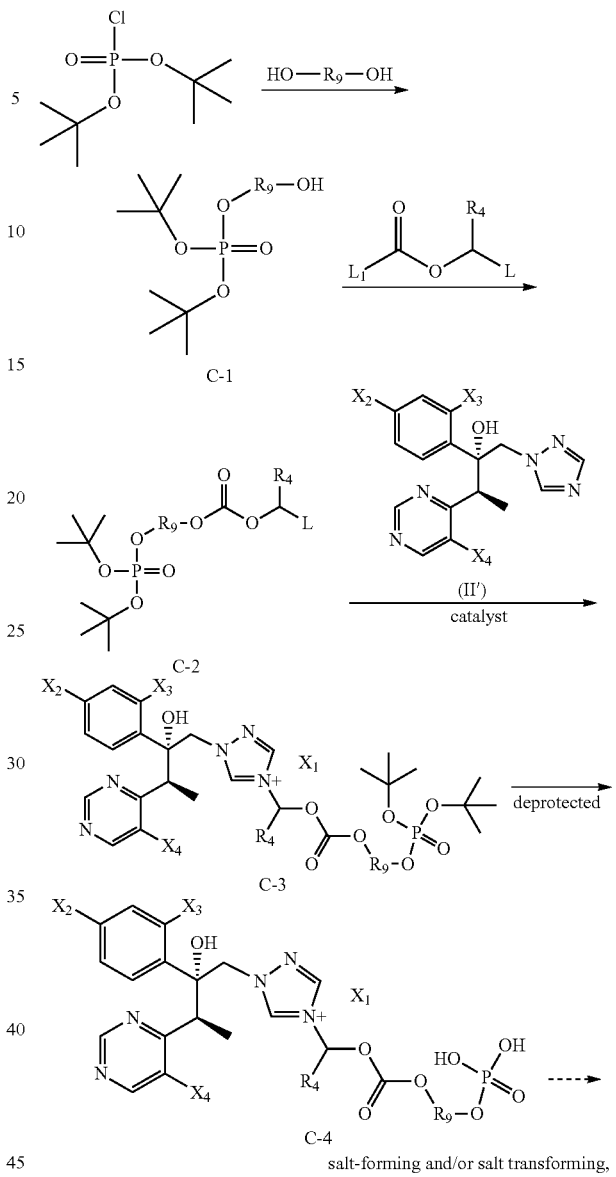

salt-forming and/or salt transforming, wherein $R_9$ is $(CH_2)_h$, and h is an integer of 1 to 12;

or $R_9$ is $[(CH_2)_2O]_x(CH_2)_y$, and x, y are independently selected from an integer of 1 to 12, inclusive;

4) reacting a starting material D-1 with an iodoalkane to form compound D-2, and reacting compound D-2 with the compound represented by formula (II') to obtain compound D-3, deprotecting compound D-3 to give compound D-4, and optionally subjecting compound D-4 maya salt-forming and/or salt-transforming step:

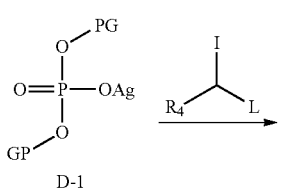

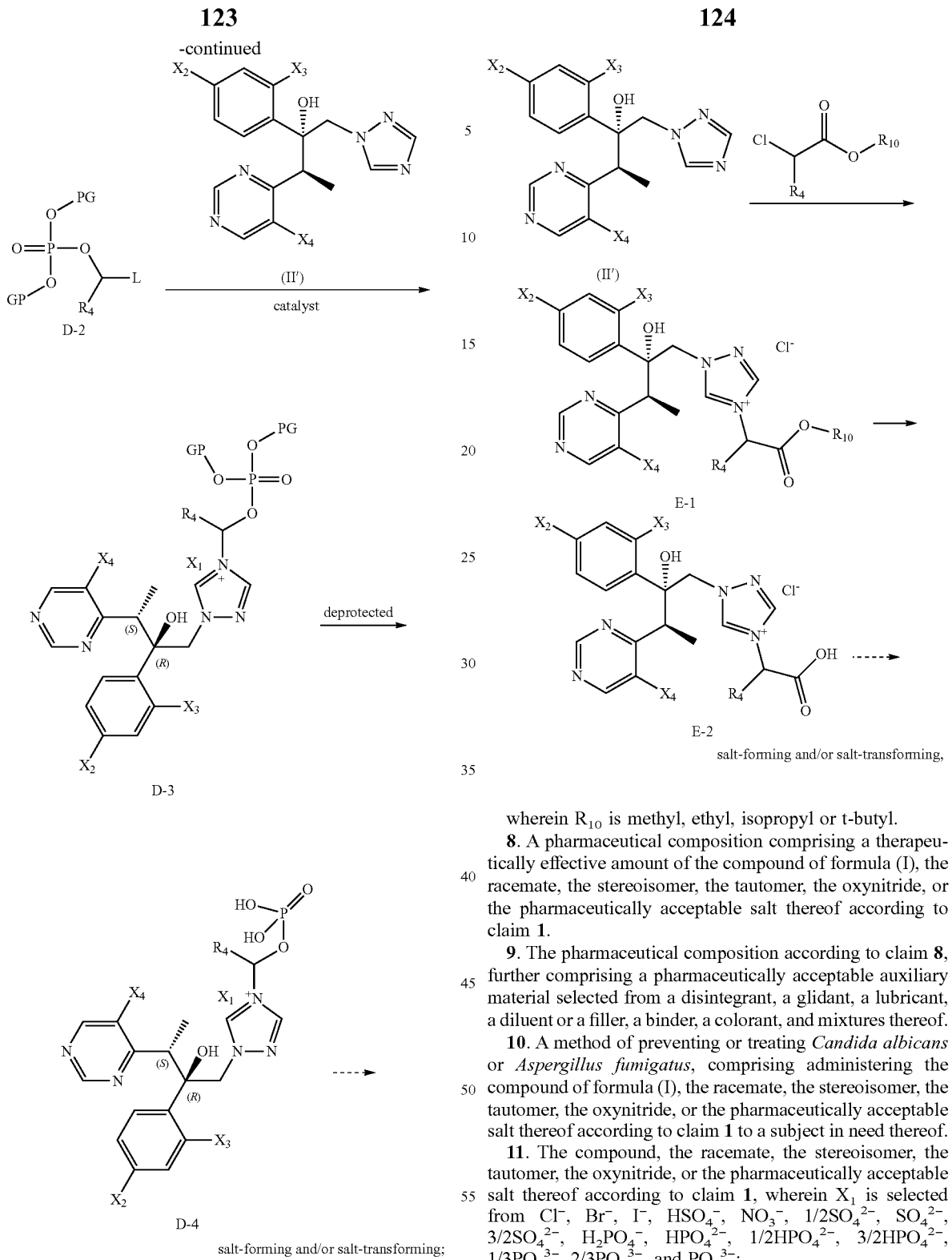

5) reacting the compound represented by the formula (II') with a chloroacetic acid ester reagent to obtain compound E-1, subjecting compound of E-1 to a hydrolysis reaction to obtain compound E-2, and optionally subjecting compound E-2 a salt-forming and/or salt-transforming step:

wherein $R_{10}$ is methyl, ethyl, isopropyl or t-butyl.

8. A pharmaceutical composition comprising a therapeutically effective amount of the compound of formula (I), the racemate, the stereoisomer, the tautomer, the oxynitride, or the pharmaceutically acceptable salt thereof according to claim 1.

9. The pharmaceutical composition according to claim 8, further comprising a pharmaceutically acceptable auxiliary material selected from a disintegrant, a glidant, a lubricant, a diluent or a filler, a binder, a colorant, and mixtures thereof.

10. A method of preventing or treating *Candida albicans* or *Aspergillus fumigatus*, comprising administering the compound of formula (I), the racemate, the stereoisomer, the tautomer, the oxynitride, or the pharmaceutically acceptable salt thereof according to claim 1 to a subject in need thereof.

11. The compound, the racemate, the stereoisomer, the tautomer, the oxynitride, or the pharmaceutically acceptable salt thereof according to claim 1, wherein $X_1$ is selected from $Cl^-$, $Br^-$, $I^-$, $HSO_4^-$, $NO_3^-$, $1/2SO_4^{2-}$, $SO_4^{2-}$, $3/2SO_4^{2-}$, $H_2PO_4^-$, $HPO_4^{2-}$, $1/2HPO_4^{2-}$, $3/2HPO_4^{2-}$, $1/3PO_4^{3-}$, $2/3PO_4^{3-}$, and $PO_4^{3-}$;

$R_2$ is selected from H, unsubstituted $C_{1-40}$ alkyl, and $C_{1-40}$ alkyl that is substituted by one or more $R_a$;

$R_3$ is unsubstituted $C_{1-40}$ alkyl, or $C_{1-40}$ alkyl substituted by 1, 2 or 3 functional groups independently selected from $C_{1-6}$ alkyl, $-NH_2$, $-COOH$, $-OH$, $-CONH_2$, $-N(CH_3)_2$, $-NH(CH_3)$, $-NHCONH_2$, $-NH(CH_2)_k$ $CH_3$, o-hydroxyphenyl, m-hydroxyphenyl, p-hydroxyphenyl, $-(CH_2)_k-NH_2$, $-CH(NH_2)-(CH_2)_k-NH_2$, $-CH(NH_2)-(CH_2)_k-COOH$, $-(CH_2)_k-$ CH(NH$_2$)—COOH, —(CH$_2$)$_k$—COOH, —CH(NH$_2$)—(CH$_2$)$_k$—NH—CONH$_2$, —CH(NH$_2$)—(CH$_2$)$_k$—CONH$_2$, —CH(NH$_2$)—(CH$_2$)$_k$—OH, —CH(NH$_2$)—(CH$_2$)$_k$—CH(OH)—CH$_3$, —CH(NH$_2$)—(CH$_2$)$_k$—(C$_6$H$_4$)—OH, —CH(NH$_2$)—(CH$_2$)$_k$—NH—(CH$_2$)$_p$—CH$_3$, —(CH$_2$)$_k$—NH—(CH$_2$)$_p$—CH$_3$, and —(CH$_2$)$_k$—N(CH$_3$)$_2$;

wherein Ar is selected from C$_{6-10}$ aryl, 5-10 membered heteroaryl, pyridyl, phenyl,

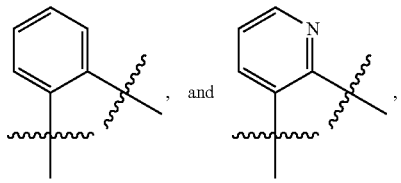 [SMILES: *c1ccccc1* ; *c1cccnc1*]

wherein the 2-position C atom of the pyridyl is bonded to the N atom, and the 3-position C atom of the pyridyl is bonded to the methylene group;

R$_7$ is —(CH$_2$)$_k$—OP(O)(OH)$_2$, —(CH$_2$)$_k$—COOH, —(CH$_2$)$_k$—CH(NH$_2$)—COOH, —[(CH$_2$)$_z$—O]$_k$—OP(O)(OH)$_2$, —(CH$_2$)$_k$—SH, —(CH$_2$)$_k$—CH[NH(CH$_3$)]—COOH, —(CH$_2$)$_k$—OH, —(CH$_2$)$_k$—NH$_2$, or

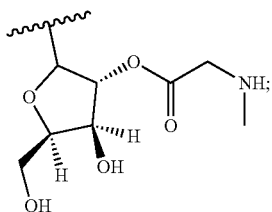 [SMILES: *C1O[C@H](CO)[C@H](O)[C@H]1OC(=O)CNC]

R$_8$ is a substituted or unsubstituted functional group selected from C$_{1-40}$ alkyl, 3-20 membered heterocyclyl, and C$_{3-20}$ cycloalkyl, wherein the substitutents are 1, 2 or 3 functional groups independently selected from —OP(O)(OH)$_2$, —COOH, —NH$_2$, —SH, —OH, —NHCH$_3$, —OC(O)CH$_2$NHCH$_3$, and —CH$_2$OH;

Y$_1$ and Y$_2$ are independently selected from a chemical bond, —O—, —S—, —CH$_2$—, —NH—, —CH$_2$— substituted by one or more R$_a$, and —NH— substituted by one or more R$_a$; and k and p are independently selected from an integer of 0 to 16, inclusive.

12. The compound, the racemate, the stereoisomer, the tautomer, the oxynitride, or the pharmaceutically acceptable salt thereof according to claim 1, wherein the pharmaceutically acceptable salt is an acid addition salt formed by reacting the compound of formula (I) with an acid selected from: hydrochloric acid, hydrofluoric acid, hydrobromic acid, hydroiodic acid, sulfuric acid, pyrosulfuric acid, phosphoric acid, nitric acid, formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectic acid, persulfate, 3-phenylpropionic acid, picric acid, pivalic acid, 2-hydroxyethanesulfonic acid, itaconic acid, sulfamic acid, trifluoromethanesulfonic acid, lauryl sulfate, ethanesulfonic acid, benzenesulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid, and thiocyanic acid; wherein the acid addition salt is of formula (IA):

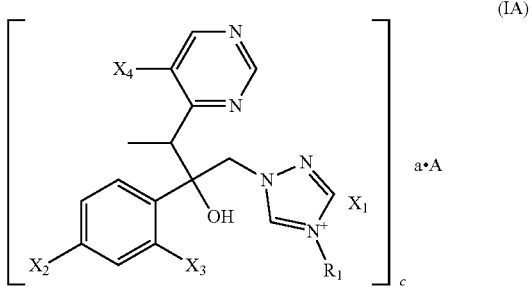

(IA)

wherein A represents an acid that forms the acid addition salt with the compound of formula (I);

a is 1, 2, 3, 4 or 5, representing a number of molecules of A;

c is 1, 2, 3, 4, or 5, representing a number of molecules of the compound of formula (I) depicted in the square bracket in formula (IA); and wherein A is selected from hydrochloric acid, sulfuric acid, benzenesulfonic acid, p-toluenesulfonic acid, phosphoric acid, fumaric acid, citric acid, tartaric acid, and lactic acid.

13. The compound, the racemate, the stereoisomer, the tautomer, the oxynitride, or the pharmaceutically acceptable salt thereof according to claim 1, wherein the pharmaceutically acceptable salt is a salt formed by the compound of formula (I) with sodium ion, potassium ion, calcium ion, magnesium ion, N-methylglucamine, dimethyl glucosamine, ethyl glucosamine, lysine, dicyclohexylamine, 1,6-hexamethylenediamine, ethanolamine, glucosamine, meglumine, sarcosine, serinol, trishydroxymethylaminomethane, aminopropanediol, or 1-amino-2,3,4-butanetriol.

14. The compound, the racemate, the stereoisomer, the tautomer, the oxynitride, or the pharmaceutically acceptable salt thereof according to claim 1, wherein the pharmaceutically acceptable salt is a salt formed by —COOH group in the compound of formula (I) with sodium ion, potassium ion, calcium ion, magnesium ion, N-methylglucamine, dimethyl glucosamine, ethyl glucosamine, lysine, dicyclohexylamine, 1,6-hexamethylenediamine, ethanolamine, glucosamine, meglumine, sarcosine, serinol, trishydroxymethylaminomethane, aminopropanediol, or 1-amino-2,3,4-butanetriol.

15. The compound, the racemate, the stereoisomer, the tautomer, the oxynitride, or the pharmaceutically acceptable salt thereof according to claim 1, wherein, when one or more of M$_1$, M$_2$, and M$_3$ are H, the pharmaceutically acceptable salt is formed by —OP(O)(OM$_1$)(OM$_2$), —P(O)(OM$_1$)(OM$_2$), —OS(O)$_2$OM$_3$, or —S(O)$_2$OM$_3$ and sodium ion, potassium ion, calcium ion, magnesium ion, N-methyl glucosamine, dimethyl glucosamine, ethyl glucosamine, lysine, dicyclohexylamine, 1,6-hexamethylenediamine, ethanolamine, glucosamine, meglumine, sarcosine, serinol, tris-hydroxymethylaminomethane, aminopropanediol, or 1-amino-2,3,4-butanetriol.

* * * * *